United States Patent
Yoon et al.

(10) Patent No.: US 12,171,144 B2
(45) Date of Patent: Dec. 17, 2024

(54) ORGANIC COMPOUND, ORGANIC LIGHT EMITTING DIODE AND ORGANIC LIGHT EMITTING DEVICE INCLUDING THE ORGANIC COMPOUND

(71) Applicants: LG DISPLAY CO., LTD, Seoul (KR); KOREA UNIVERSITY RESEARCH AND BUSINESS FOUNDATION, Seoul (KR)

(72) Inventors: Kyung-Jin Yoon, Paju-si (KR); Dae-Wi Yoon, Paju-si (KR); Ji-Ae Lee, Paju-si (KR); Su-Na Choi, Paju-si (KR); Dong-Hoon Choi, Paju-si (KR); Min-Ju Cho, Paju-si (KR); JiWon Yoon, Paju-si (KR)

(73) Assignees: LG DISPLAY CO., LTD., Seoul (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 18/474,865

(22) Filed: Sep. 26, 2023

(65) Prior Publication Data
US 2024/0090326 A1 Mar. 14, 2024

Related U.S. Application Data

(62) Division of application No. 16/930,719, filed on Jul. 16, 2020, now Pat. No. 11,825,741.

(30) Foreign Application Priority Data

Jul. 17, 2019 (KR) .................. 10-2019-0086572

(51) Int. Cl.
*H10K 85/60* (2023.01)
*C07D 491/20* (2006.01)
(Continued)

(52) U.S. Cl.
CPC ......... *H10K 85/657* (2023.02); *C07D 491/20* (2013.01); *C07D 495/20* (2013.01);
(Continued)

(58) Field of Classification Search
CPC .. H10K 85/657; H10K 85/6572; H10K 50/11; C07D 491/20; C07D 495/20;
(Continued)

(56) References Cited

U.S. PATENT DOCUMENTS 9,896,467 B1 * 2/2018 Chi ................... C07F 9/6561
9,896,487 B2 2/2018 Chi et al.
(Continued)

FOREIGN PATENT DOCUMENTS

CN 108164532 A 6/2018
CN 109956964 A 7/2019
(Continued)

OTHER PUBLICATIONS

Gangala et al., "Spiro-linked organic small molecules as hole-transport materials for perovskite solar cells", Journal of Materials Chemistry A, vol. 6, Sep. 13, 2018, pp. 18750-18765.
(Continued)

*Primary Examiner* — Shane Fang
(74) *Attorney, Agent, or Firm* — Birch, Stewart, Kolasch & Birch, LLP

(57) ABSTRACT

The present disclosure relates to an organic compound having the following structure, and an organic light emitting diode (OLED) and an organic light emitting device including the organic compound. The organic compound can be a bipolar compound having a p-type moiety and an n-type moiety and has high energy level and proper energy bandgap for an emissive layer of the OLED. As the organic compound is applied into the emissive layer, the OLED can maximize its luminous properties as holes and electrons are recombined uniformly over the whole area in an emitting material layer (EML).

6 Claims, 13 Drawing Sheets

(51) Int. Cl.
  *C07D 495/20* (2006.01)
  *C09K 11/06* (2006.01)
  *H10K 50/11* (2023.01)

(52) U.S. Cl.
  CPC .......... *C09K 11/06* (2013.01); *H10K 85/6572* (2023.02); *C09K 2211/1018* (2013.01); *H10K 50/11* (2023.02)

(58) Field of Classification Search
  CPC ............ C09K 11/06; C09K 2211/1018; C09K 2211/1029; C09K 2211/1044; C09K 2211/187; C07F 9/587; C07F 15/06
  See application file for complete search history.

(56) References Cited

U.S. PATENT DOCUMENTS

| | | |
|---|---|---|
| 2017/0012219 A1 | 1/2017 | Parham et al. |
| 2017/0141327 A1 | 6/2017 | Parham et al. |

FOREIGN PATENT DOCUMENTS

| | | |
|---|---|---|
| KR | 10-2015-0083917 A | 7/2015 |
| KR | 10-2019-0003332 A | 1/2019 |
| KR | 10-2019-0083236 A | 7/2019 |

OTHER PUBLICATIONS

Li et al.. "Design Sythesis of the Thermal Activity Delayed Fluorescent Material and its Application on OLEDs", Chinese Science Bulletin, vol. 60, Dec. 31, 2015, pp. 1-16 (17 pages total).

Peng et al. "Research Progress on Materials for Organic Light-emitting Diodes (OLEDS)". Material Reports, Wuhan Jingce Electronic Technology Co, vol. 29, No. 3, Mar. 31, 2015, pp. 41-56, with English abstract.

Zhang, J., et al., "Multiphosphine-Oxide Hosts for Ultralow-Voltage-Driven True-Blue Thermally Activated Delayed Fluorescence Diodes with External Quantum Efficiency beyond 20%," Adv. Mater., 2015, pp. 1-7.

\* cited by examiner

ORGANIC COMPOUND, ORGANIC LIGHT EMITTING DIODE AND ORGANIC LIGHT EMITTING DEVICE INCLUDING THE ORGANIC COMPOUND

CROSS-REFERENCE TO RELATED APPLICATIONS

This application is a Divisional application of U.S. patent application Ser. No. 16/930,719, filed on Jul. 16, 2020, which claims priority under 35 U.S.C. § 119(a) to Korean Patent Application No. 10-2019-0086572, filed in the Republic of Korea on Jul. 17, 2019, all of which are hereby expressly incorporated by reference into the present application.

BACKGROUND

Technical Field

The present disclosure relates to an organic compound, and more specifically, to an organic compound having enhanced luminous properties, an organic light emitting diode and an organic light emitting device including the organic compound.

Discussion of the Related Art

As display devices have become larger, there exists a need for a flat display device with a lower space requirement. Among the flat display devices used widely at present, display having organic light emitting diodes (OLEDs) are rapidly replacing liquid crystal display devices (LCDs).

The OLED can be formed as a thin film having a thickness less than 2000 Å and can be implement unidirectional or bidirectional images as electrode configurations. In addition, OLEDs can be formed on a flexible transparent substrate such as a plastic substrate so that OLED can implement a flexible or foldable display with ease. Moreover, the OLED can be driven at a lower voltage of 10 V or less. Besides, the OLED has relatively lower power consumption for driving compared to plasma display panels and inorganic electroluminescent devices, and the color purity of the OLED is very high. Particularly, the OLED can implement red, green and blue colors, thus it has attracted a lot of attention as a light emitting device.

Conventional fluorescent materials in which only singlet excitons involved in the luminescence process have low luminous efficiency. The phosphorescent materials in which triplet excitons as well as singlet excitons involved in the luminescence process have relatively high luminous efficiency. However, the metal complex, representative phosphorescent materials, has too short luminous lifetime to be applicable to commercial devices. Particularly, the luminous materials for implementing blue emission have deteriorated luminous properties and luminous lifetime.

SUMMARY

Accordingly, embodiments of the present disclosure are directed to an organic compound and an OLED and an organic light emitting device including the organic compound that substantially obviates one or more of the problems due to the limitations and disadvantages of the related art.

An object of the present disclosure is to provide an organic compound having high excited triplet energy level as well as bipolar properties, an OLED and an organic light emitting device into which the organic compound is applied.

Another object of the present disclosure is to provide an organic compound that has excellent thermal stability as well as high affinity to electrons, an OLED and an organic light emitting device having the compound.

Additional features and aspects will be set forth in the description that follows, and in part will be apparent from the description, or can be learned by practice of the inventive concepts provided herein. Other features and aspects of the inventive concept can be realized and attained by the structure particularly pointed out in the written description, or derivable therefrom, and the claims hereof as well as the appended drawings.

To achieve these and other aspects of the inventive concepts, as embodied and broadly described, the present disclosure provides an organic compound having the following structure of

[Chemical Formula 1]

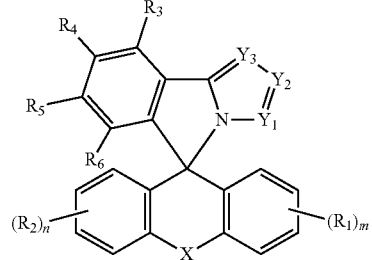

wherein each of R1 and R2 is independently hydrogen, an unsubstituted or substituted C1-C20 alkyl group, or an unsubstituted or substituted hetero aromatic group having one to three fused hetero aromatic moieties, wherein at least one of R1 and R2 is the hetero aromatic group; each of m and n is the number of substituent and is independently an integer between 0 (zero) to 4; each of R3 to R6 is independently hydrogen, an unsubstituted or substituted C1-C20 alkyl group, an unsubstituted or substituted C1-C20 alkoxy group, an unsubstituted or substituted C6-C30 aromatic group or an unsubstituted or substituted C3-C30 hetero aromatic group; X is O or S; and each of Y1 to Y3 is independently N or CR7, wherein R7 is hydrogen, an unsubstituted or substituted C1-C20 alkyl group, an unsubstituted or substituted C1-C20 alkoxy group, an unsubstituted or substituted C6-C30 aromatic group or an unsubstituted or substituted C3-C30 hetero aromatic group, wherein at least one of Y1 to Y3 is N.

In another aspect, the present disclosure provides an OLED that comprises a first electrode; a second electrode facing the first electrode; and at least one emitting unit disposed between the first and second electrodes, wherein the at least one emitting unit comprises the organic compound.

For example, at least one of an ETL, a HBL, an EML and a CGL can comprise the organic compound.

As an example, the EML can comprise the organic compound as a host, and in this case the EML can further comprise at least one dopant such as delayed fluorescent material, fluorescent material and phosphorescent material.

In still another aspect, the present disclosure provides an organic light emitting device, such as an organic light emitting display device and an organic light emitting illumination device that comprises a substrate and an OLED disposed over the substrate, as described above.

It is to be understood that both the foregoing general description and the following detailed description are exemplary and explanatory and are intended to provide further explanation of the inventive concepts as claimed.

BRIEF DESCRIPTION OF THE DRAWINGS

The accompanying drawings, which are included to provide a further understanding of the disclosure, are incorporated in and constitute a part of this application, illustrate embodiments of the disclosure and together with the description serve to explain principles of the disclosure.

DETAILED DESCRIPTION OF THE EMBODIMENTS

Figure 1:
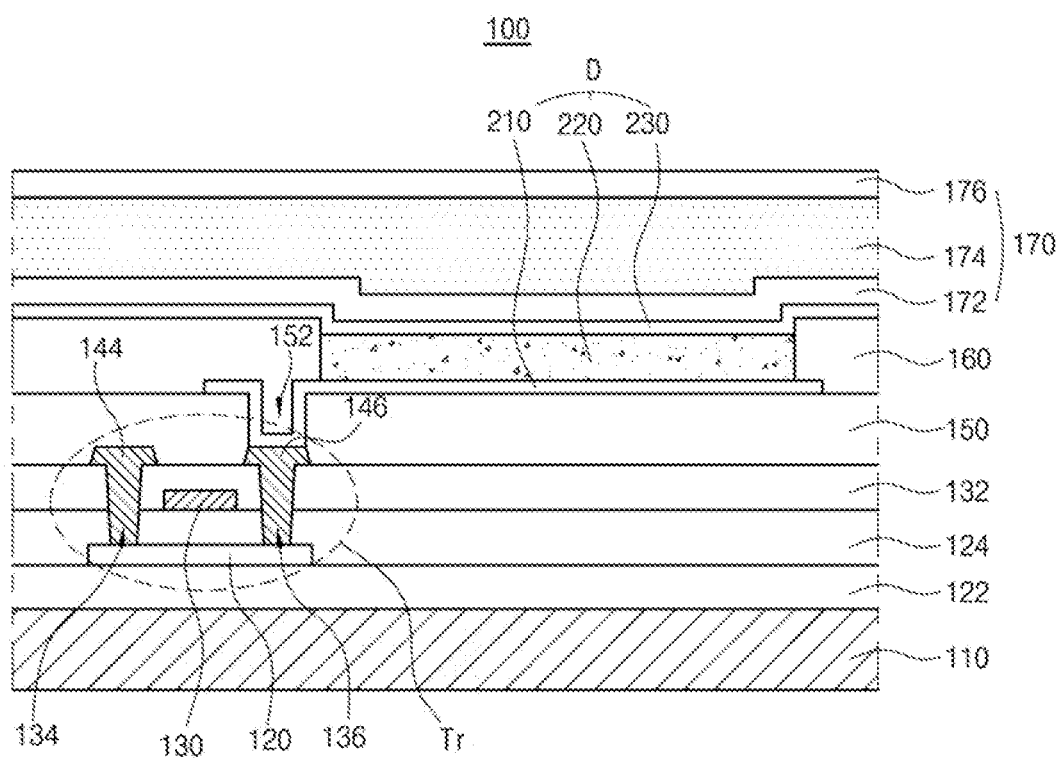
FIG. 1 is a schematic cross-sectional view illustrating an organic light emitting display device in accordance with an aspect of the present disclosure.

Reference and discussions will now be made below in detail to aspects, embodiments and examples of the disclosure, some examples of which are illustrated in the accompanying drawings.

[Organic Compound]

An organic compound applied to an organic light emitting diode (OLED) should have excellent luminous properties, high affinity to charges and maintain stable properties to in driving the OLED. Particularly, the luminous materials applied to the diode is the most important factor determining the luminous efficiency of the OLED. The luminous material should have high quantum efficiency, large mobility for charges and adequate energy levels with regard to other materials applied in the same or adjacent layers. An organic compound in accordance with the present disclosure can have the following structure of Chemical Formula 1:

[Chemical Formula 1]

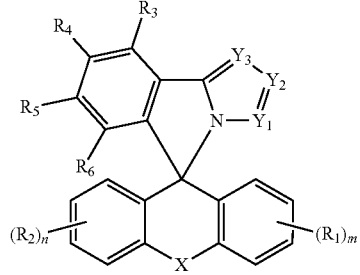

In Chemical Formula 1, each of $R_1$ and $R_2$ is independently hydrogen, an unsubstituted or substituted $C_1$-$C_{20}$ alkyl group, or an unsubstituted or substituted hetero aromatic group having one to three fused hetero aromatic moieties, wherein at least one of $R_1$ and $R_2$ is the hetero aromatic group; each of m and n is the number of substituent and is independently an integer between 0 (zero) to 4; each of $R_3$ to $R_6$ is independently hydrogen, an unsubstituted or substituted $C_1$-$C_{20}$ alkyl group, an unsubstituted or substituted $C_1$-$C_{20}$ alkoxy group, an unsubstituted or substituted $C_6$-$C_{30}$ aromatic group or an unsubstituted or substituted $C_3$-$C_{30}$ hetero aromatic group; X is O or S; and each of $Y_1$ to $Y_3$ is independently N or $CR_7$, wherein $R_7$ is hydrogen, an unsubstituted or substituted $C_1$-$C_{20}$ alkyl group, an unsubstituted or substituted $C_1$-$C_{20}$ alkoxy group, an unsubstituted or substituted $C_6$-$C_{30}$ aromatic group or an unsubstituted or substituted $C_3$-$C_{30}$ hetero aromatic group, wherein at least one of $Y_1$ to $Y3$ is N.

As used herein, the term "unsubstituted" means that hydrogen is linked, and in this case, hydrogen comprises protium, deuterium and tritium.

As used herein, the substituent in the term "substituted" comprises, but is not limited to, unsubstituted or halogen-substituted $C_1$-$C_{20}$ alkyl, unsubstituted or halogen-substituted $C_1$-$C_{20}$ alkoxy, halogen, cyano, —$CF_3$, a hydroxyl group, a carboxylic group, a carbonyl group, an amino group, a $C_1$-$C_{10}$ alkyl amino group, a $C_6$-$C_{30}$ aryl amino group, a $C_3$-$C_{30}$ hetero aryl amino group, a $C_6$-$C_{30}$ aryl group, a $C_3$-$C_{30}$ hetero aryl group, a nitro group, a hydrazyl group, a sulfonate group, a $C_1$-$C_{20}$ alkyl silyl group, a $C_6$-$C_{30}$ aryl silyl group and a $C_3$-$C_{30}$ hetero aryl silyl group.

As used herein, the term "hetero" in such as "a hetero aromatic ring", "a hetero cycloalkylene group", "a hetero arylene group", "a hetero aryl alkylene group", "a hetero aryl oxylene group", "a hetero cycloalkyl group", "a hetero aryl group", "a hetero aryl alkyl group", "a hetero aryloxyl group", "a hetero aryl amino group" means that at least one carbon atom, for example 1-5 carbons atoms, constituting an aromatic ring or an alicyclic ring is substituted with at least one hetero atom selected from the group consisting of N, O, S, P and combination thereof.

The organic compound having the structure of Chemical Formula 1 has one moiety having a rigid spiro structure including at least two nitrogen atoms and a hetero aromatic moiety having at least one fused hetero aromatic ring connected to the spiro moiety. More particularly, the organic compound includes a moiety (spiro moiety) in which fused hetero aromatic ring having at least one, preferably at least two nitrogen atoms forms a spiro structure with a xanthene or thioxanthene ring and a hetero aromatic group (moiety) having one to three fused hetero aromatic moieties linked directly or indirectly to the xanthene or thioxanthene ring of the spiro moiety.

The spiro moiety includes a 5-membered ring fused with an iso-indolo moiety. As the numbers and locations of the nitrogen atoms among $Y_1$ to $Y_3$, the 5-membered ring can have a pyrazole, imidazole, triazole, or tetrazole structure. Since the spiro moiety including the 5-membered ring has excellent affinity to electrons, the spiro moiety can have an n-type property that induces electrons injection and mobility.

The hetero aromatic moiety having one to three fused hetero aromatic rings has excellent binding affinity to holes, it can have a p-type property that induces holes injection and mobility. Therefore, the organic compound has a bipolar property. In one exemplary aspect, the $C_6$-$C_{30}$ aromatic group in each of $R_1$ to $R_7$ can comprise a $C_6$-$C_{30}$ aryl group, a $C_7$-$C_{30}$ aryl alkyl group, a $C_6$-$C_{30}$ aryloxyl group and a $C_3$-$C_{30}$ aryl amino group. The $C_3$-$C_{30}$ hetero aromatic group in each of $R_1$ to $R_6$ can comprise a $C_3$-$C_{30}$ hetero aryl group, a $C_4$-$C_{30}$ hetero aryl alkyl group, a $C_3$-$C_{30}$ hetero aryloxyl group and a $C_3$-$C_{30}$ hetero aryl amino group.

In one exemplary aspect, the $C_6$-$C_{10}$ aryl group in each of $R_1$ to $R_7$ can comprise independently, but is not limited to, an unfused or fused aryl group such as phenyl, biphenyl, terphenyl, naphthyl, anthracenyl, pentalenyl, indenyl, indeno-indenyl, heptalenyl, biphenylenyl, indacenyl, phenalenyl, phenanthrenyl, benzo-phenanthrenyl, dibenzo-phenanthrenyl, azulenyl, pyrenyl, fluoranthenyl, triphenylenyl, chrysenyl, tetraphenylenyl, tetracenyl, pleiadenyl, picenyl, pentaphenylenyl, pentacenyl, fluorenyl, indeno-fluorenyl and spiro-fluorenyl.

In another exemplary aspect, the $C_3$-$C_{30}$ hetero aryl group in each of $R_1$ to $R_7$ can comprise independently, but is not limited to, an unfused or fused hetero aryl group such as pyrrolyl, pyridinyl, pyrimidinyl, pyrazinyl, pyridazinyl, triazinyl, tetrazinyl, imidazolyl, pyrazolyl, indolyl, iso-indolyl, indazolyl, indolizinyl, pyrrolizinyl, carbazolyl, benzo-carbazolyl, dibenzo-carbazolyl, indolo-carbazolyl, indeno-carbazolyl, benzo-furo-carbazolyl, benzo-thieno-carbazolyl, carbolinyl, quinolinyl, iso-quinolinyl, phthlazinyl, quinoxalinyl, cinnolinyl, quinazolinyl, quinolizinyl, purinyl, benzo-quinolinyl, benzo-iso-quinolinyl, benzo-quinazolinyl, benzo-quinoxalinyl, acridinyl, phenazinyl, phenoxazinyl, phenothiazinyl, phenanthrolinyl, perimidinyl, phenanthridinyl, pteridinyl, naphthyridinyl, furanyl, pyranyl, oxazinyl, oxazolyl, oxadiazolyl, triazolyl, dioxinyl, benzo-furanyl, dibenzo-furanyl, thiopyranyl, xanthenyl, chromenyl, iso-chromenyl, thioazinyl, thiophenyl, benzo-thiophenyl, dibenzo-thiophenyl, difuro-pyrazinyl, benzo-furo-dibenzo-furanyl, benzothieno-benzo-thiophenyl, benzothieno-dibenzo-thiophenyl, benzothieno-benzo-furanyl, benzothieno-dibenzo-furanyl, xanthne-linked spiro acridinyl, dihydroacridinyl substituted with at least one $C_1$-$C_{10}$ alkyl and N-substituted spiro fluorenyl.

As an example, each of the aromatic group and the hetero aromatic group in each of $R_1$ to $R_7$ can have independently one to three aromatic or hetero aromatic rings. When the number of the aromatic or the hetero aromatic ring in each of $R_1$ to $R_7$ becomes large, the conjugated structure within the whole molecule is too long, and therefore the organic compound can have excessively reduced energy bandgap. With regard charge injection and transfer property, each of the aromatic group and the hetero aromatic group can comprise a 5-membered ring, a 6-membered ring or 7-membered ring. As an example, each of the aryl group and the hetero aryl group in each of $R_1$ to $R_7$ can comprise independently, but is not limited to, phenyl, biphenyl, naphthyl, anthracenyl, pyrrolyl, triazinlyl, imidazolyl, pyrazolyl, pyridinyl, pyrazinyl, pyrimidinyl, pyridazinlyl, furanyl, benzo-furanyl, dibenzo-furanyl, thiophenyl, benzo-thiophenyl, dibenzo-thiophenyl, carbazolyl, acridinyl, carobolinyl, phenazinyl, phenoxazinyl and/or phenothiazinyl.

The hetero aromatic group in $R_1$ and/or $R_2$ can have unsubstituted or substituted one to three fused hetero aromatic moieties. In one exemplary aspect, the fused hetero aromatic moiety can contain nitrogen, oxygen and/or sulfur atoms as a nuclear atom of the ring. For example, the fused hetero aromatic moiety can be selected from, but is not limited to, carbazolyl, acridinyl, dibenzo-furanyl and dibenzo-thiophenyl.

In another exemplary aspect, the fused hetero aromatic moiety is further fused with other aromatic or hetero aromatic rings to the fused aromatic rings. In this case, the other aromatic or hetero aromatic ring fused further to the fused aromatic ring can be an aromatic ring such as a benzene ring, a naphthyl ring and/or an indeno ring or a fused hetero aromatic ring such as a benzo-furo ring, a benzo-thieno ring and an indolo ring. For example, the above fused hetero aromatic moiety can be combined to other aromatic or hetero aromatic moiety to for benzo-carbazolyl, dibenzo-carbazolyl, indeno-carbazolyl, benzo-furo-carbazolyl, benzo-thieno-carbazolyl, indolo-carbazolyl, benzo-acridinyl, dibenzo-acridinyl, indeno-acridinyl, benzo-furo-acridinyl, benzo-thieno-acridinyl, indeno-dibenzo-furanyl, benzo-furo-benzo-furanyl, benzo-thieno-benzo-furanyl, indolo-dibenzo-furanyl, indeno-dibenzo-thiophenyl, benzo-furo-dibenzo-thiophenyl, benzo-thieno-benzo-furanyl, indolo-dibenzo-furanyl, indeno-dibenzo-thiophenyl, benzo-furo-dibenzo-thiophenyl, benzo-thieno-dibenzo-furanyl and indolo-dibenzo-thiophenyl.

Alternatively, the fused hetero aromatic moiety can for a spiro structure. The spiro structure is not specific structure and comprise, but is not limited to, a spiro fluorene structure and a spiro benzo-fluorene structure each of which is unsubstituted or substituted with at least one of a $C_1$-$C_{20}$ alkyl group, a $C_6$-$C_{30}$ aromatic group and a $C_6$-$C_{30}$ aromatic amino group. For example, the fused hetero aromatic moiety can form spirofluoreno-carbazolyl and spirofluoreno-acridinyl.

The organic compound having the structure of Chemical Formula 1 has a rigid chemical conformation, and a spiro moiety including a 5-member ring in which at least one, preferably at least two nitrogen atoms are incorporated and a hetero aromatic moiety including one to three fused hetero aromatic rings and linked to the spiro moiety.

The spiro moiety has an n-type property while the hetero aromatic moiety has a p-type property, thus the organic compound has bipolar properties. Since the carbon atom in the spiro moiety (electron acceptor moiety) having the n-type property has $sp^3$ or $sp^2$ hybrid orbital and is connected to the hetero aromatic moiety having excellent hole affinity, thus the organic compound has high excited triplet energy level and excellent thermal stability.

Figure 4:
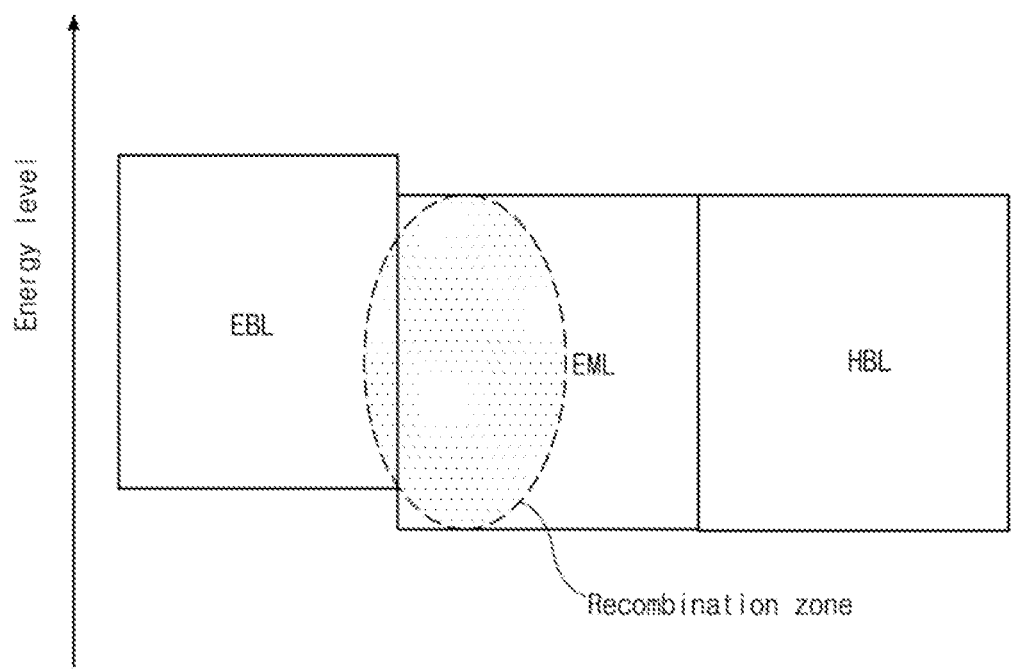
FIG. 4 is a schematic diagram illustrating a recombination zone among holes and electrons injected into the EML when using the organic compound of the present disclosure.

As the organic compound is introduce in an emissive layer, for example an EML, holes and electrons can be injected into the EML in balance, and therefore, the recombination zone among holes and electrons are disposed uniformly on the whole area of the EML (see, FIG. 4). Accordingly, the EML can maximize its luminous efficiency.

In addition, the organic compound has relatively wide energy bandgap between the HOMO (highest occupied molecular orbital) and the LUMO (lowest unoccupied molecular orbital) energy levels and high excited triplet energy level compared to dopants in the EML. As the organic compound is used as the host in the EML, the exciton energy is efficiently transferred from the organic compound to the dopant, exciton quenching due to interactions triplet/singlet excitons of the host or the dopant and adjacently located hole (or electron)-polarons.

The organic compound can transfer exciton energies to the dopant without energy loss in luminescence process, thus it can accomplish very high luminous efficiency. As an example, when the EML comprises the organic compounds as the host and the dopant such as the delayed fluorescent material and/or fluorescent material with narrow FWHM (full-width at half maximum), the OLED can improve its color purity and lower its driving voltage and power consumption in luminescent wavelengths. As the driving voltage decrease, there exists less stress to the OLED, the OLED can improve its luminous efficiency and increase its luminous lifetime. For example, the EML includes the organic compound as the host, another luminous material having delayed fluorescent property and optionally a third luminous material as the fluorescent material with narrow FWHM, it is possible to implement an OLED and organic light emitting device that has excellent luminous efficiency and luminous lifetime and improved color purity.

In addition, the organic compound has excellent electron affinity and deep HOMO energy level, thus the organic compound can be used in at least one of an ETL, an HBL and an N-CGL between emitting units.

In one exemplary aspect, the organic compound having the structure of Chemical Formula 1 can have, but is not limited to, an excited singlet energy level $S_1$ equal to or more than about 3.2 eV and an excited triplet energy level $T_1$ equal to or more than about 2.8 eV. Also, the organic compound can have, but is not limited to, the HOMO energy level between about −5.3 eV and about −6.3 eV, preferably between about −5.7 eV and about −6.1 eV, the LUMO energy level between about −2.0 eV and about −3.0 eV, preferably about −2.1 eV and about −2.8 eV, and the energy level bandgap between the HOMO energy level and the LUMO energy level between about 3.0 eV and about 4.5 eV, preferably about 3.4 eV and about 4.0 eV.

In one exemplary aspect, the organic compound can have one or two hetero aromatic groups linked to the spiro moiety. Such an organic compound can have the following structure of Chemical Formula 2:

[Chemical Formula 2]

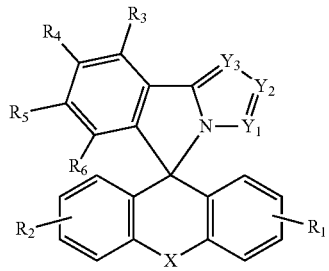

In Chemical Formula 2, each of $R_1$ to $R_6$, X and $Y_1$ to $Y_3$ is identical defined in Chemical Formula 1.

In another exemplary aspect, the 5-membered ring fused to the indolo-moiety of the spiro moiety can have a pyrazole structure. In this case, the fused hetero aromatic ring linked by spiro structure to the xanthene or the thioxanthene ring of the spiro moiety can from an isoindolo-pyrazole ring. Such an organic compound can have the following structure of Chemical Formula 3:

[Chemical Formula 3]

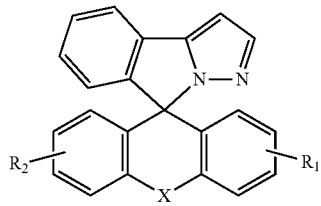

In Chemical Formula 3, each of $R_1$, $R_2$ and X is identical defined in Chemical Formula 1.

The spiro moiety of the organic compound having the structure of Chemical Formulae 3 comprises the isoindolo-pyrazole ring, thus allows the molecule to improve its n-type property. Also, the organic compound has the fused hetero aromatic moiety having the p-type property, thus the organic compound has a bipolar property. The carbon atom in the spiro moiety includes $sp^3$ or $sp^2$ hybrid orbital which enables the organic compound to have excellent thermal stability and high excited triplet energy level. Since the organic compound has wide energy level bandgap between the HOMO energy level and the LUMO energy level and has relatively deep HOMO energy level, it can be used as the host in the EML or charge transfer or control material in at least one of the ETL, HBL and N-CGL. As an example, when the organic compound having the structure of Chemical Formulae 2 and 3 is used with dopants, the exciton energy can be efficiently to the dopants without any energy loss in luminescence process.

In one exemplary aspect, $R_1$ in Chemical Formulae 1 to 3 can be the hetero aromatic group. In this case, the spiro moiety including X can comprise anyone having the following structure of Chemical Formula 4:

[Compound Formula 4]

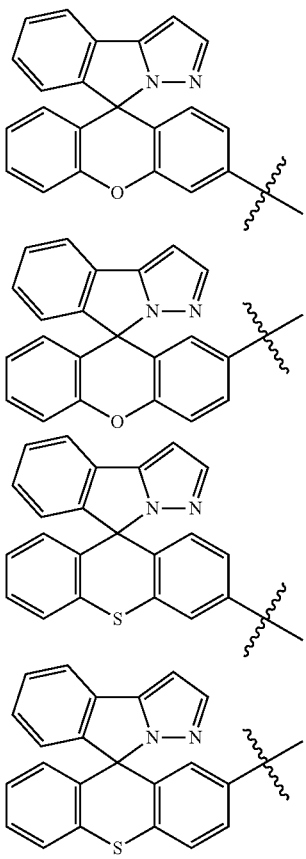

In Chemical Formula 4, the wavy portion indicates a linking site to $R_1$.

In another exemplary aspect, the fused hetero aromatic moiety can have one to three unsubstituted or substituted carbazolyl moieties and/or acridinyl moieties. In this case, $R_1$ as the fused hetero aromatic moiety can comprise anyone having the following structure of Chemical Formula 5:

[Chemical Formula 5]

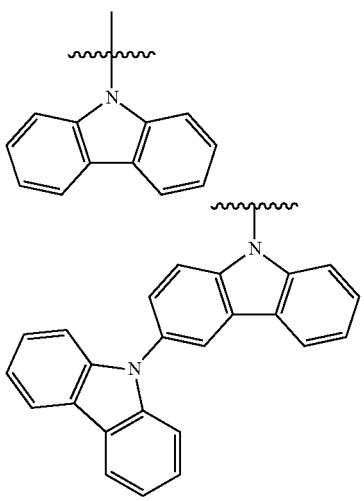

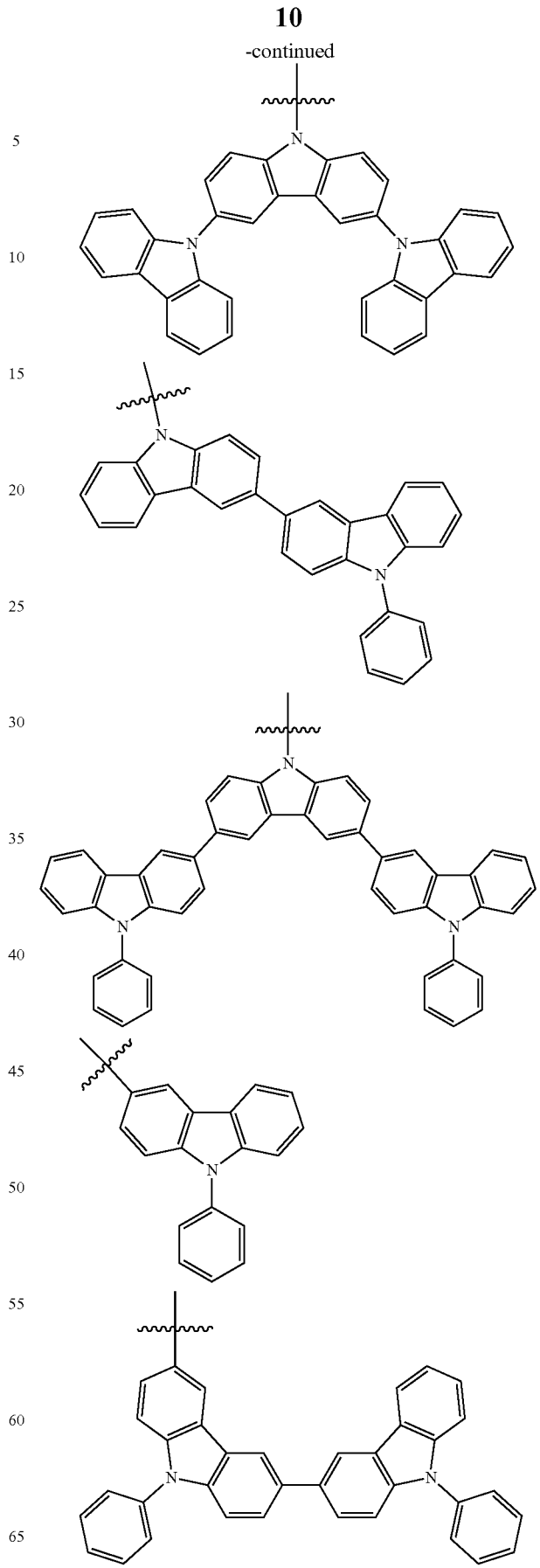

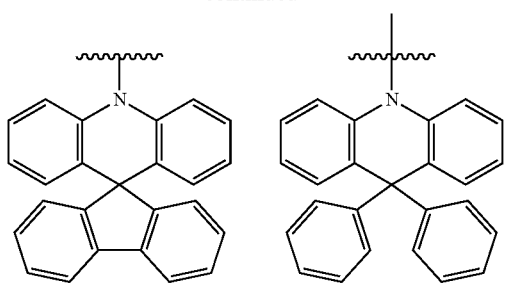
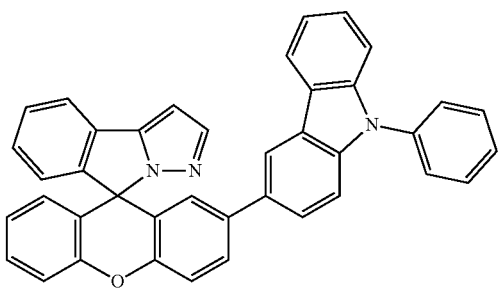
In Chemical Formula 5, the wavy portion indicates a linking site to a spiro moiety including X.
More particularly, the organic compound having the structure of Chemical Formulae 1 to 3 can comprise anyone having the following structure of Chemical Formula 6:
[Chemical Formula 6]
1
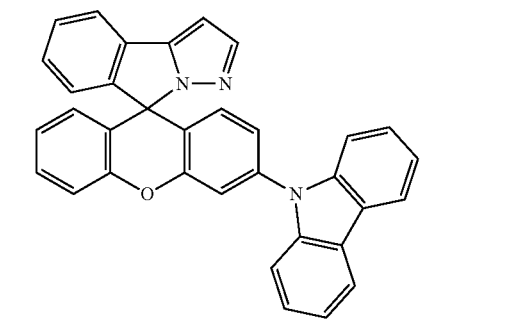
2
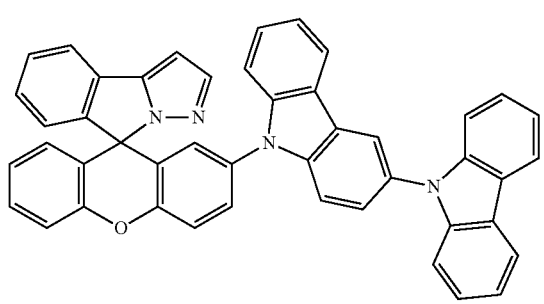
3
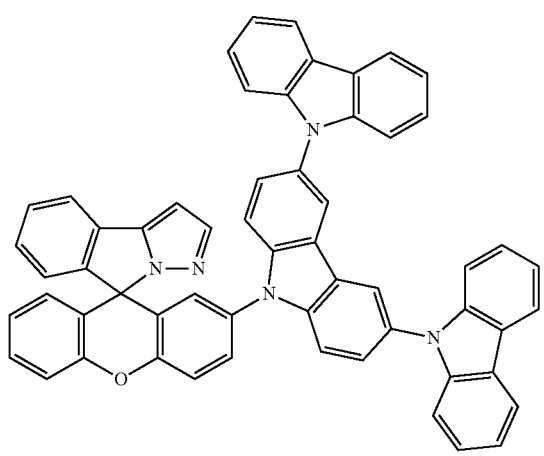
4
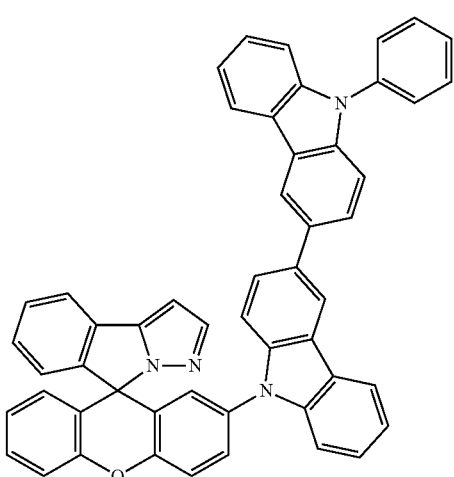
5
6
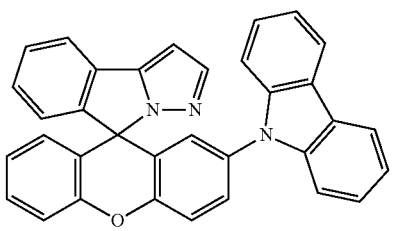
7
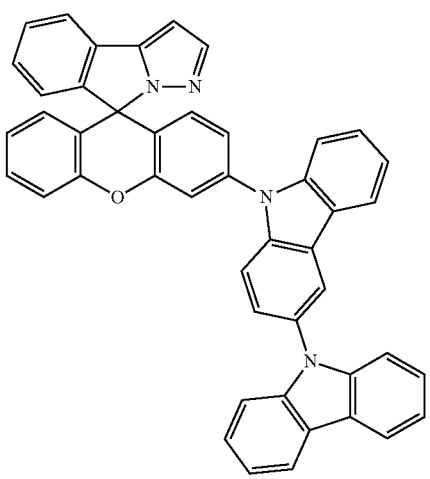

8
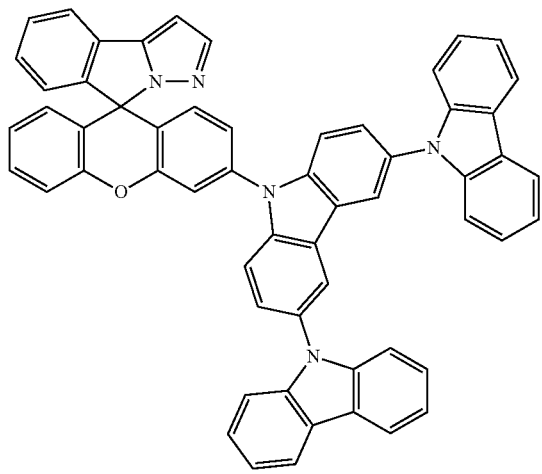
9
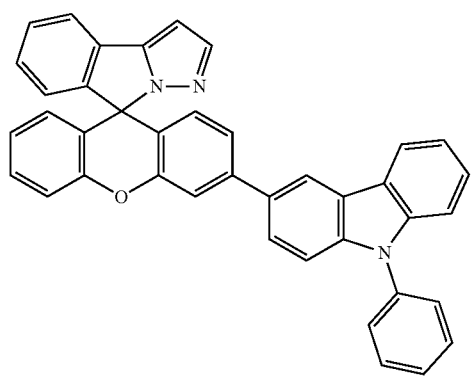
10
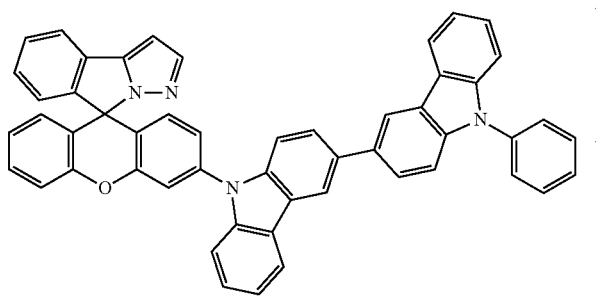
11
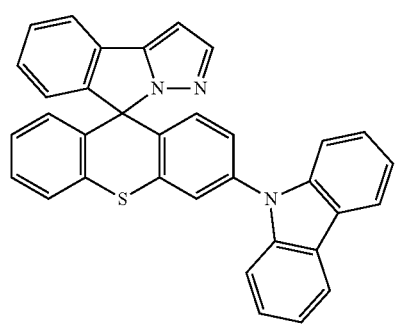
12
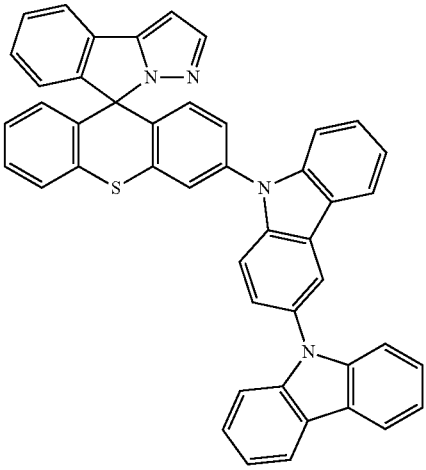
13
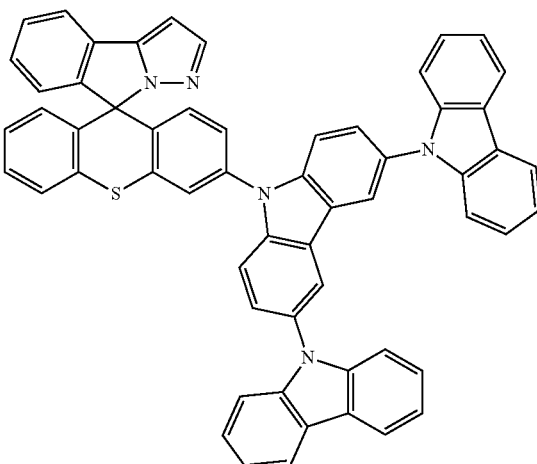
14
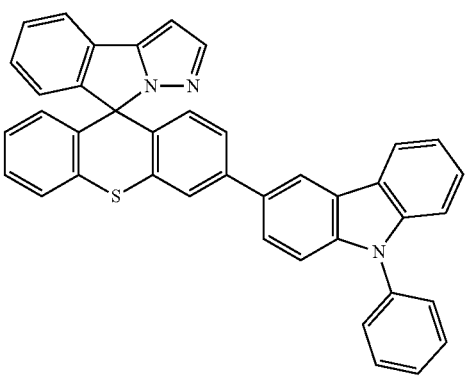
15
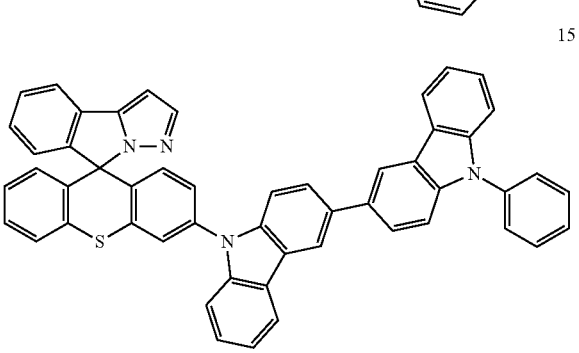

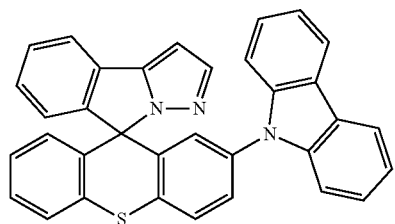

16

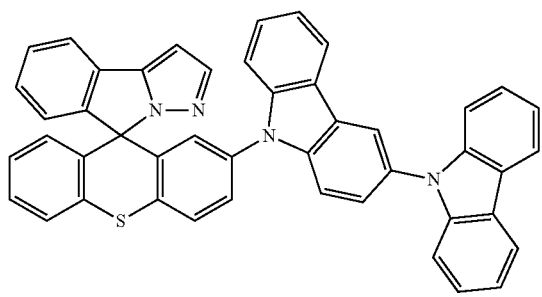

18

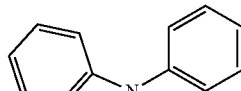

19

20

[Organic Light Emitting Device and OLED]

The organic compound having the structure of Chemical Formulae 1 to 3 and 6 has excellent thermal stability and enhanced luminous properties. It is possible to implement an OLED and an organic light emitting device that lowers their driving voltage and improves their luminous efficiency by applying the organic compound into an emissive layer of the OLED. The OLED of the present disclosure can be applied to an organic light emitting device such as an organic light emitting display device or an organic light emitting illumination device. An organic light emitting display device including the OLED will be explained now.

FIG. 1 is a schematic cross-sectional view of an organic light emitting display device 100 in accordance with an aspect of the present disclosure. All components of the organic light emitting display device in accordance with all aspects of the present disclosure are operatively coupled and configured.

As illustrated in FIG. 1, the organic light emitting display device 100 includes a substrate 110, a thin-film transistor Tr on the substrate 110, and an organic light emitting diode (OLED) D connected to the thin film transistor Tr.

The substrate 110 can include, but is not limited to, glass, thin flexible material and/or polymer plastics. For example, the flexible material can be selected from the group, but is not limited to, polyimide (PI), polyethersulfone (PES), polyethylenenaphthalate (PEN), polyethylene terephthalate (PET), polycarbonate (PC) and combination thereof. The substrate 110, over which the thin film transistor Tr and the OLED D are arranged, form an array substrate.

A buffer layer 122 can be disposed over the substrate 110, and the thin film transistor Tr is disposed over the buffer layer 122. The buffer layer 122 can be omitted.

A semiconductor layer 120 is disposed over the buffer layer 122. In one exemplary aspect, the semiconductor layer 120 can include, but is not limited to, oxide semiconductor materials. In this case, a light-shield pattern can be disposed under the semiconductor layer 120, and the light-shield pattern can prevent light from being incident toward the semiconductor layer 120, and thereby, preventing the semiconductor layer 120 from being deteriorated by the light. Alternatively, the semiconductor layer 120 can include, but is not limited to, polycrystalline silicon. In this case, opposite edges of the semiconductor layer 120 can be doped with impurities.

A gate insulating layer 124 formed of an insulating material is disposed on the semiconductor layer 120. The gate insulating layer 124 can include, but is not limited to, an inorganic insulating material such as silicon oxide ($SiO_x$) or silicon nitride ($SiN_x$).

A gate electrode 130 made of a conductive material such as a metal is disposed over the gate insulating layer 124 so as to correspond to a center of the semiconductor layer 120. While the gate insulating layer 124 is disposed over a whole area of the substrate 110 in FIG. 1, the gate insulating layer 124 can be patterned identically as the gate electrode 130.

An interlayer insulating layer 132 formed of an insulating material is disposed on the gate electrode 130 with covering over an entire surface of the substrate 110. The interlayer insulating layer 132 can include, but is not limited to, an inorganic insulating material such as silicon oxide ($SiO_x$) or silicon nitride ($SiN_x$), or an organic insulating material such as benzocyclobutene or photo-acryl.

The interlayer insulating layer 132 has first and second semiconductor layer contact holes 134 and 136 that expose both sides of the semiconductor layer 120. The first and second semiconductor layer contact holes 134 and 136 are disposed over opposite sides of the gate electrode 130 with spacing apart from the gate electrode 130. The first and second semiconductor layer contact holes 134 and 136 are formed within the gate insulating layer 124 in FIG. 1.

Alternatively, the first and second semiconductor layer contact holes 134 and 136 are formed only within the interlayer insulating layer 132 when the gate insulating layer 124 is patterned identically as the gate electrode 130.

A source electrode 144 and a drain electrode 146, which are formed of conductive material such as a metal, are disposed on the interlayer insulating layer 132. The source electrode 144 and the drain electrode 146 are spaced apart from each other with respect to the gate electrode 130, and contact both sides of the semiconductor layer 120 through the first and second semiconductor layer contact holes 134 and 136, respectively.

The semiconductor layer 120, the gate electrode 130, the source electrode 144 and the drain electrode 146 constitute the thin film transistor Tr, which acts as a driving element. The thin film transistor Tr in FIG. 1 has a coplanar structure in which the gate electrode 130, the source electrode 144 and the drain electrode 146 are disposed over the semiconductor layer 120. Alternatively, the thin film transistor Tr can have an inverted staggered structure in which a gate electrode is disposed under a semiconductor layer and a source and drain electrodes are disposed over the semiconductor layer. In this case, the semiconductor layer can comprise amorphous silicon.

A gate line and a data line, which cross each other to define a pixel region, and a switching element, which is connected to the gate line and the data line, can be further formed in the pixel region of FIG. 1. The switching element is connected to the thin film transistor Tr, which is a driving element. Besides, a power line is spaced apart in parallel from the gate line or the data line, and the thin film transistor Tr can further include a storage capacitor configured to constantly keep a voltage of the gate electrode for one frame.

In addition, the organic light emitting display device 100 can include a color filter that comprises dyes or pigments for transmitting specific wavelength light of light emitted from the OLED D. For example, the color filter can transmit light of specific wavelength such as red (R), green (G), blue (B) and/or white (W). Each of red, green, and blue color filter can be formed separately in each pixel region. In this case, the organic light emitting display device 100 can implement full-color through the color filter.

For example, when the organic light emitting display device 100 is a bottom-emission type, the color filter can be disposed on the interlayer insulating layer 132 with corresponding to the OLED D. Alternatively, when the organic light emitting display device 100 is a top-emission type, the color filter can be disposed over the OLED D, for example, a second electrode 230.

A passivation layer 150 is disposed on the source and drain electrodes 144 and 146 over the whole substrate 110. The passivation layer 150 has a flat top surface and a drain contact hole 152 that exposes the drain electrode 146 of the thin film transistor Tr. While the drain contact hole 152 is disposed on the second semiconductor layer contact hole 136, it can be spaced apart from the second semiconductor layer contact hole 136.

The OLED D includes a first electrode 210 that is disposed on the passivation layer 150 and connected to the drain electrode 146 of the thin film transistor Tr. The OLED D further includes an emissive layer 220 including at least one emitting unit and a second electrode 230 each of which is disposed sequentially on the first electrode 210.

The first electrode 210 is disposed in each pixel region. The first electrode 210 can be an anode and include a conductive material having a relatively high work function value. For example, the first electrode 210 can include, but is not limited to, a transparent conductive material such as indium tin oxide (ITO), indium zinc oxide (IZO), indium tin zinc oxide (ITZO), tin oxide (SnO), zinc oxide (ZnO), indium cerium oxide (ICO), aluminum doped zinc oxide (AZO), and the like.

In one exemplary aspect, when the organic light emitting display device 100 is a top-emission type, a reflective electrode or a reflective layer can be disposed under the first electrode 210. For example, the reflective electrode or the reflective layer can include, but are not limited to, aluminum-palladium-copper (APC) alloy.

In addition, a bank layer 160 is disposed on the passivation layer 150 in order to cover edges of the first electrode 210. The bank layer 160 exposes a center of the first electrode 210.

An emissive layer 220 is disposed on the first electrode 210. In one exemplary aspect, the emissive layer 220 can have a mono-layered structure of an emitting material layer (EML). Alternatively, the emissive layer 220 can have a multiple-layered structure of a hole injection layer (HIL), a hole transport layer (HTL), an electron blocking layer (EBL), an EML, a hole blocking layer (HBL), an electron transport layer (ETL) and/or an electron injection layer (EIL) (see, FIGS. 2, 7, 9, 11 and 13). In one aspect, the OLED D can have one emitting unit. Alternatively, the OLED D can have multiple emitting units to form a tandem structure.

The emissive layer 220 comprises anyone having the structure of Chemical Formulae 1 to 3 and 6. As an example, the organic compound having the structure of Chemical Formulae 1 to 3 and 6 can be applied into the host in the EML, or into the ETL, the HBL and the N-CGL.

The second electrode 230 is disposed over the substrate 110 above which the emissive layer 220 is disposed. The second electrode 230 can be disposed over a whole display area and can include a conductive material with a relatively low work function value compared to the first electrode 210. The second electrode 230 can be a cathode. For example, the second electrode 230 can include, but is not limited to, aluminum (Al), magnesium (Mg), calcium (Ca), silver (Ag), alloy thereof or combination thereof such as aluminum-magnesium alloy (Al—Mg).

In addition, an encapsulation film 170 can be disposed over the second electrode 230 in order to prevent outer moisture from penetrating into the OLED D. The encapsulation film 170 can have, but is not limited to, a laminated structure of a first inorganic insulating film 172, an organic insulating film 174 and a second inorganic insulating film 176, Moreover, a polarizer can be attached to the encapsulation film 170 in order to decrease external light reflection. For example, the polarizer can be a circular polarizer. In addition, a cover window can be attached to the encapsulation film 170 or the polarizer. In this case, the substrate 110 and the cover window can have a flexible property, thus the organic light emitting display device 100 can be a flexible display device.

As described above, the OLED D includes anyone having the structure of Chemical Formulae 1 to 3 and 6 in the emissive layer 220. The organic compound has excellent thermal stability and luminous properties, thus the OLED D can improve its luminous efficiency, lower its driving voltage and power consumption and can increase its luminous lifetime by applying the organic compound into the OLED D.

Figure 2:
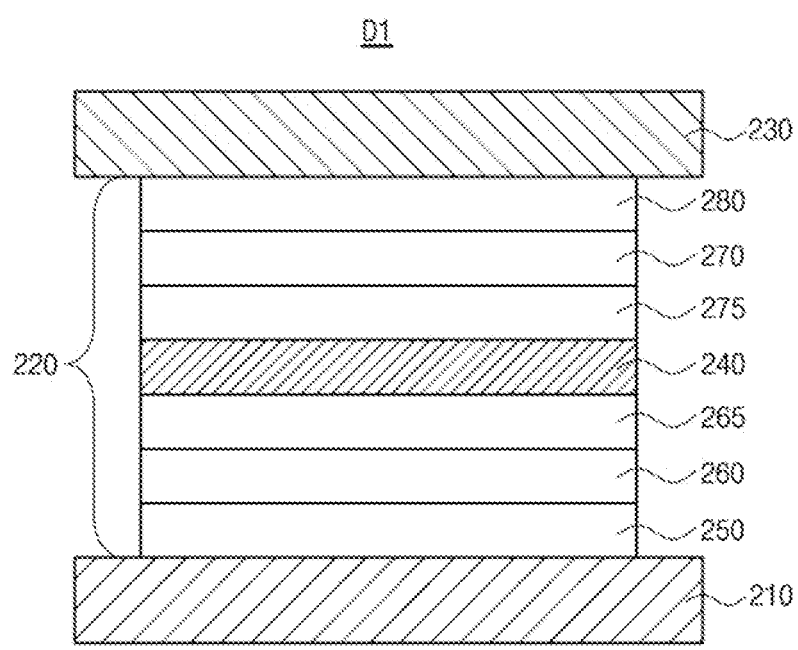
FIG. 2 is a schematic cross-sectional view illustrating an OLED in accordance with an exemplary aspect of the present disclosure.

Now, we will describe the OLED in more detail. FIG. 2 is a schematic cross-sectional view illustrating an OLED in accordance with an exemplary aspect of the present disclosure. As illustrated in FIG. 2, the OLED D1 includes first and second electrodes 210 and 230 facing each other and an emissive layer 220 with single emitting unit disposed between the first and second electrodes 210 and 230. In one exemplary aspect, the emissive layer 220 comprises an EML 240 disposed between the first and second electrodes 210 and 230. Also, the emissive layer 220 further comprises a HIL 250 and a HTL 260 that is laminated sequentially between the first electrode 210 and the EML 240, and an ETL 270 and an EIL 280 that is laminated sequentially between the EML 240 and the second electrode 230.

Alternatively, the emissive layer 220 can further comprise a first exciton blocking layer, i.e. an EBL 265 disposed between the HTL 260 and the EML 240 and/or a second exciton blocking layer, i.e. a HBL 275 disposed between the EML 240 and the ETL 270.

The first electrode 210 can be an anode that provides a hole into the EML 240. The first electrode 210 can include, but is not limited to, a conductive material having a relatively high work function value, for example, a transparent conductive oxide (TCO). In an exemplary aspect, the first electrode 210 can include, but is not limited to, ITO, IZO, ITZO, SnO, ZnO, ICO, AZO, and the like.

The second electrode 230 can be a cathode that provides an electron into the EML 240. The second electrode 230 can include, but is not limited to, a conductive material having a relatively low work function values, i.e., a highly reflective material such as Al, Mg, Ca, Ag, alloy thereof, combination thereof, and the like. For example, each of the first and second electrodes 210 and 230 can have a thickness of, but is not limited to, about 30 nm to about 300 nm.

The HIL 250 is disposed between the first electrode 210 and the HTL 260 and improves an interface property between the inorganic first electrode 210 and the organic HTL 260. In one exemplary aspect, the HIL 250 can include, but is not limited to, 4,4'4"-Tris(3-methylphenylamino)triphenylamine (MTDATA), 4,4',4"-Tris(N,N-diphenyl-amino)triphenylamine (NATA), 4,4',4"-Tris(N-(naphthalene-1-yl)-N-phenyl-amino)triphenylamine (1T-NATA), 4,4',4"-Tris(N-(naphthalene-2-yl)-N-phenyl-amino)triphenylamine (2T-NATA), Copper phthalocyanine (CuPc), Tris (4-carbazoyl-9-yl-phenyl)amine (TCTA), N,N'-Diphenyl-N, N'-bis(1-naphthyl)-1,1'-biphenyl-4,4"-diamine (NPB; NPD), 1,4,5,8,9,11-Hexaazatriphenylenehexacarbonitrile (Dipyrazino[2,3-f:2'3'-h]quinoxaline-2,3,6,7,10,11-hexacarbonitrile; HAT-CN), 1,3,5-tris[4-(diphenylamino)phenyl]benzene (TDAPB), poly(3,4-ethylenedioxythiphene)polystyrene sulfonate (PEDOT/PSS) and/or N-(biphenyl-4-yl)-9,9-dimethyl-N-(4-(9-phenyl-9H-carbazol-3-yl)phenyl)-9H-fluoren-2-amine. The HTL 250 can be omitted in compliance with a structure of the OLED D1.

The HTL 260 is disposed adjacently to the EML 240 between the first electrode 210 and the EML 240. In one exemplary aspect, the HTL 260 can include, but is not limited to, N,N'-Diphenyl-N,N'-bis(3-methylphenyl)-1,1'-biphenyl-4,4'-diamine (TPD), NPB, 4,4'-bis(N-carbazolyl)-1,1'-biphenyl (CBP), Poly[N,N'-bis(4-butylphenyl)-N,N'-bis (phenyl)-benzidine](Poly-TPD), Poly[(9,9-dioctylfluorenyl-2,7-diyl)-co-(4,4'-(N-(4-sec-butylphenyl)diphenylamine))] (TFB), Di-[4-(N,N-di-p-tolyl-amino)-phenyl]cyclohexane (TAPC), N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

In one exemplary aspect, each of the HIL 250 and the HTL 260 can have a thickness of, but is not limited to, about 5 nm to about 200 nm, preferably about 5 nm to about 100 nm.

In the first aspect, the EML 240 can comprise a first compound and a second compound. For example, the first compound can be a (first) host and the second compound can be a dopant such as fluorescent material, phosphorescent material and a delayed fluorescent material.

Hereinafter, the EML 240 where the second compound is the delayed fluorescent material will be explained. As an example, the organic compound having the structure of Chemical Formulae 1 to 3 and 6 can be used as the host. For example, the EML 240 can emit red (R), green (G) or blue (B) light.

The ETL 270 and the EIL 280 can be laminated sequentially between the EML 240 and the second electrode 230. The ETL 270 includes a material having high electron mobility so as to provide electrons stably with the EML 240 by fast electron transportation.

In one exemplary aspect, the ETL 270 can comprise, but is not limited to, oxadiazole-based compounds, triazole-based compounds, phenanthroline-based compounds, benzoxazole-based compounds, benzothiazole-based compounds, benzimidazole-based compounds, triazine-based compounds, and the like.

As an example, the ETL 270 can comprise, but is not limited to, tris-(8-hydroxyquinoline aluminum) (Alq$_3$), 2-biphenyl-4-yl-5-(4-t-butylphenyl)-1,3,4-oxadiazole (PBD), spiro-PBD, lithium quinolate (Liq), 1,3,5-Tris(N-phenyl-benzimidazol-2-yl)benzene (TPBi), Bis(2-methyl-8-quinolinato-N1,O8)-(1,1'-biphenyl-4-olato)aluminum (BAlq), 4,7-diphenyl-1,10-phenanthroline (Bphen), 2,9-Bis(naphthalene-2-yl)4,7-diphenyl-1,10-phenanthroline (NBphen), 2,9-Dimethyl-4,7-diphenyl-1,10-phenaathroline (BCP), 3-(4-Biphenyl)-4-phenyl-5-tert-butylphenyl-1,2,4-triazole (TAZ), 4-(Naphthalen-1-yl)-3,5-diphenyl-4H-1,2,4-triazole (NTAZ), 1,3,5-Tri(p-pyrid-3-yl-phenyl)benzene (TpPyPB), 2,4,6-Tris(3'-(pyridin-3-yl)biphenyl-3-yl)1,3,5-triazine (TmPPPyTz), Poly[9,9-bis(3'-(N,N-dimethyl)-N-ethylammonium)-propyl)-2,7-fluorene]-alt-2,7-(9,9-dioctylfluorene)] (PFNBr), tris(phenylquinoxaline) (TPQ) and/or diphenyl-4-triphenysilyl-phenylphosphine oxide (TSPO1).

In another exemplary aspect, the ETL 270 can comprise anyone having the structure of Chemical Formulae 1 to 3 and 6. The organic compound has an excellent affinity to electrons. In this case, the ETL 270 can comprise only the organic compound having the structure of Chemical Formulae 1 to 3 and 6, or comprise the above-described electron transporting materials mixed or doped with the organic compound.

The EIL 280 is disposed between the second electrode 230 and the ETL 270, and can improve physical properties of the second electrode 230 and therefore, can enhance the lifetime of the OLED D1. In one exemplary aspect, the EIL 280 can comprise, but is not limited to, an alkali halide such as LiF, CsF, NaF, $BaF_2$ and the like, and/or an organic metal compound such as lithium quinolate, lithium benzoate, sodium stearate, and the like. For example, each of the ETL 270 and the EIL 280 can have a thickness of, but is not limited to, about 10 nm to about 200 nm, preferably about 10 nm to about 100 nm.

When holes are transferred to the second electrode 230 via the EML 240 and/or electrons are transferred to the first electrode 210 via the EML 240, the OLED D1 can have short lifetime and reduced luminous efficiency. In order to prevent these phenomena, the OLED D1 in accordance with this aspect of the present disclosure can have at least one exciton blocking layer adjacent to the EML 240.

For example, the OLED D1 of the exemplary aspect includes the EBL 265 between the HTL 260 and the EML 240 so as to control and prevent electron transfers. In one exemplary aspect, the EBL 265 can comprise, but is not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, 1,3-bis(carbazol-9-yl)benzene (mCP), 3,3'-bis(N-carbazolyl)-1,1'-biphenyl (mCBP), CuPc, N,N'-bis[4-(bis(3-methylphenyl)amino)phenyl]-N,N'-diphenyl-[1,1'-biphenyl]-4,4'-diamine (DNTPD), TDAPB, 3,5-di(9H-carbazol-9-yl)-N,N-diphenylamine (DCDPA) and/or 2,8-bis(9-phenyl-9H-carbazol-3-yl)dibenzo[b,d]thiophene.

In addition, the OLED D1 can further include the HBL 275 as a second exciton blocking layer between the EML 240 and the ETL 270 so that holes cannot be transferred from the EML 240 to the ETL 270. In one exemplary aspect, the HBL 275 can comprise, but is not limited to, oxadiazole-based compounds, triazole-based compounds, phenanthroline-based compounds, benzoxazole-based compounds, benzothiazole-based compounds, benzimidazole-based compounds, and triazine-based compounds each of which can be used in the ETh 270.

For example, the HBL 275 can comprise a compound having a relatively low HOMO energy level compared to the luminescent materials in EML 240. The HBL 275 can comprise, but is not limited to, mCBP, BCP, BAlq, $Alq_3$, PBD, spiro-PBD, Liq, Bis-4,5-(3,5-di-3-pyridylphenyl)-2-methylpyrimidine (B3PYMPM), DPEPO, 9-(6-(9H-carbazol-9-yl)pyridine-3-yl)-9H-3,9'-bicarbazole, TSPO1 and combination thereof.

In another exemplary aspect, the HBL 275 can comprise anyone having the structure of Chemical Formulae 1 to 3 and 6. The organic compound has deep HOMO energy level for blocking holes. In this case, the HBL 275 can comprise only the organic compound having the structure of Chemical Formulae 1 to 3 and 6, or comprise the above-described hole blocking materials mixed or doped with the organic compound.

As described above, the EML 240 in the first aspect comprises the first compound that is anyone having the structure of Chemical Formulae 1 to 3 and 6 and the second compound that can be the delayed fluorescent property.

Figure 3:
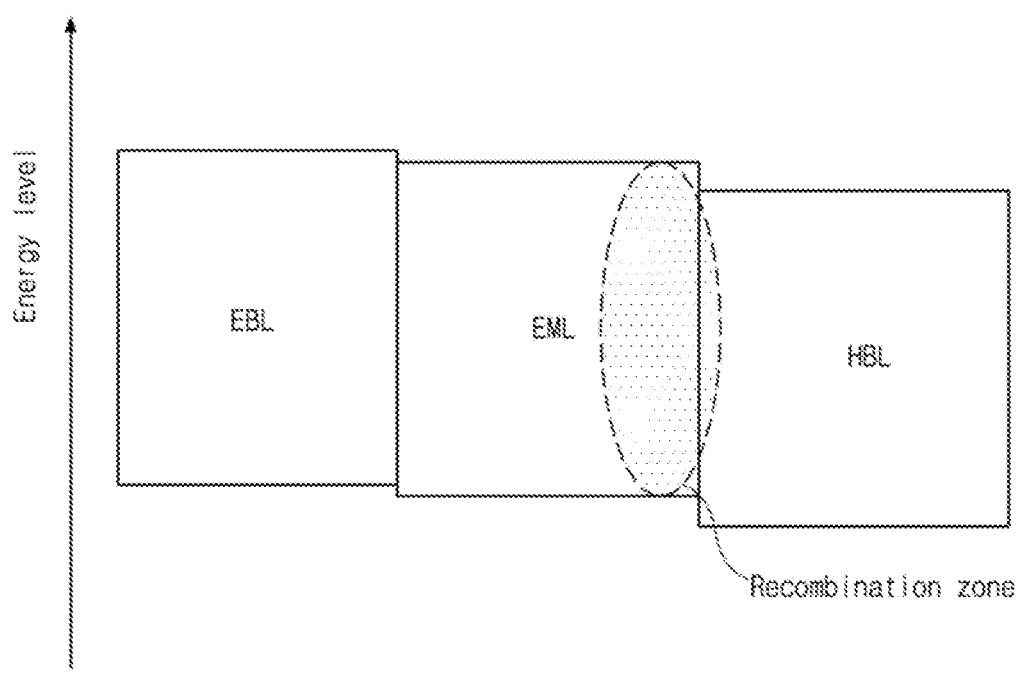
FIG. 3 is a schematic diagram illustrating a recombination zone among holes and electrons injected into the EML when using a conventional host.

In the prior art, the EML 240 has used a p-type host that has excellent affinity to holes. As illustrated schematically in FIG. 3, when the p-type host is applied into the EML 240, the recombination zone among holes and electrons is formed at an interface between the EML 240 and the HBL 275 because the p-type host prefers holes to electrons. In this case, some of charges injected into the EML 240 cannot recombine with opposite charges to be quenched without being involved in the luminescence process, and therefore, the luminous efficiency is deteriorated.

On the contrary, the organic compound having the structure of Chemical Formulae 1 to 3 and 6 is the bipolar compound that comprises the spiro moiety having the n-type property and the hetero aromatic group having the p-type property. As illustrated in FIG. 4, when the organic compound is applied into the host in the EML 240, the recombination zone among the holes and electrons are distributed uniformly in the whole area of the EML 240 including an interface between the EML 240 and the EBL 265. For example, when applying the organic compound in the EML 240, most holes and electrons injected into the EML 240 are recombined without quenching, the OLED D1 can maximize its luminous efficiency. In addition, when the second compound having the delayed fluorescent property is applied into the EML 240, the OLED D1 can further improve its luminous efficiency and luminous lifetime and lower its driving voltage.

In an OLED, holes injected from the anode and electrons injected from the cathode are recombined in the EML to form excitons of excited state, and then light is emitted as the excitons shift to the stable ground state. An external quantum efficiency (EQE, $\eta_{ext}$) of the OLED can be calculated as the following Equation:

$$\eta_{ext} = \eta_{S/T} \times \Gamma \times \Phi \times \eta_{out\text{-}coupling}$$

wherein $\eta_{S/T}$ is a singlet/triplet ratio; $\Gamma$ is a charge balance factor; $\phi$ is a radiative efficiency; and $\eta_{out\text{-}coupling}$ is an out-coupling efficiency.

When holes and electrons meet to form exciton, singlet exciton with a paired spin state and triplet exciton with an unpaired spin state is generated in a ratio of 1:3 in theory. Since only the singlet exciton participates in luminescence and the remaining 75% triplet excitons cannot participate in luminescence in the fluorescent material, the singlet/triplet ratio is 0.25 in the conventional fluorescent material. Therefore, when taking all four factors defined in the above Equation into account, the maximum luminous efficiency of the OLED using the conventional fluorescent material is only about 5%.

On the other hand, phosphorescent materials have a luminescent mechanism that converts both the singlet and triplet excitons to light. Phosphorescent materials convert singlet exciton into triplet exciton through intersystem crossing (ISC). Therefore, when using phosphorescent materials using both singlet exciton and triplet exciton, it is possible to improve the low luminous efficiency of the fluorescent materials. However, blue phosphorescent materials have too low color purity and too short lifetime to be applied into commercial display devices.

Thus, it is necessary to improve the disadvantages of the phosphorescent materials and the low luminous efficiency of the blue luminescent materials.

Recently, the delayed fluorescent material, which can solve the problems accompanied by the conventional art fluorescent and/or phosphorescent materials, has been developed. Representative delayed fluorescent material is a thermally-activated delayed fluorescent (TADF) material. Since the delayed fluorescent material generally has both an electron donor moiety and an electron acceptor moiety within its molecular structure, it can be converted to an intramolecular charge transfer (ICT) state. In case of using the delayed fluorescent material as a dopant, it is possible to use both the singlet energy and the triplet energy during the luminescent process, unlike the conventional fluorescent materials.

Figure 5:
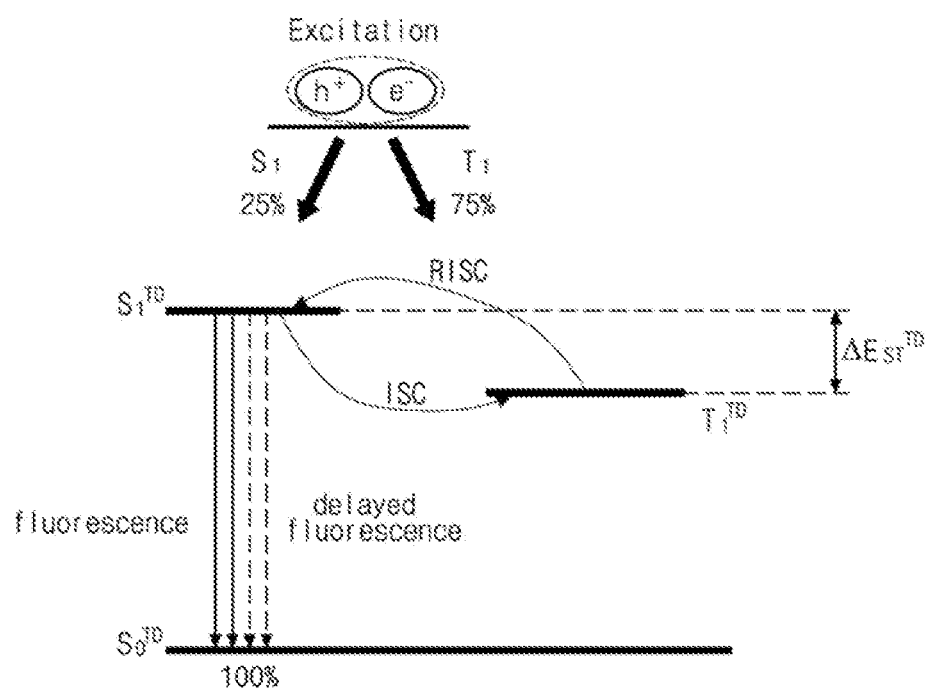
FIG. 5 is a schematic diagram illustrating a luminous mechanism of a delayed fluorescent material.

The luminous mechanism of the delayed fluorescent material will be explained with referring to FIG. 5, which is a schematic diagram illustrating a luminous mechanism of delayed fluorescent material in the EML. As illustrated in FIG. 5, the excitons of singlet energy level $S_1^{TD}$ as well as the excitons of triplet energy level $T_1^{TD}$ in the delayed fluorescent material TD can be transferred to an intermediate energy level state, i.e. ICT state, and then the intermediate stated excitons can be shifted to the ground state ($S_0^{TD}$; $S_1^{TD} \to ICT \leftarrow T_1^{TD}$). Since the excitons of singlet energy level $S_1^{TD}$ as well as the excitons of triplet energy level $T_1^{TD}$ in the delayed fluorescent material TD is involved in the luminescence process, the delayed fluorescent material TD can improve its luminous efficiency.

Since both the HOMO and the LUMO are widely distributed over the whole molecule within the common fluorescent material, it is not possible to inter-convert exciton energies between the singlet energy level and the triplet energy level within the common fluorescent material (selection rule). In contrast, since the delayed fluorescent material TD, which can be converted to ICT state, has little orbital overlaps between HOMO and LUMO, there is little interaction between the HOMO state and the LUMO state. As a result, the changes of spin states of electrons do not have an influence on other electrons, and a new charge transfer band (CT band) that does not follow the selection rule is formed within the delayed fluorescent material.

For example, since the delayed fluorescent material TD has the electron acceptor moiety spacing apart from the electron donor moiety within the molecule, it exists as a polarized state having a large dipole moment within the molecule. As the interaction between HOMO and LUMO becomes little in the state where the dipole moment is polarized, the triplet excitons as well as the singlet excitons can be converted to ICT state. For example, ICT complex can be excited to a CT state in which singlet exciton and triplet exciton can be exchanged mutually, thus the triplet excitons as well as singlet excitons can be involved in the luminescent process. In case of driving an OLED that includes the delayed fluorescent material TD, both 25% singlet excitons and 75% triplet excitons are converted to ICT state by heat or electrical field, and then the converted excitons drops to the ground state $S_0$ with luminescence. Therefore, the delayed fluorescent material TD can have 100% internal quantum efficiency in theory.

The delayed fluorescent material TD must has an energy level bandgap $\Delta E_{ST}^{TD}$ equal to or less than about 0.3 eV, for example, from about 0.05 to about 0.3 eV, between the excited singlet energy level $S_1^{TD}$ and the excited triplet energy level $T_1^{TD}$ that exciton energy in both the excited singlet energy level $S_1^{TD}$ and the excited triplet energy level $T_1^{TD}$ can be transferred to the ICT state. The material having little energy level bandgap between the singlet energy level $S_1^{TD}$ and the triplet energy level $T_1^{TD}$ can exhibit common fluorescence which the excitons of singlet energy level $S_1^{TD}$ can be directly shifted to the ground state $S_0^{TD}$, as well as delayed fluorescence with Reverser Inter System Crossing (RISC) in which the excitons of triplet energy level $T_1^{TD}$ can be transferred upwardly to the excitons of singlet energy level $S_1^{TD}$, and then the exciton of singlet energy level $S_1^{TD}$ transferred from the triplet energy level $T_1^{TD}$ can be shifted to the ground state $S_0^{TD}$.

Since the delayed fluorescent material TD obtain 100% luminous efficiency in theory, it can realize excellent internal quantum efficiency as the conventional phosphorescent material. In this case, the host can induce the triplet excitons at the delayed fluorescent material to participate in the luminescent process without quenching or non-radiative recombination. To this end, the energy levels between the host and the delayed fluorescent material should be adjusted.

Figure 6:
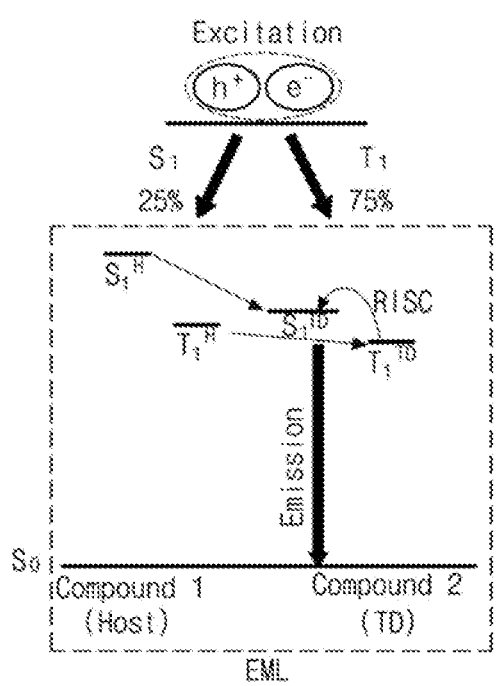
FIG. 6 is a schematic diagram illustrating luminous mechanism by energy level bandgap among luminous materials in accordance with an exemplary aspect of the present disclosure.

FIG. 6 is a schematic diagram illustrating luminous mechanism by energy level bandgap among luminous materials in accordance with an exemplary aspect of the present disclosure. As illustrated in FIG. 6, each of an excited singlet energy level $S_1^H$ and an excited triplet energy level $T_1^H$ of the first compound (Compound 1), which can be the host in the EML 240, is higher than each of the excited singlet energy level $S_1^{TD}$ and the excited triplet energy level $T_1^{TD}$ of the second compound (Compound 2) having the delayed fluorescent property. As an example, the excited triplet energy level $T_1^H$ of the first compound can be higher than the excited triplet energy level $T_1^{TD}$ of the first second compound by at least about 0.2 eV, preferably at least about 0.3 eV, and more preferably at least about 0.5 eV.

When each of the excited triplet energy level $T_1^H$ and the excited singlet energy level $S_1^{TD}$ of the first compound is not high enough than each of the excited triplet energy level $T_1^{TD}$ and the excited singlet energy level $S_1^{TD}$ of the second compound TD, the triplet state exciton energy of the second compound TD can be reversely transferred to the excited triplet energy level $T_1^{TD}$ of the first compound. In this case, the triplet exciton reversely transferred to the first compound where the triplet exciton cannot be emitted is quenched as non-emission so that the triplet exciton energy of the second compound TD having the delayed fluorescent property cannot contribute to luminescence. As an example, the first compound has, but is not limited to, the excited singlet energy level $S_1^{TD}$ equal to or more than about 3.2 eV and the excited triplet energy level $T_1^{TD}$ equal to or more than about 2.9 eV.

The second compound having the delayed fluorescent property can have the energy level bandgap $\Delta E_{ST}^{TD}$ between the excited singlet energy level $S_1^{TD}$ and the excited triplet energy level $T_1^{TD}$ equal to or less than about 0.3 eV, for example between about 0.05 eV and about 0.3 eV (see, FIG. 5).

In addition, it is necessary to adjust properly HOMO energy levels and LUMO energy levels of the first compound and the second compound. For example, it is preferable that an energy level bandgap ($|HOMO^H - HOMO^{TD}|$) between the HOMO energy level ($HOMO^H$) of the first compound and the HOMO energy level ($HOMO^{TD}$) of the second compound, or an energy level bandgap ($|LUMO^H - LUMO^{TD}|$) between the LUMO energy level ($LUMO^H$) of the first compound and the LUMO energy level ($LUMO^{TD}$) of the second compound can be equal to or less than about 0.5 eV, for example, between about 0.1 eV to about 0.5 eV. In this case, the charges can be transported efficiently from the first compound as the host to the second compound as the delayed fluorescent material and thereby enhancing the ultimate luminous efficiency in the EML 240.

Moreover, an energy level bandgap ($Eg^H$) between the HOMO energy level ($HOMO^H$) and the LUMO energy level ($LUMO^H$) of the first compound can be larger than an energy level bandgap ($Eg^{TD}$) between the HOMO energy level ($HOMO^{TD}$) and the LUMO energy level ($LUMO^{TD}$) of the second compound. As an example, the HOMO energy level ($HOMO^H$) of the first compound is deeper than the HOMO energy level ($HOMO^{TD}$) of the second compound, and the LUMO energy level ($LUMO^H$) of the first compound is shallower than the LUMO energy level ($LUMO^{TD}$) of the second compound.

The organic compound having the structure of Chemical Formulae 1 to 3 and 6 comprises the spiro moiety as an n-type moiety and the hetero aromatic group as the p-type moiety. The carbon atom in the spiro moiety includes $sp^3$ or $sp^2$ hybrid orbital and the hetero aromatic group having excellent hole affinity is linked to the spiro moiety, thus the organic compound has excellent thermal stability, and thereby its crystallization caused by Joule heat in driving the OLED D1 can be prevented or minimized. When the organic compound having the bipolar property is introduced into the EML 240 as the first compound, the recombination zone among holes and electrons is distributed over the whole area in the EML 240.

In addition, the organic compound has high excited singlet and triplet energy levels and wide energy level bandgap. The organic compound can be proper for the host in the EML 240 as well as charge transfer or charge control layer in at least one of the ETL 270 and the HBL 275. Particularly, when the EML 240 includes the organic compound and the second compound having the delayed fluorescent property, the exciton energies can be transferred to the second compound in the luminescence process without energy loss.

For example, when anyone having the structure of Chemical Formulae 1 to 3 and 6 is used as the host in the EML 240 of the OLED D1, it is possible to minimize exciton quenching resulted from the interaction between the host excitons and the adjacent polarons and to prevent the luminous lifetime owing to electrical oxidation and optical oxidation from reducing. In addition, the organic compound has excellent anti-thermal property, wide energy bandgap and a high excited triplet energy level.

Accordingly, when the organic compound having the structure of Chemical Formulae 1 to 3 and 6 is used as the host in the EML 240, the exciton energy generated at the organic compound can be efficiently transferred to second compound as the dopant. Alternatively, the organic compound can be used as the material of the ETL 270 and/or the HBL 275. In case of applying the organic compound into the emissive layer 220, the OLED D1 can enhance its luminous efficiency. As the damages to the materials applied into the EML 240 decreases, it is possible to fabricate the OLED having long luminous lifetime and excellent color purity.

In one exemplary aspect, when the organic compound having the structure of Chemical Formulae 1 to 3 and 6 is used as the first compound, it is preferable to use the second compound having delayed fluorescent property and adequate energy levels relative to the first compound. For example, the delayed fluorescent material as the second compound can emit blue (B), green (G) or red (R) light. As an example, the second compound can have, but is not limited to, the excited singlet energy level $S_1^{TD}$ between about 2.7 eV and about 2.75 eV, and the excited triplet energy level $T_1^{TD}$ between about 2.4 eV and about 2.5 eV in order to implement luminescence applicable to the display device.

For example, the second compound having the delayed fluorescent property can have the HOMO energy level $HOMO^{TD}$ between about −5.0 eV and about −6.0 eV, preferably between about −5.0 eV and about −5.5 eV, the LUMO energy level $LUMO^{TD}$ between about −2.5 eV and about −3.5 eV, preferably between about −2.5 eV and about −3.0 eV, and the energy level bandgap $Eg^{TD}$ between the HOMO and LUMO energy levels between about 2.2 eV and about 3.0 eV, preferably between about 2.4 eV and about 2.8 eV. On the other hand, the first compound, which can be the organic compound having the structure of Chemical Formulae 1 to 3 and 6, can have the HOMO energy level $HOMO^H$ between about −5.3 eV and about −6.3 eV, preferably between about −5.7 eV and about −6.1 eV, the LUMO energy level $LUMO^H$ between about −2.0 eV and about −3.0 eV, preferably between about −2.1 eV and about −2.8 eV, and the energy level bandgap $Eg^H$ between the HOMO and LUMO energy levels between about 3.0 eV and about 4.5 eV, preferably between about 3.4 eV and about 4.0 eV.

The delayed fluorescent material that can be used as the second compound of the EML 244) in accordance with an exemplary aspect can have the following structure of Chemical Formula 7:

[Chemical Formula 7]

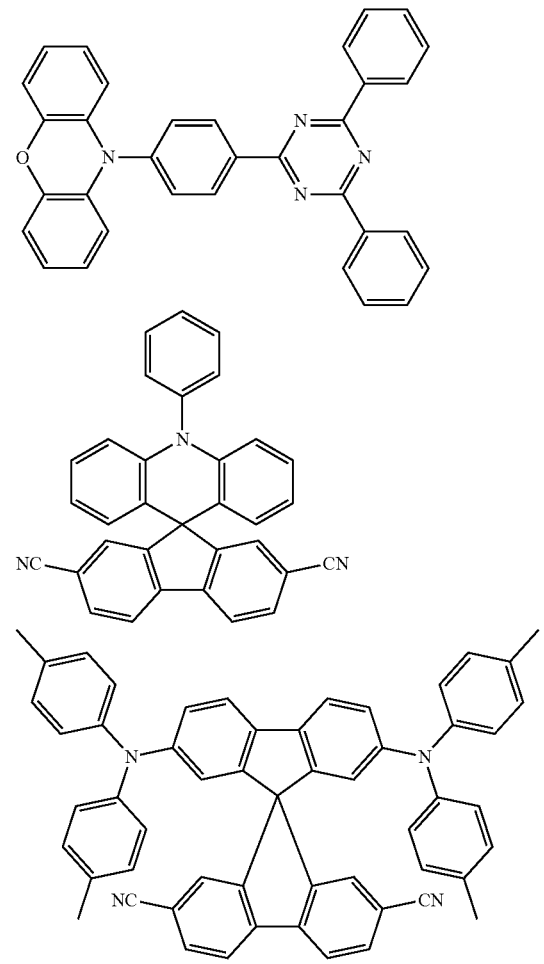

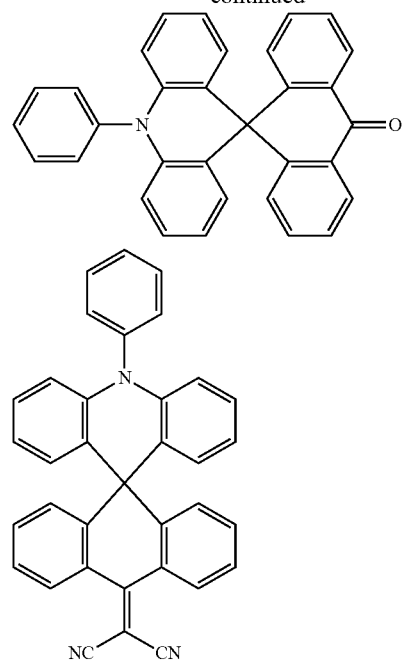
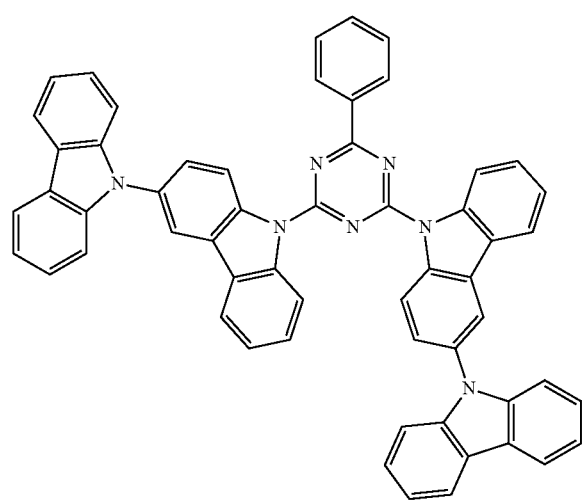
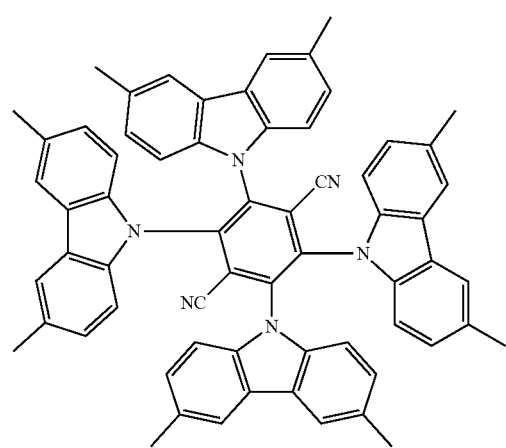
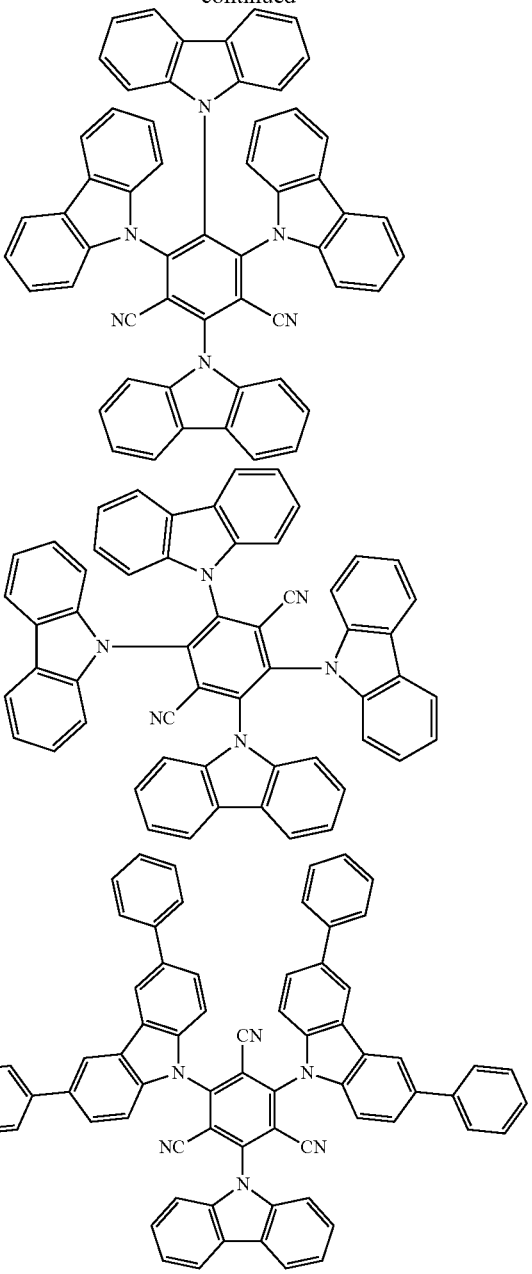
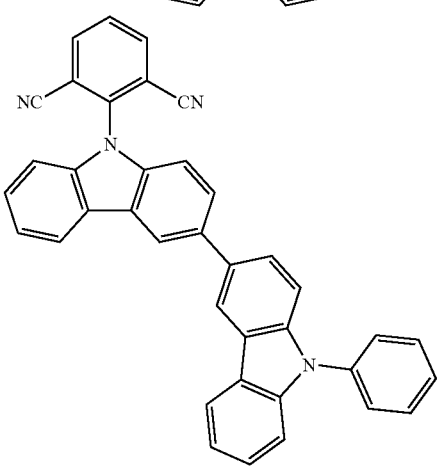

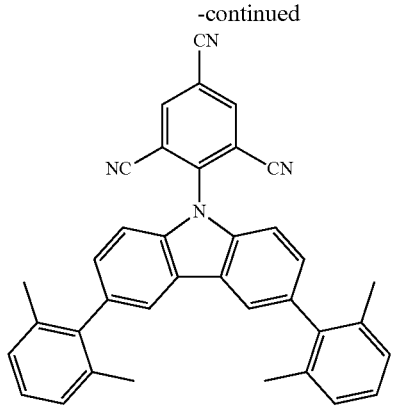
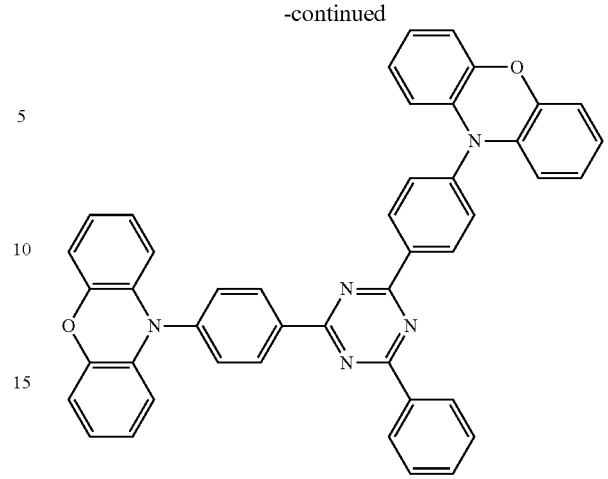
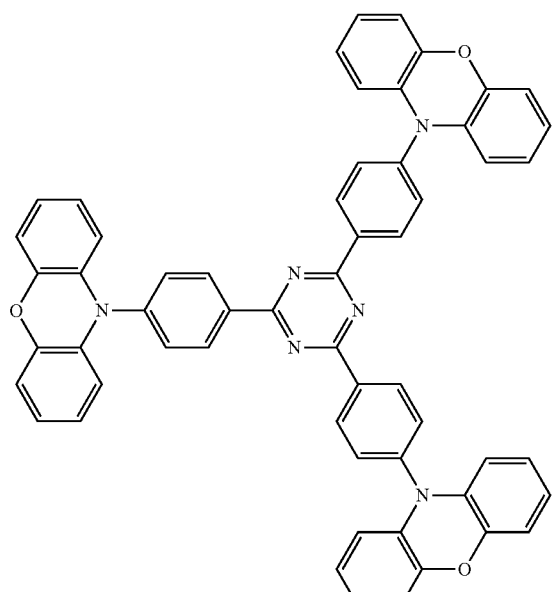
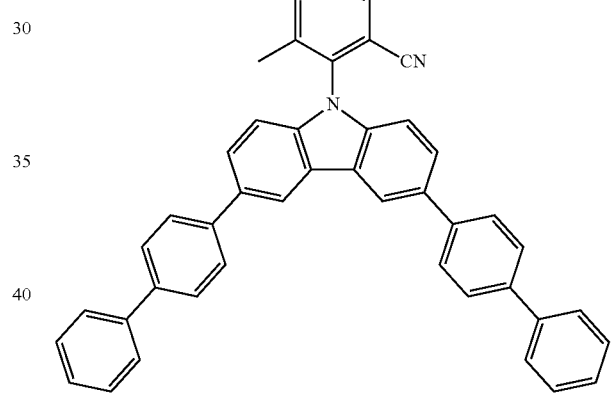
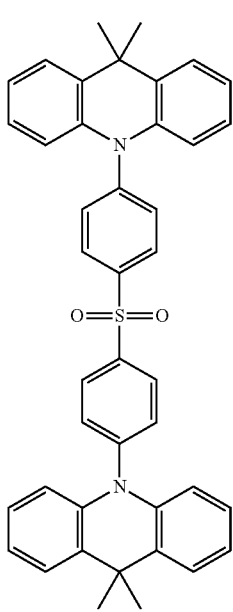
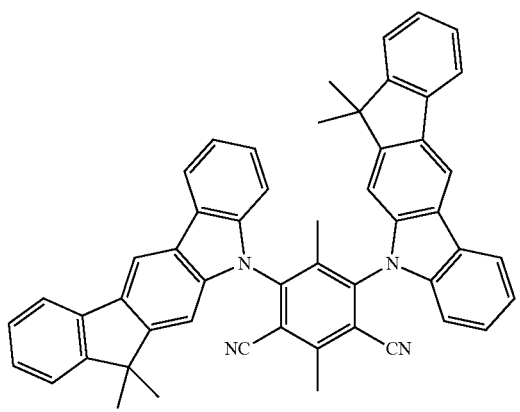

31
-continued
32
-continued
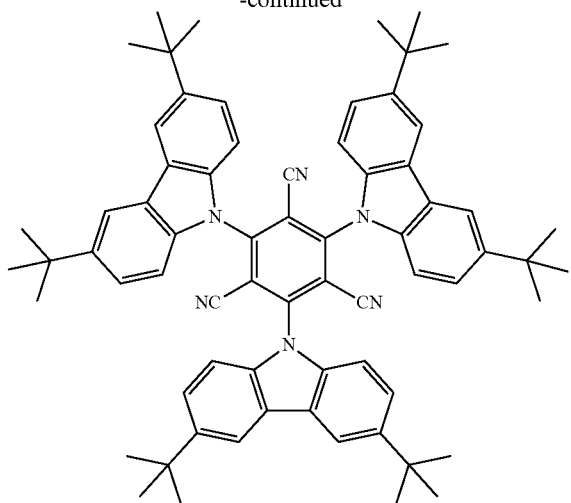
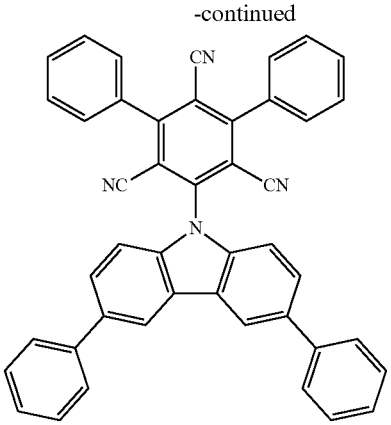
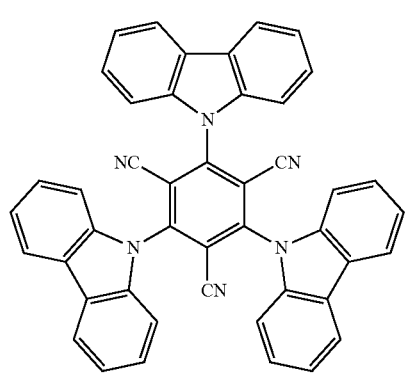
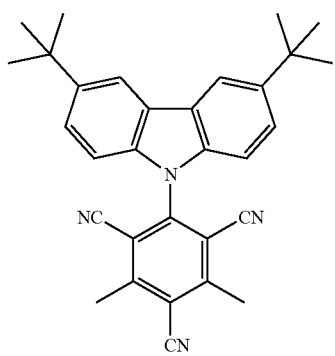
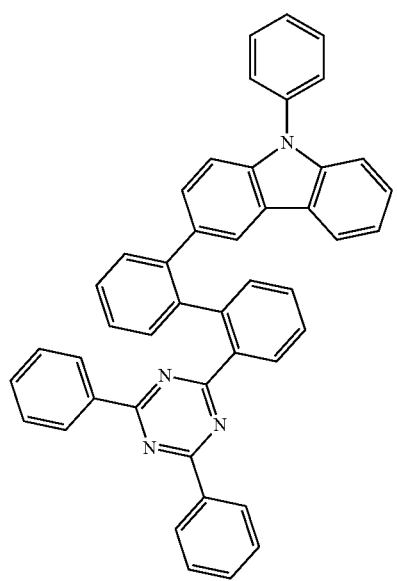
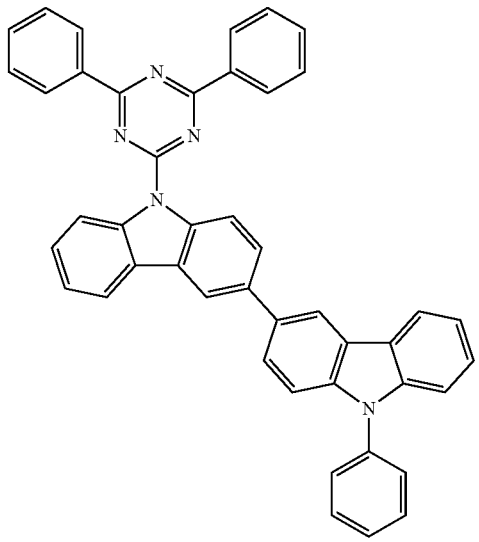

33
-continued
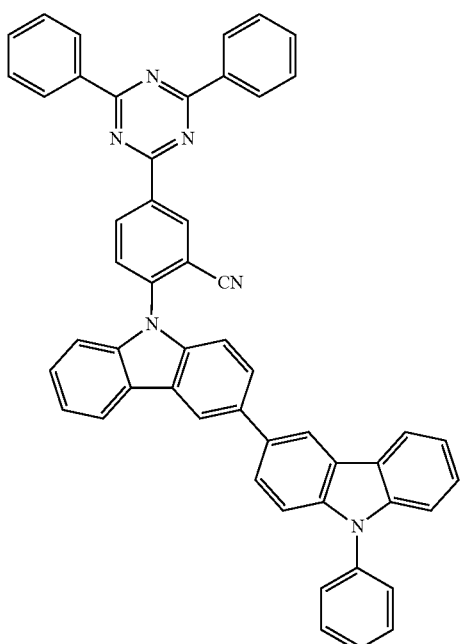
34
-continued
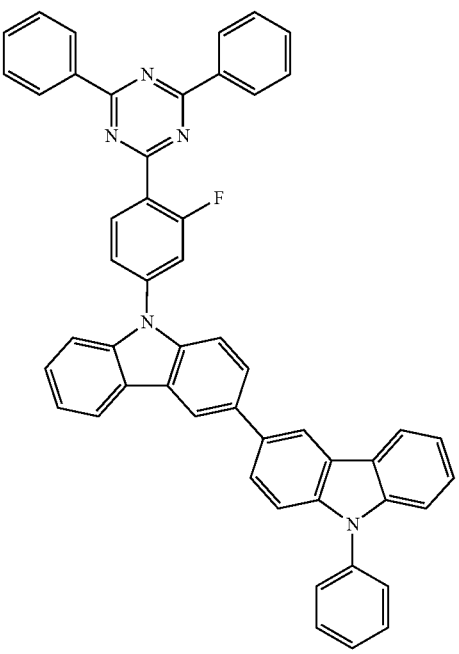
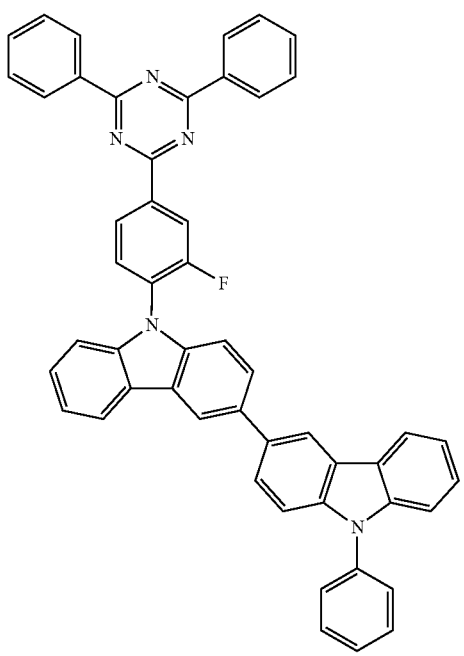
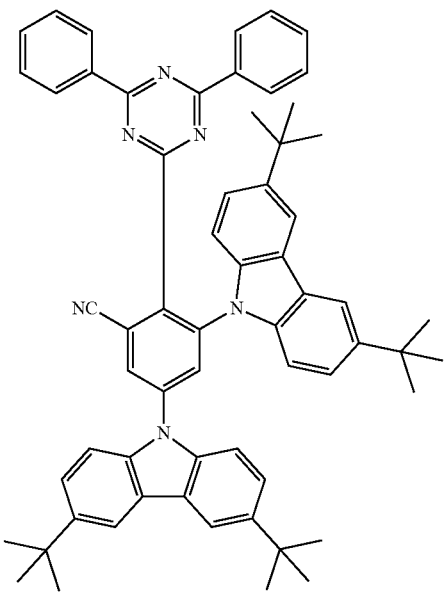

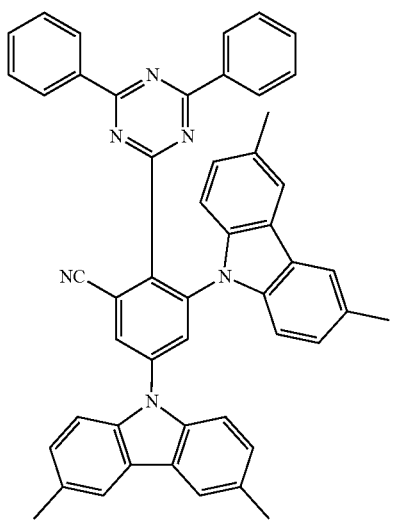
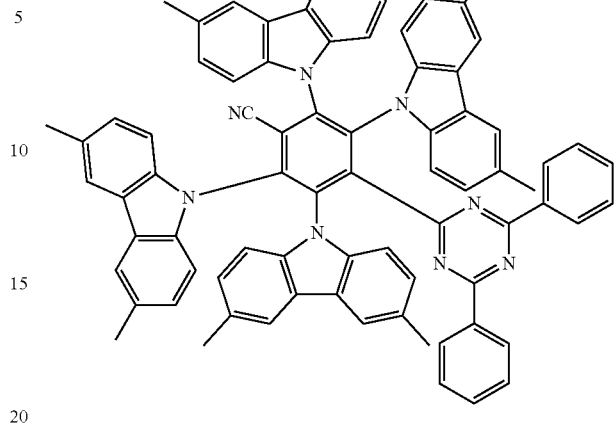
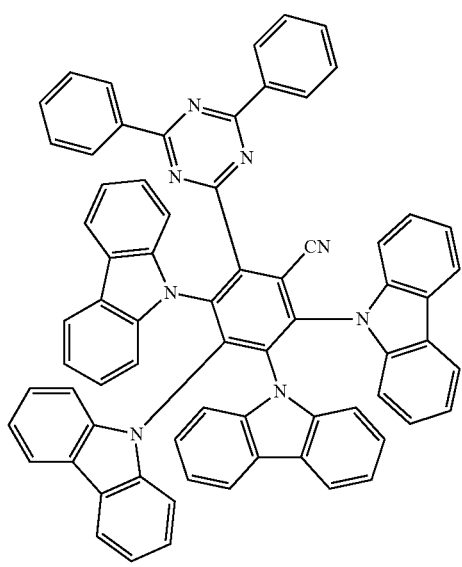
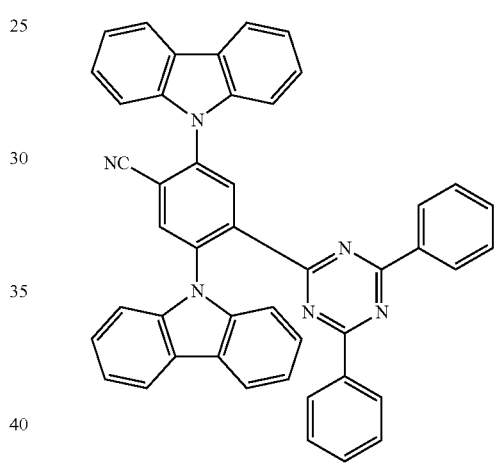
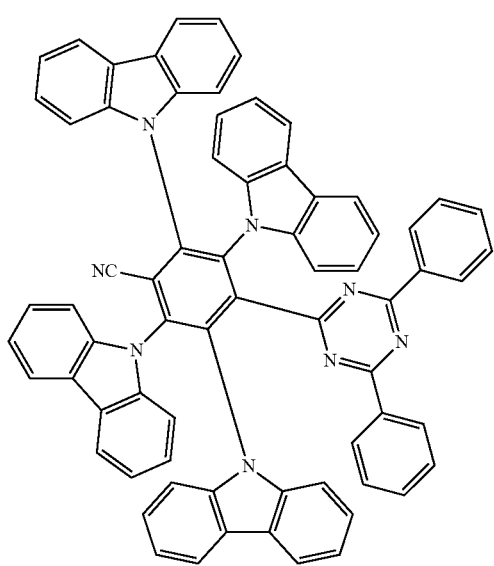
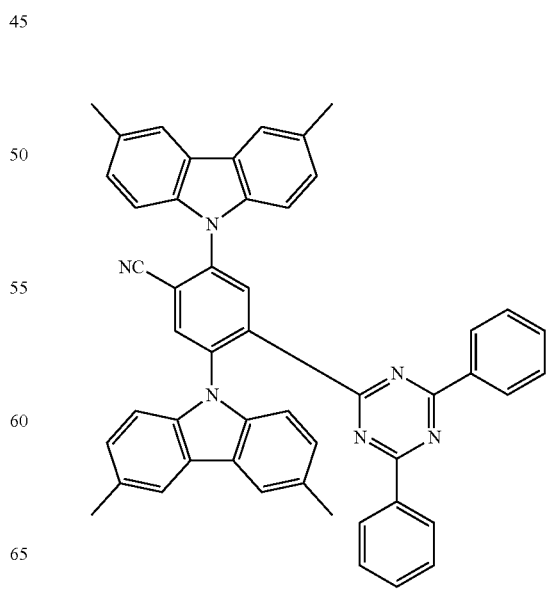

37
-continued
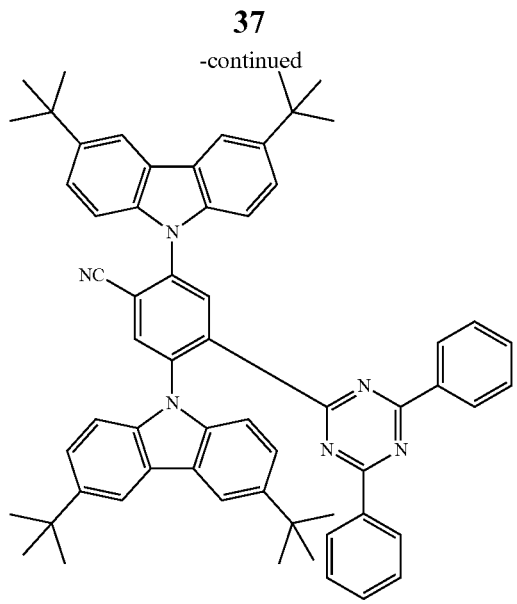
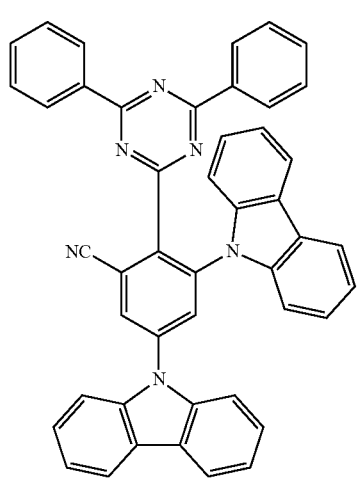
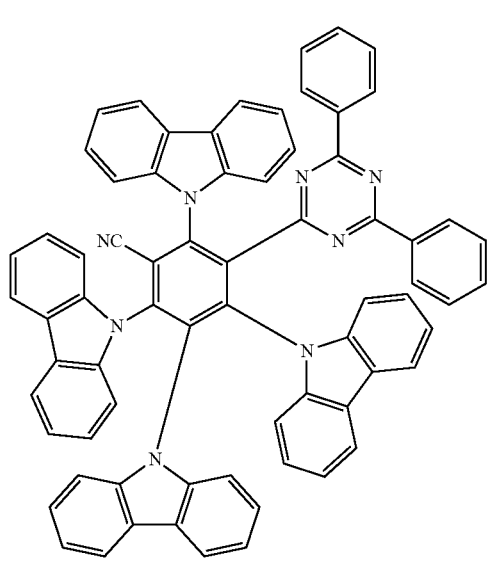
38
-continued
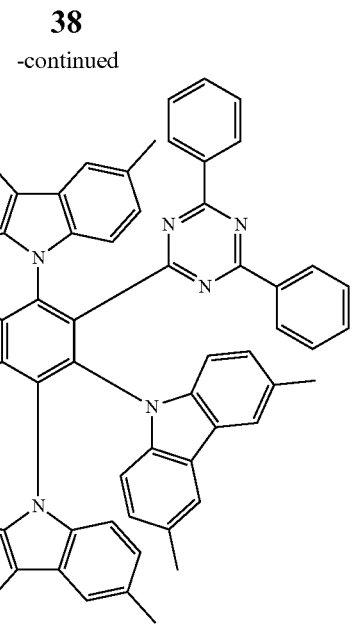
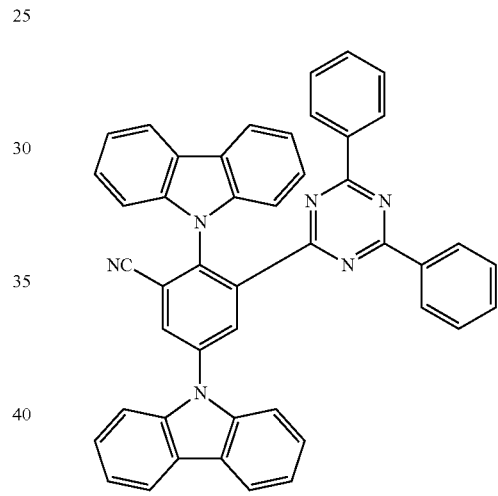
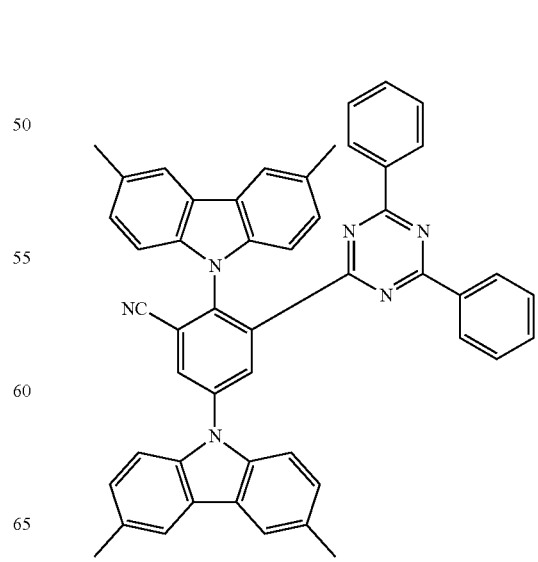

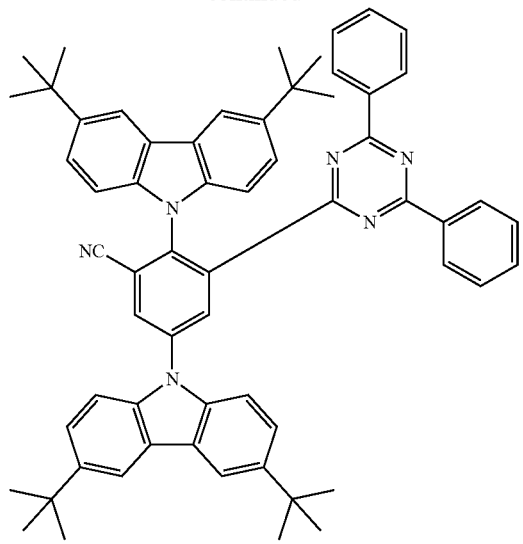
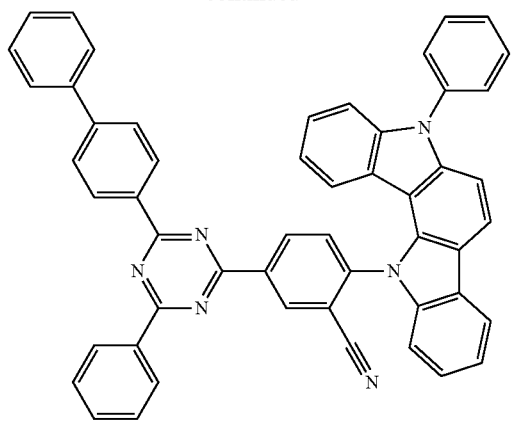
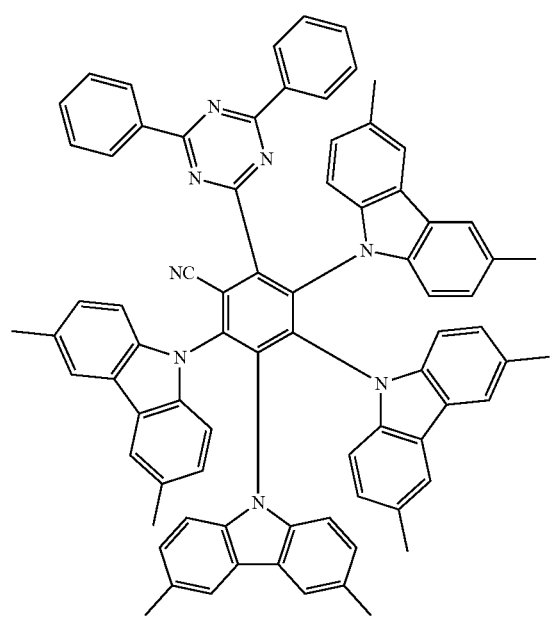
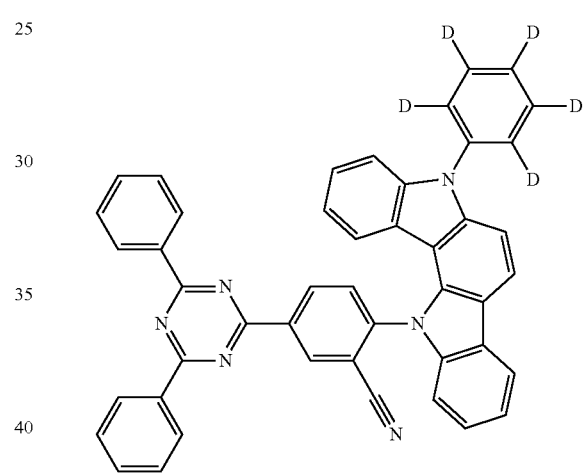
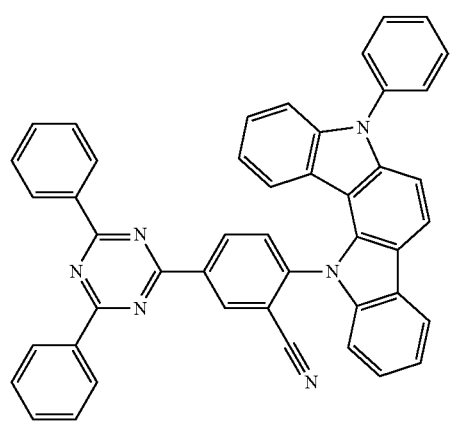
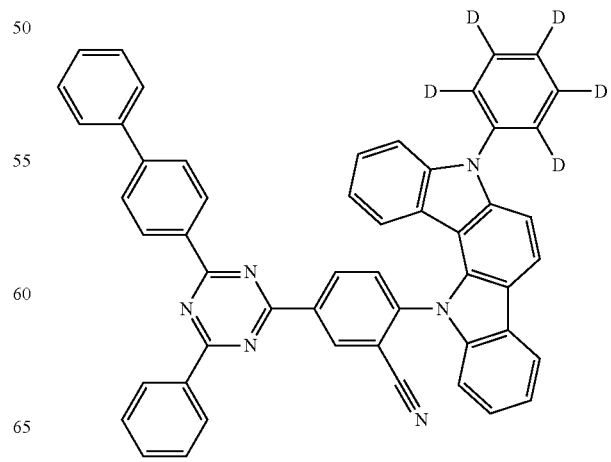

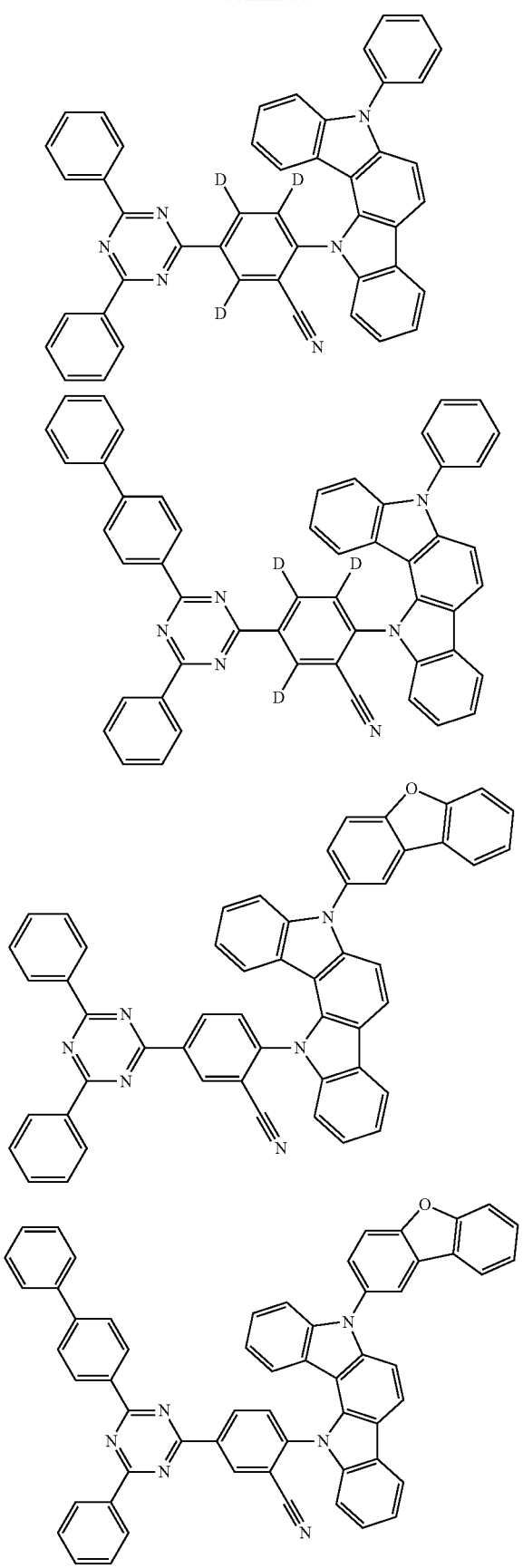
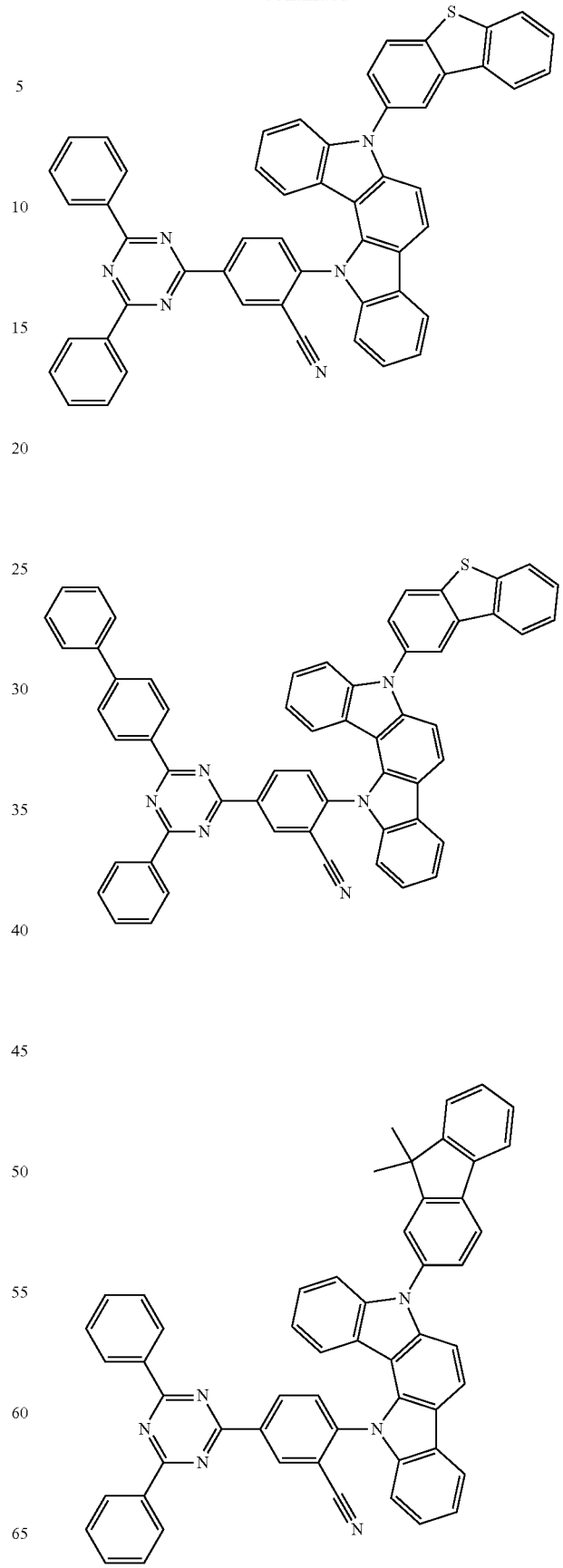

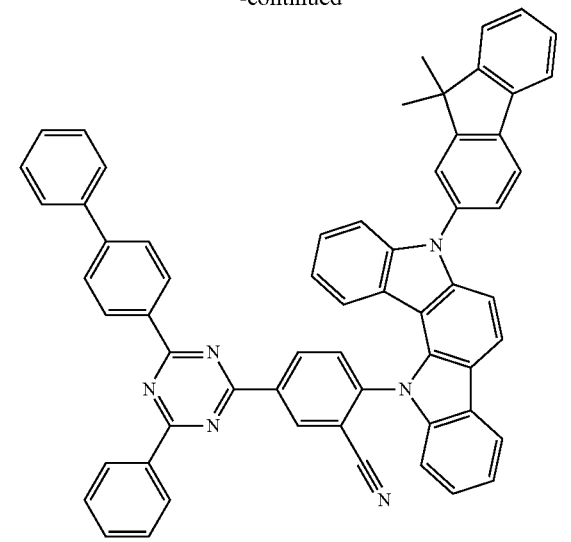
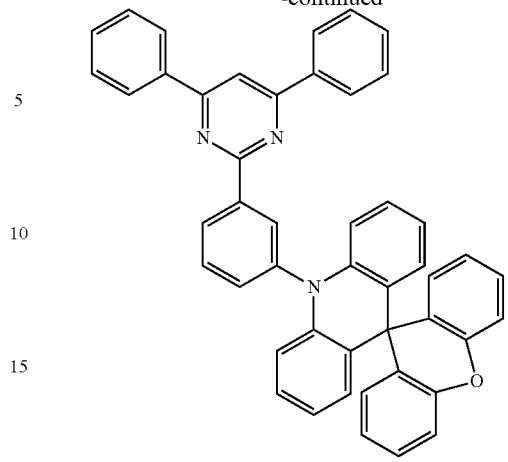
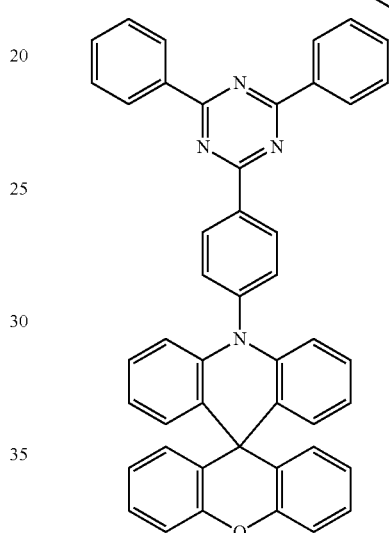
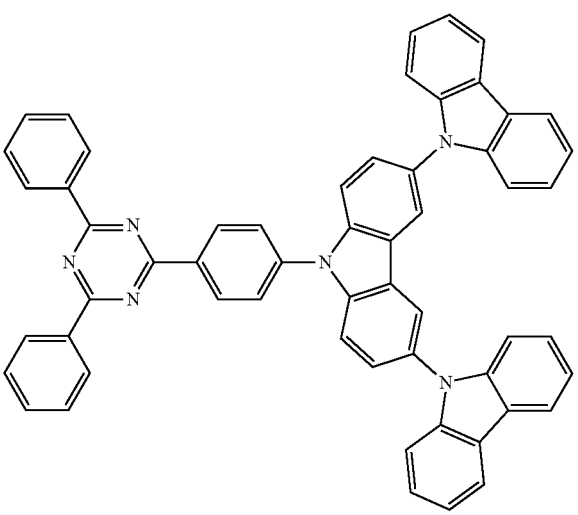
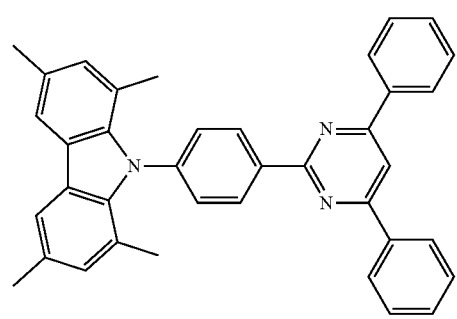

In one exemplary aspect, the second compound as blue-emitting delayed fluorescent material in the EML 240 can comprise, but is not limited to, 10-(4-(diphenylphosphoryl)phenyl)-10H-phenoxazine (SPXZPO), 10,10'-(4,4'-(phenylphosphoyrl)bis4,1-phenylene))bis(10H-phenoxazine) (DPXZPO), 10,10',10''-(4,4',4''-phosphoryltris(benzene-4,1-diyl))tris(10H-phenoxazine) (TPXZPO), 9,9'-(5-(4,6-diphenyl-1,3,5-triazin-2-yl)-1,3-phenylene)bis(9H-carbazole) (DcZTrz), 9,9',9'',9'''-((6-phenyl-1,3,5-triazin-2,4-diyl)bis(benzene-5,3,1-triyl))tetrakis(9H-carbazole) (DDczTrz), 2,7-bis(9,9-dimethylacridin-10(9H)-yl)-9,9-dimethyl-9H-thioxanthene-10,10-dioxide (DMTDAc), 9,9'-(4,4'-sulfonylbis(4,1-phenylene))bis(3,6-dimethoxyl-9H-carbazole) (DMOC-DPS), 10,10'-(4,4'-Sulfonylbis(4,1-phenylene))bis(9,9-dimethyl-9,10-dihydroacridine (DMAC-DPS), 1044-(4,6-diphenyl-1,3,5-triazin-2-yl)phenyl)-9,9-dimethyl-9,10-dihydroacridine (DMAC-TRZ), 10-phenyl-10H,10'H-spiro[acridine-9,9'-anthracen]-10'-one (ACRSA), 3,6-dibenzoyl-4,5-di(1-methyl-9-phenyl-9H-carbazoyl)-2-ethynylbenzonitrile (Cz-VPN), 9,9',9''-(5-(4,6-diphenyl-1,3,5-triazin-2-yl)benzene-1,2,3-triyl) tris(9H-carbazole) (TcZTrz), 2'-(10H-phenoxazin-10-yl)-[1,1':3',1''-terphenyl]-5'-carbonitrile (mPTC), bis(4-(911-3,9'-bicarbazol-9-yl)phenyl)methanone (CC2BP), 9'-[4-(4,6-diphenyl-1,3,5-triazin-2-yl)phenyl]-3,3'',6,6''-tetraphenyl-9,3': 6',9''-ter-9H-carbazole (BDPCC-TPTA), 9'-[4-(4,6-diphenyl-1,3,5-triazin-2-yl)phenyl]-9,3':6',9''-ter-9H-carbazole (BCC- TPTA), 9-(4-(4,6-diphenyl-1,3,5-triazin-2-yl)phenyl)-3',6'-diphenyl-9H-3,9'-bicarbazole (DPCC-TPTA), 10-(4,6-diphenyl-1,3,5-triazin-2-yl)-101H-phenoxazine (PhenTRZ), 9-(4-(4,6-diphenyl-1,3,5-triazin-2-yl)phenyl)-9H-carbazole (Cab-Ph-TRZ), 10-(4-(4,6-diphenyl-1,3,5-triazin-2-yl)phenyl)-10H-spiro[acridine-9,9'-fluorene] (SpiroAC-TRZ), 4,6-di(9H-carbazol-9-yl)isophthalonitrile (DczIPN), 3CzFCN and 2,3,4,6-tetra(9H-carbazol-9-yl)-5-fluorobenzonitrile (4CzFCN).

In another aspect, the second compound as green-emitting delayed fluorescent material in the EML 240 can comprise, but is not limited to, 5'-(phenoxazin-10-yl)-[1,1':3',1"-terphenyl]-2'-carbonitrile; oPTC), 2-biphenyl-4,6-bis(12-phenylindolo[2,3-a]carbazol-11-yl)-1,3,5-triazine (PIC-TRZ), 9,9',9"-(5-(4,6-diphenyl-1,3,5-triazin-2-yl)benzene-1,2,3-triyl)tris(3,6-dimentyl-9H-carbazole (TmCzTrz), 2,5-bis(4-(10H-phenoxazin-10-yl)phenyl)-1,3,4-oxadiazole (2PXZ-OXD), bis(4-(9,9-dimethylacridin-10(9H)-yl)phenyl) methanone (DMAC-BP), 2-(9-phenyl-9H-carbazol-3-yl)-10,10-dioxide-9H-thioxanthen-9-one (TXO-PhCz), 2,4,5,6-tetra(9H-carbazol-9-yl)isophthalonitrile (4CzIPN), 3,4,5,6-tetra(9H-carbazol-9-yl)isophthalonitrile (4CzPN), 2,3,4,6-tetra(9H-carbazol-9-yl)-5-fluorobenzonitrile (4CzFCN), 6,6-(9H,9'H-[3,3'-bicarbazole]-9,9'-diyl)bis(4-(9H-carbazol-9-yl)isophthalonitrile (33TczPN), 4,5-bis(5H-benzofuro[3,2-c]carbazol-5-yl)phthalonitrile (BFCz-2CN), 4,5-bis(5H-benzo[4,5]thieno[3,2-c]carbazol-5-yl)phthalonitrile (BTCz-2CN), 4,4"-bis(9,9-dimethylacridin-10(9H)-yl)-[1,1':2',1"-terphenyl]-4',5'-dicarbonitrile (Ac-VPN), 4,4"-di(10H-phenoxazin-10-yl)-[1,1':2',1"-terphenyl]-4',5'-dicarbonitrile (Px-VPN), 5,5'-(9H,9'H-[3,3'-bicarbazole]-9,9'-diyl)diisophthalnonitrile (35IPNDcz), 2,5'-(9H,9'H-[3,3'-bicarbazole]-9,9'-diyl)diisophthalnonitrile (26IPNDcz), 9,9', 9"-(5-(4,6-diphenyl-1,3,5-triazin-2-yl)benzene-1,2,3-triyl)-tris(9H-carbazole) (TcZTrz) and 32alCTRZ.

In still another exemplary aspect, the second compound as red-emitting delayed fluorescent material in the EML 240 can comprise, but is not limited to, 1,3-bis[4-(10H-phenoxazin-10-yl)benzoyl]benzene (mPx2BBP), 2,3,5,6-tetrakis(3,6-diphenylcarbazol-9-yl)-1,4-dicyanobenzene (4CzTPN-Ph), 10,10'-(sulfonylbis(4,1-phenylene))bis(5-phenyl-5,10-dihydrophenazine) (PPZ-DPS), 5,10-bis(4-(benzo[d]thiazol-2-yl)phenyl)-5,10-dihydrophenazine (DHPZ-2BTZ), 5,10-bis(4-(4,6-diphenyl-1,3,5-triazin-2-yl) phenyl)-5,10-dihydrophenazine (DHPZ-2TRZ) and 7,10-bis (4-(diphenylamino)phenyl)-2,3-dicyanopyrazino phenanathrene (TPA-DCPP).

When the EML 240 includes the first compound as the host and the second compound as the delayed fluorescent material, the contents of the second compound in the EML 240 can be, but is not limited to, about 1 wt % to about 70 wt %, preferably about 10 wt % to about 50 wt %, and more preferably about 20 wt % to about 50 wt %. The EML 240 can have a thickness of, but is not limited to, about 20 nm to about 200 nm, preferably about 20 to about 100 nm, and more preferably about 30 nm to about 50 nm.

Figure 7:
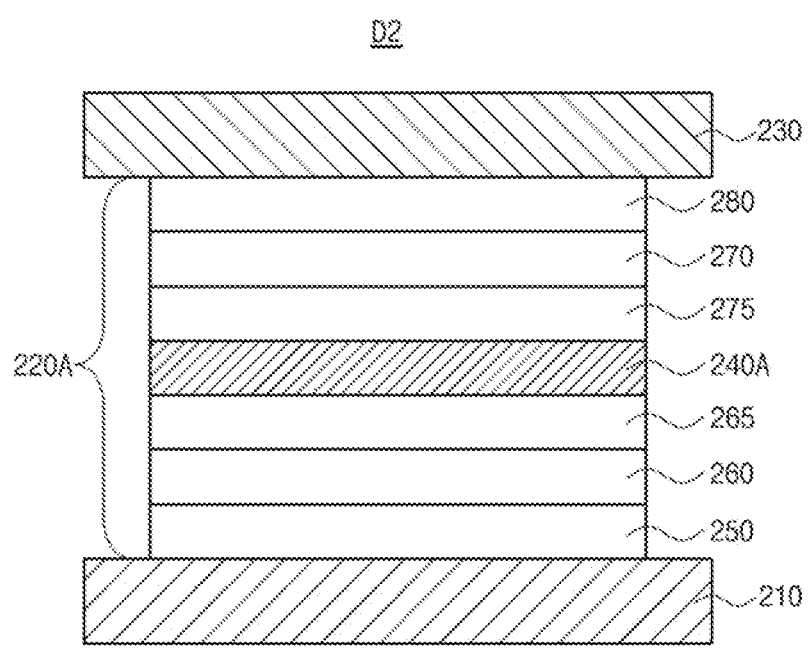
FIG. 7 is a schematic cross-sectional view illustrating an OLED in accordance with another exemplary aspect of the present disclosure.

In the above first aspect, the EML 240 includes only the first compound as the host and the second compound as the dopant. Unlike that aspect, the EML can include plural dopants having different luminous properties. FIG. 7 is a schematic cross-sectional view illustrating an OLED in accordance with another exemplary aspect of the present disclosure. As illustrated in FIG. 7, the OLED D2 comprises the first electrode 210, the second electrode 230 facing the first electrode 210 and an emissive layer 220A disposed between the first and second electrodes 210 and 230. The emissive layer 220A with single emitting unit comprises an EML 240A. Also, the emissive layer 220A comprises the HIL 250 and the HTL 260 each of which is disposed sequentially between the first electrode 210 and the EML 240A, and the ETL 270 and the EIL 280 each of which is disposed sequentially between the EML 240A and the second electrode 230. Alternatively, the emissive layer 220A can further comprise the EBL 265 disposed between the HTL 260 and the EML 240A and/or the HBL 275 disposed between the EML 240A and the ETL 270. The configurations of the first and second electrodes 210 and 230 as well as other layers except the EML 240A in the emissive layer 220A is substantially identical to the corresponding electrodes and layers in the OLED D1.

In the second aspect, the EML 240A comprise the first compound, the second compound and a third compound. The first compound can be the host, the second compound can be the delayed florescent material (first dopant), and the third material can be the fluorescent material (second dopant). The first compound can comprise any organic compound having the structure of Chemical Formulae 1 to 3 and 6. When the EML 240A further comprises the fluorescent material as well as the delayed fluorescent material as dopants, the OLED D2 can further improve its luminous efficiency and color purity by adjusting energy levels among those luminous materials.

When the EML includes only the second compound having the delayed fluorescent property as the dopant, the EML can implement high internal quantum efficiency as the prior art phosphorescent materials including heavy metals because the dopant can exhibit 100% internal quantum efficiency in theory.

However, because of the bond formation between the electron acceptor and the electron donor and conformational twists within the delayed fluorescent material, additional charge transfer transition (CT transition) within the delayed fluorescent material is caused thereby, and the delayed fluorescent material has various geometries. As a result, the delayed fluorescent materials show emission spectra having very broad FWHM (full-width at half maximum) in the course of luminescence, which results in poor color purity. In addition, the delayed fluorescent material utilizes the triplet exciton energy as well as the singlet exciton energy in the luminescence process with rotating each moiety within its molecular structure, which results in twisted internal charge transfer (TICT). As a result, the luminous lifetime of an OLED including only the delayed fluorescent materials can be reduced owing to weakening of molecular bonding forces among the delayed fluorescent materials.

Figure 8:
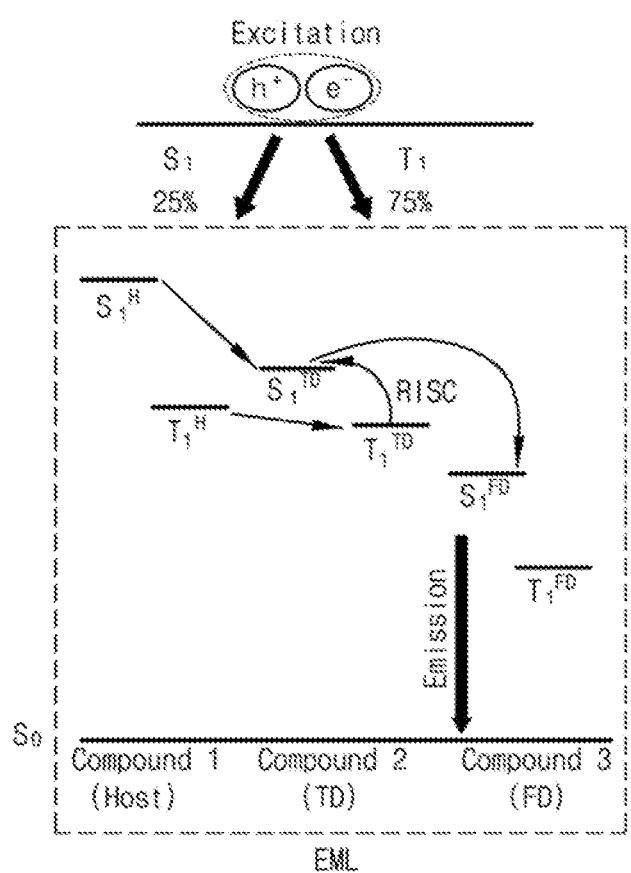
FIG. 8 is a schematic diagram illustrating luminous mechanism by energy level bandgap among luminous materials in accordance with another exemplary aspect of the present disclosure.

In the second aspect, the EML 240A further includes the third compound, which can be fluorescent or phosphorescent material, in order to prevent the color purity and luminous lifetime from being reduced in case of using only the delayed fluorescent material as the dopant. As illustrated in FIG. 8, the triplet exciton energy of the second compound having the delayed fluorescent property is converted upwardly to its own singlet exciton energy by RISC mechanism, then the converted singlet exciton energy of the second compound can be transferred to the third compound, which can be the fluorescent or phosphorescent material, in the same EML 240A by Forster Resonance Energy Transfer (FRET) mechanism to implement a hyper-fluorescence.

When the EML 240A includes the first compound (Compound) which can be any organic compound having the structure of Chemical Formulae 1 to 3 and 6, the second compound (Compound 2) having the delayed fluorescent property and the third compound (Compound 3) which is the fluorescent or phosphorescent material, it is necessary to adjust properly energy levels amount those luminous materials. FIG. 8 is a schematic diagram illustrating luminous mechanism by energy level bandgap among luminous materials in accordance with another exemplary aspect of the present disclosure.

An energy level bandgap $\Delta E_{ST}^{TD}$ between the excited singlet energy level $S_1^{TD}$ and the excited triplet energy level $T_1^{TD}$ of the second compound TD, which is the delayed fluorescent material, can be equal to or less than about 0.3 eV in order to realize the delayed fluorescence (see, FIG. 5). In addition, each of the excited singlet energy level $S_1^H$ and the excited triplet energy level $T_1^H$ of the first compound H as the host is higher than each of the excited singlet energy level $S_1^{TD}$ and the excited triplet energy level $T_1^{TD}$ of the second compound TD as the delayed fluorescent material, respectively. As an example, the excited triplet energy level $T_1^H$ of the first compound H can be higher than the excited triplet energy level $T_1^{TD}$ of the second compound TD by at least about 0.2 eV.

Moreover, the excited triplet energy level $T_1^{TD}$ of the second compound TD is higher than an excited triplet energy level $T_1^{FD}$ of the third compound FD, which is the fluorescent or phosphorescent material. In one exemplary aspect, the excited singlet energy level $S_1^{TD}$ of the second compound TD can be higher than an excited singlet energy level $S_1^{FD}$ of the third compound FD.

In addition, the energy level bandgap ($|HOMO^H-HOMO^{TD}|$) between the HOMO energy level ($HOMO^H$) of the first compound H as the host and the HOMO energy level ($HOMO^{TD}$) of the second compound TD as the delayed fluorescent compound, or the energy level bandgap ($|LUMO^H-LUMO^{TD}|$) between the LUMO energy level ($LUMO^H$) of the first compound H and the LUMO energy level ($LUMO^{TD}$) of the second compound TD can be equal to or less than about 0.5 eV.

For example, the first compound H which can be the host can include any organic compound having the structure of Chemical Formulae 1 to 3 and 6. The second compound TD which can be the delayed fluorescent material TD can comprise the organic compound having the structured of Chemical Formula 7.

For example, the second compound TD as the blue-emitting delayed fluorescent material can comprise SPXZPO, DPXZPO, TPXZPO, DcZTrz, DDczTrz, DMT-DAc, DMOC-DPS, DMAC-DPS, DMAC-TRZ, ACRSA, Cz-VPN, TcZTrz, mPTC, CC2BP, BDPCC-TPTA, BCC-TPTA, DPCC-TPTA, Phen-TRZ, Cab-Ph-TRZ, SpiroAC-TRZ, 3CzFCN and 4CzFCN. The second compound TD as the green-emitting delayed fluorescent material can comprise oPTC, PIC-TRZ, TmCzTrz, 2PXZ-OXD, DMAC-BP, TXO-PhCz, 4CzAPN, 4CzPN, 4CzFCN, 33TczPN, BFCz-2CN, BTCz-2CN, Ac-VPN, Px-VPN, 35IPNDcz, 26IPNDcz, TcZTrZ and 32alCTRZ. The second compound TD as the red-emitting delayed fluorescent material can comprise mPx2BBP, 4CzTPN-Ph, PPZ-DPS, DHPZ-2BZT, DHPZ-2TRZ and TPA-DCPP.

The exciton energy should be effectively transferred from the second compound as the delayed fluorescent material to the third compound as the fluorescent or phosphorescent material in order to implement hyper-fluorescence. With regard to energy transfer efficiency from the delayed fluorescent material to the fluorescent or phosphorescent material, an overlap between a luminescence spectrum of the delayed fluorescent material and an absorption spectrum of the fluorescent or phosphorescent material can be considered. As an example, the fluorescent or phosphorescent material having the absorption spectrum with large overlapping area with the luminescence spectrum of the second compound having the delayed fluorescent property can be used as the third compound in order to transfer exciton energy efficiently from the second compound to the third compound.

The third compound FD can emit blue (B), green (G) or red (R) light. In one exemplary aspect, the fluorescent material as the third compound can emit blue light. In this case, the third compound can comprise, but is not limited to, pyrene-based compounds, anthracene-based compounds, fluoranthene-based compounds and boron-based compounds. For example, the third compound as is the blue-emitting fluorescent material can comprise anyone having the following structure of Chemical Formula 8:

[Chemical Formula 8]

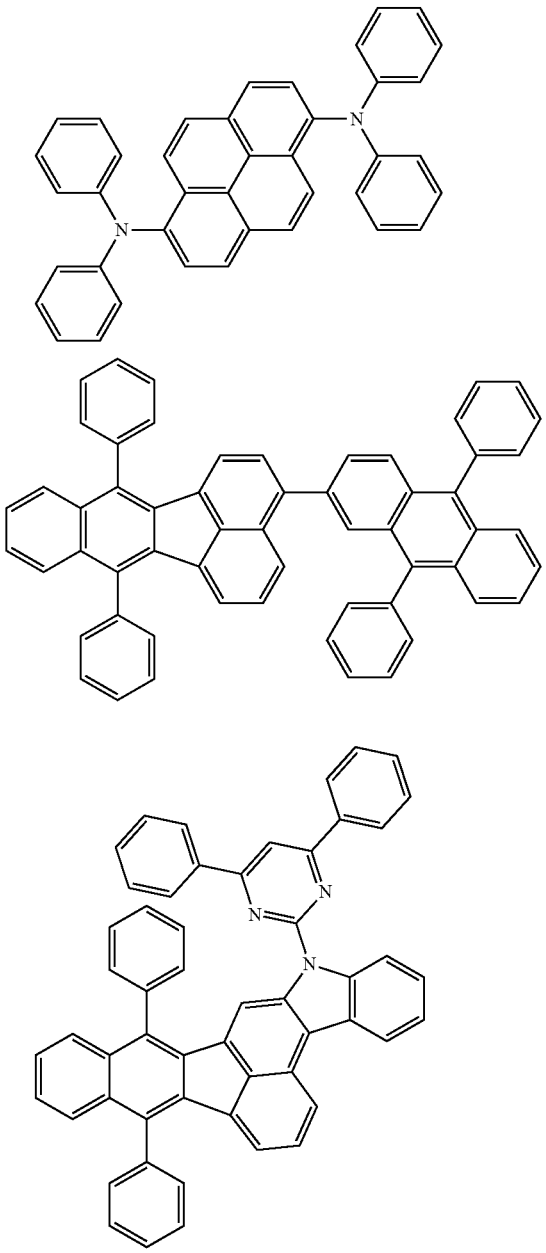

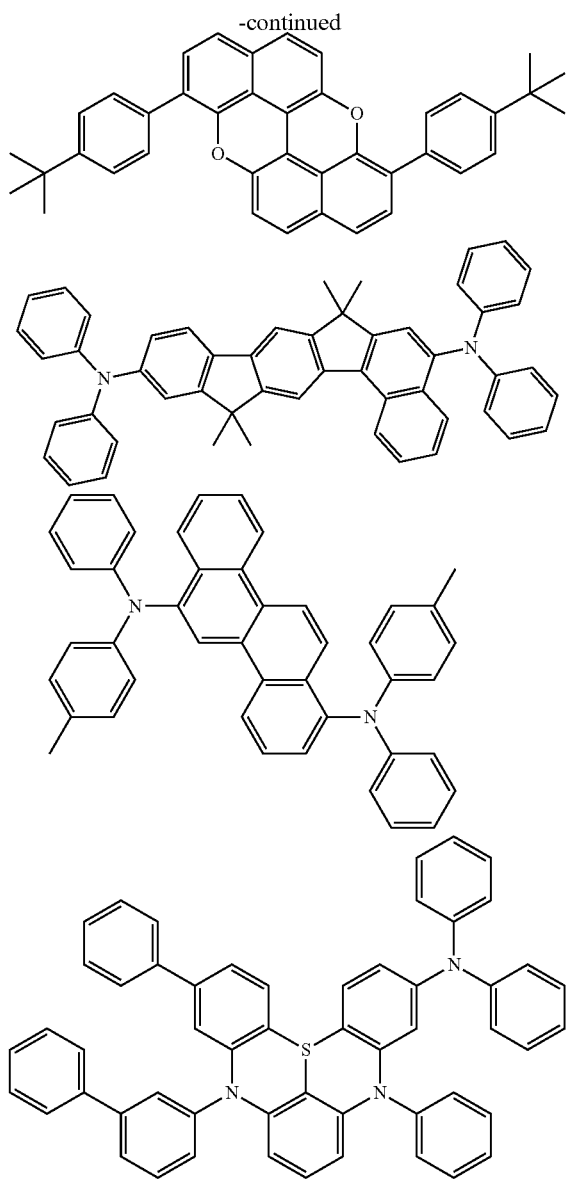

Alternatively, metal complex as the phosphorescent material emitting blue, green or red can be used as the third compound.

In one exemplary aspect, the contents of the first compound in the EML 240A can be larger than the contents of the second and third compounds. Also, the contents of the second compound can be larger than the contents of the third compound. For example, the contents of the first compound is larger than the contents of the second compound, and the conentes of the second compound is larger than the contents of the third compound. In this case, exciton energy can be transferred efficiently from the second compound to the third compound via FRET mechanism. As an example, each of the contents of the first to third compounds in the EML 240 can be, but is not limited to, about 60 wt % to about 75 wt %, about 20 wt % to about 40 wt % and about 0.1 wt % to about 5 wt %, respectively.

When the bipolar organic compound having the structure of Chemical Formulae 1 to 3 and 6 is introduced in the EML 240A, holes and electrons are injected into the EML 240A in balance, the recombination zone is formed over the whole area of the EML 240A. The OLED D2 can be driven at a lower voltage, thus it can reduce its power consumption and improve its luminous efficiency and color purity.

Figure 9:
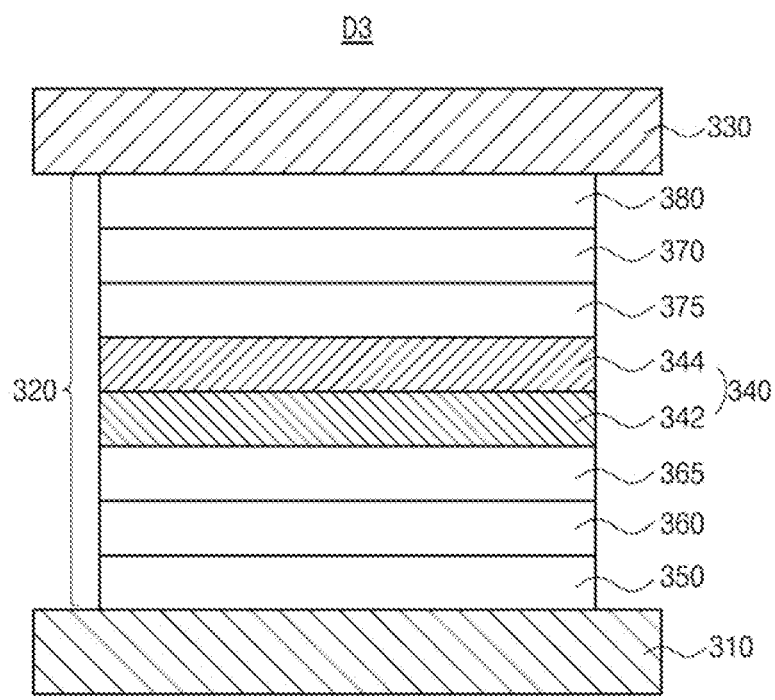
FIG. 9 is a schematic cross-sectional view illustrating an OLED diode in accordance with another exemplary aspect of the present disclosure.
Figure 10:
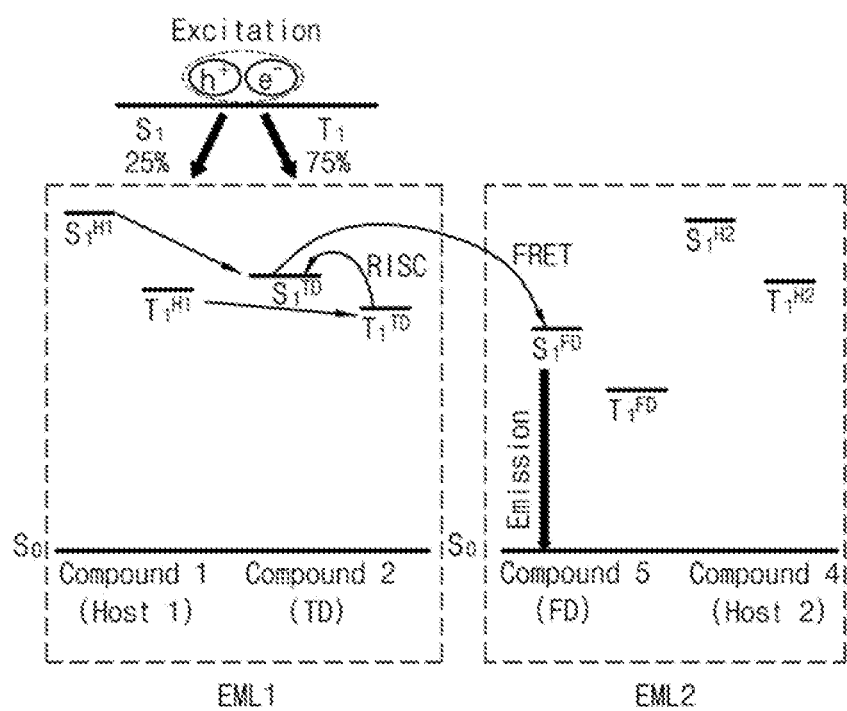
FIG. 10 is a schematic diagram illustrating luminous mechanism by energy level bandgap among luminous materials in accordance with another exemplary aspect of the present disclosure.

The OLEDs in accordance with the previous aspects have a single-layered EML. Alternatively, an OLED in accordance with the present disclosure can include multiple-layered EML. FIG. 9 is a schematic cross-sectional view illustrating an OLED having a double-layered EML in accordance with another exemplary aspect of the present disclosure. FIG. 10 is a schematic diagram illustrating luminous mechanism by energy level bandgap among luminous materials in accordance with another exemplary aspect of the present disclosure.

As illustrated in FIG. 9, the OLED D3 in accordance with an exemplary third aspect of the present disclosure includes first and second electrodes 310 and 330 facing each other and an emissive layer 320 with single emitting unit disposed between the first and second electrodes 310 and 330.

In one exemplary aspect, the emissive layer 320 comprises an EML 340. Also, the emissive layer 320 comprises an HIL 350 and an HTL 360 each of which is disposed sequentially between the first electrode 310 and the EML 340, and an ETL 370 and an EIL 380 each of which is disposed sequentially between the EML 340 and the second electrode 330. Alternatively, the emissive layer 320 can further comprise an EBL 365 disposed between the HTL 360 and the EML 340 and/or a HBL 375 disposed between the EML 340 and the ETL 370.

As described above, the first electrode 310 can be an anode and can include, but is not limited to, a conductive material having a relatively large work function values such as ITO, IZO, SnO, ZnO, ICO, AZO, and the like. The second electrode 330 can be a cathode and can include, but is not limited to, a conductive material having a relatively small work function values such as Al, Mg, Ca, Ag, alloy thereof or combination thereof.

The HIL 350 is disposed between the first electrode 310 and the HTL 360. The HIL 350 can include, but is not limited to, MTDATA, NATA, 1T-NATA, 2T-NATA, CuPc, TCTA, NPB(NPD), HAT-CN, TDAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 350 can be omitted in compliance with the structure of the OLED D3.

The HTL 360 is disposed adjacently to the EML 340 between the first electrode 310 and the EML 340. The HTL 360 can include, but is not limited to, TPD, NPD(NPB), CBP, poly-TPD, TFB, TAPC, DCDPA, N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

The EML 340 includes a first EML (EML1) 342 and a second EML (EML2) 344. The EML1 342 is disposed between the EBL 365 and the HBL 375 and the EML2 344 is disposed between the EML1 342 and the HBL 375. One of the EML1 342 and the EML2 344 includes a second compound (Compound 2, first dopant) that is the delayed fluorescent material, and the other of the EML1 342 and the EML2 344 includes a fifth compound (Compound 5, second dopant) that is the fluorescent or phosphorescent material. Also, each of the EML1 342 and the EML2 344 comprises the first compound (Compound 1, first host (Host 1)) and a fourth compound (Compound 4, second host (Host 2)), respectively. The configuration and energy levels among the luminous materials in the EML 340 will be explained in more detail below.

The ETL 370 is disposed between the EML 340 and the EIL 380. In one exemplary aspect, the ETL 370 can include, but is not limited to, oxadiazole-based compounds, triazole-based compounds, phenanthroline-based compounds, benzoxazole-based compounds, benzothiazole-based compounds, benzimidazole-based compounds, triazine-based compounds, and the like. As an example, the ETL 370 can include, but is not limited to, Alq$_3$, PBD, spiro-PBD, Liq, TPBi, BAlq, Bphen, NBphen, BCP, TAZ, NTAZ, TpPyPB, TmPPPyTz, PFNBr and/or TPQ. Alternatively, the ETL 370 can comprise anyone having the structure of Chemical Formulae 1 to 3 and 6. In this case, the ETL 370 can comprise only the organic compound having the structure of Chemical Formulae 1 to 3 and 6, or comprise the above-described electron transporting materials mixed or doped with the organic compound.

The EIL 380 is disposed between the second electrode 330 and the ETL 370. In one exemplary aspect, the EIL 380 can include, but is not limited to, an alkali halide such as LiF, CsF, NaF, BaF$_2$ and the like, and/or an organic metal compound such as lithium benzoate, sodium stearate, and the like.

The EBL 365 is disposed between the HTL 360 and the EML 340 for controlling and preventing electron transportations between the HTL 360 and the EML 340. As an example, The EBL 365 can include, but is not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluoren-2-amine, TAPC, MTDATA, mCP, mCBP, CuPc, DNTPD, TDAPB, DCDPA and/or 2,8-bis(9-phenyl-9H-carbazol-3-yl)dibenzo[b,d]thiophene.

The HBL 375 is disposed between the EML 340 and the ETL 370 for preventing hole transportations between the EML 340 and the ETL 370. In one exemplary aspect, the HBL 375 can include, but is not limited to, oxadiazole-based compounds, triazole-based compounds, phenanthroline-based compounds, benzoxazole-based compounds, benzothiazole-based compounds, benzimidazole-based compounds, and triazine-based compounds. As an example, the HBL 375 can include a compound having a relatively low HOMO energy level compared to the emitting material in EML 340. The HBL 375 can include, but is not limited to, BCP, BAlq, Alq$_3$, PBD, spiro-PBD, Liq, B3PYMPM, DPEPO, 9'-(6-(9H-carbazol-9-yl)pyridine-3-yl)-9H-3,9'-bicarbazole, TSPO1 and combination thereof.

Alternatively, the HBL 375 can comprise anyone having the structure of Chemical Formulae 1 to 3 and 6. In this case, the HBL 375 can comprise only the organic compound having the structure of Chemical Formulae 1 to 3 and 6, or comprise the above-described hole blocking materials mixed or doped with the organic compound.

In the exemplary third aspect, the EML1 342 includes the first compound H1 that can be the first host and the second compound TD that can by the delayed fluorescent material. The EML2 344 includes the fourth compound H2 that can be the second host and the fifth compound FD that can be the fluorescent or phosphorescent material.

More particularly, the EML1 342 includes the first compound that is any organic compound having the structure of Chemical Formulae 1 to 3 and 6, and the second compound that is the delayed fluorescent material. The energy level bandgap ($\Delta E_{ST}^{TD}$) between the excited singlet energy level $S_1^{TD}$ and the excited triplet energy level $T_1^{TD}$ of the second compound TD in the EML1 342 is equal to or less than about 0.3 eV (see, FIG. 5) so that triplet exciton energy of the second compound TD can be transferred to its own singlet exciton energy via RISC mechanism. While the second compound TD has high internal quantum efficiency, but it has poor color purity due to its wide FWHM (full-width half maximum).

On the contrary, the EML2 344 can include the fourth compound H2 that can be the second host and the fifth compound FD that is the fluorescent or phosphorescent material. While the fifth compound FD as the fluorescent material has an advantage in terms of color purity due to its narrow FWHM, but its internal quantum efficiency is low because its triplet exciton cannot be involved in the luminescence process.

However, in this exemplary aspect, the singlet exciton energy and the triplet exciton energy of the second dopant having the delayed fluorescent property in the EML1 342 can be transferred to the fifth compound, which can be the fluorescent or phosphorescent material, in the EML2 344 disposed adjacently to the EML1 342 by FRET mechanism, which transfers energy non-radially through electrical fields by dipole-dipole interactions. Accordingly, the ultimate light emission occurs in the fifth compound within the EML2 344.

For example, the triplet exciton energy of the second compound is converted upwardly to its own singlet exciton energy in the EML1 342 by RISC mechanism. Then, the converted singlet exciton energy of the second compound is transferred to the singlet exciton energy of the fifth compound in the EML2 344 because the second compound has the excited singlet energy level $S_1^{TD}$ higher than the excited singlet energy level $S_1^{FD}$ of the fifth compound (See, FIG. 10). The fifth compound in the EML2 344 can emit light using the triplet exciton energy as well as the singlet exciton energy.

As the exciton energy which is generated at the second compound having the delayed fluorescent property in the EML1 342 is efficiently transferred from the second compound to the fifth compound that is the fluorescent or phosphorescent material in the EML2 344, hyper-fluorescence can be realized. In this case, the substantial light emission is occurred in the EML2 344 including the fifth compound which is the fluorescent or phosphorescent material and has a narrow FWHM. Accordingly, the OLED D3 can enhance its quantum efficiency and improve its color purity due to narrow FWHM.

Each of the EML1 342 and the EML2 344 includes the first compound as the first host and the fourth compound as the second host, respectively. The exciton energies generated at the first and fourth compounds should be transferred to the second compound as the delayed fluorescent material to emit light.

As illustrated in FIG. 10, each of excited singlet energy levels $S_1^{H}1$ and $S_1^{H}2$ and excited triplet energy levels $T_1^{H}1$ and $T_1^{H}2$ of the first and fourth compounds should be higher than each of the excited singlet energy level $S_1^{TD}$ and the excited triplet energy level $T_1^{TD}$ of the second compound as the delayed fluorescent material, respectively.

For example, when each of the excited triplet energy levels $T_1^{H}1$ and $T_1^{H}2$ of the first and fourth compounds is not high enough than the excited triplet energy level $T_1^{TD}$ of the second compound, the triplet exciton of the second compound can be reversely transferred to the excited state triplet energy levels $T_1^{H}1$ and $T_1^{H}2$ of the first and fourth compounds, each of which cannot utilize triplet exciton energy. Accordingly, the excitons of the triplet energy level $T_1^{TD}$ of the second compound TD can be quenched as a non-radiative recombination and the triplet state excitons of the second compound TD cannot be involved in the emission. As an example, each of the excited triplet energy levels $T_1^{H}1$ and $T_1^{H}2$ of the first and fourth compounds can be higher than the excited triplet energy level $T_1^{TD}$ of the second compound by at least about 0.2 eV.

The excited singlet energy level $S_1^H 2$ of the fourth compound is higher than the excited singlet energy level $S_1^{FD}$ of the fifth compound. In this case, the singlet exciton energy generated at the fourth compound can be transferred to the excited singlet energy level $S_1^{FD}$ of the fifth compound. Optionally, the excited triplet energy level $T_1^{\,12}$ of the fourth compound can be higher than the excited triplet energy level $T_1^{FD}$ of the fifth compound.

In addition, it is necessary for the EML 340 to implement high luminous efficiency and color purity as well as to transfer exciton energy efficiently from the second compound TD, which is converted to ICT complex state by RISC mechanism in the EML1 342, to the fifth compound which is the fluorescent or phosphorescent material in the EML2 344. In order to realize such an OLED D3, the excited triplet energy level $T_1^{TD}$ of the second compound TD is higher than the excited triplet energy level $T_1^{FD}$ of the fifth compound FD. Optionally, the excited singlet energy level $S_1^{TD}$ of the second compound TD can be higher than the excited singlet energy level $S_1^{FD}$ of the fifth compound FD.

Moreover, the energy level bandgap ($|HOMO^H-HOMO^{TD}|$) between the HOMO energy level ($HOMO^H$) of the first and/or fourth compounds and the HOMO energy level ($HOMO^{TD}$) of the second compound, or the energy level bandgap ($|LUMO^H-LUMO^{TD}|$) between a LUMO energy level ($LUMO^H$) of the first and/or fourth compounds and the LUMO energy level ($LUMO^{TD}$) of the second compound can be equal to or less than about 0.5 eV. When the luminous materials do not satisfy the required energy levels as described above, exciton energies are quenched at the second and fifth compounds or exciton energies cannot transferred efficiently from the first and fourth compounds to the second and fifth compounds, so that OLED D3 can have reduced quantum efficiency.

The first compound H1 and the fourth compound H2 can be the same or different from each other. For example, each of the first compound and the second compound can independently include any organic compound having the structure of Chemical Formulae 1 to 3 and 6. The second compound having the delayed fluorescent property can comprise anyone having the structure of Chemical Formula 7.

For example, the second compound as the blue-emitting delayed fluorescent material can comprise SPXZPO, DPXZPO, TPXZPO, DcZTrz, DDczTrz, DMTDAc, DMOC-DPS, DMAC-DPS, DMAC-TRZ, ACRSA, Cz-VPN, TcZTrz, mPTC, CC2BP, BDPCC-TPTA, BCC-TPTA, DPCC-TPTA, Phen-TRZ, Cab-Ph-TRZ, SpiroAC-TRZ, 3CzFCN and 4CzFCN. The second compound as the green-emitting delayed fluorescent material can comprise oPTC, PIC-TRZ, TmCzTrz, 2PXZ-OXD, DMAC-BP, TXO-PhCz, 4CzIPN, 4CzPN, 4CzFCN, 33TczPN, BFCz-2CN, BTCz-2CN, Ac-VPN, Px-VPN, 35IPNDcz, 26IPNDcz, TcZTrZ and 32alCTRZ. The second compound as the red-emitting delayed fluorescent material can comprise mPx2BBP, 4CzTPN-Ph, PPZ-DPS, DHPZ-2BZT, DHPZ-2TRZ and TPA-DCPP.

The fifth compound FD can have a narrow FWHM and have an absorption spectrum with large overlapping area with a luminescent spectrum of the second compound TD. The fifth compound FD can be the fluorescent or phosphorescent material emitting blue, green or red light. For example, the fifth compound FD can comprise the blue-emitting fluorescent material that is anyone having the structure of Chemical Formula 8. Alternatively, the fifth compound FD can comprise the metal complex emitting blue, green or red light.

In one exemplary embodiment, the contents of the first and fourth compounds in the EML1 342 and the EML2 344 can be larger than or equal to the contents of the second and fifth compounds in the same layer. Also, the contents of the second compound in the EML1 342 can be larger than the contents of the fifth compound in the EML2 344. In this case, exciton energy can be transferred efficiently from the second compound to the fifth compound via FRET mechanism. As an example, the contents of the second compound in the EML1 342 can be, but is not limited to, about 1 wt % to about 70 wt %, preferably about 10 wt % to about 50 wt %, and more preferably about 20 wt % to about 50 wt %. In addition, the contents of the fourth compound in the EML2 344 can be about 90 wt % to about 99 wt %, preferably 95 wt % to about 99 wt %, and the contents of the fifth compound in the EML2 344 can be about 1 wt % to about 10 wt %, preferably about 1 wt % to about 5 wt %. Each of the EML1 342 and the EML2 344 can have a thickness of, but is not limited to, about 5 nm to about 100 nm, preferably about 10 nm to about 30 nm, and more preferably about 10 nm to about 20 nm.

When the EML2 344 is disposed adjacently to the HBL 375 in one exemplary aspect, the fourth compound, which is included in the EML2 344 together with the fifth compound, can be the same material as the HBL 375. In this case, the EML2 344 can have a hole blocking function as well as an emission function. For example, the EML2 344 can act as a buffer layer for blocking holes. In one aspect, the HBL 375 can be omitted where the EML2 344 can be a hole blocking layer as well as an emitting material layer.

When the EML2 344 is disposed adjacently to the EBL 365 in another exemplary aspect, the fourth compound can be the same material as the EBL 365. In this case, the EML2 344 can have an electron blocking function as well as an emission function. For example, the EML2 344 can act as a buffer layer for blocking electrons. In one aspect, the EBL 365 can be omitted where the EML2 344 can be an electron blocking layer as well as an emitting material layer.

When the bipolar organic compound having the structure of Chemical Formulae 1 to and 6 is introduced in the EML 340, holes and electrons are injected into the EML 340 in balance, the recombination zone is formed over the whole area of the EML 340. The OLED D3 can be driven at a lower voltage, thus it can reduce its power consumption and improve its luminous efficiency and color purity.

Figure 12:
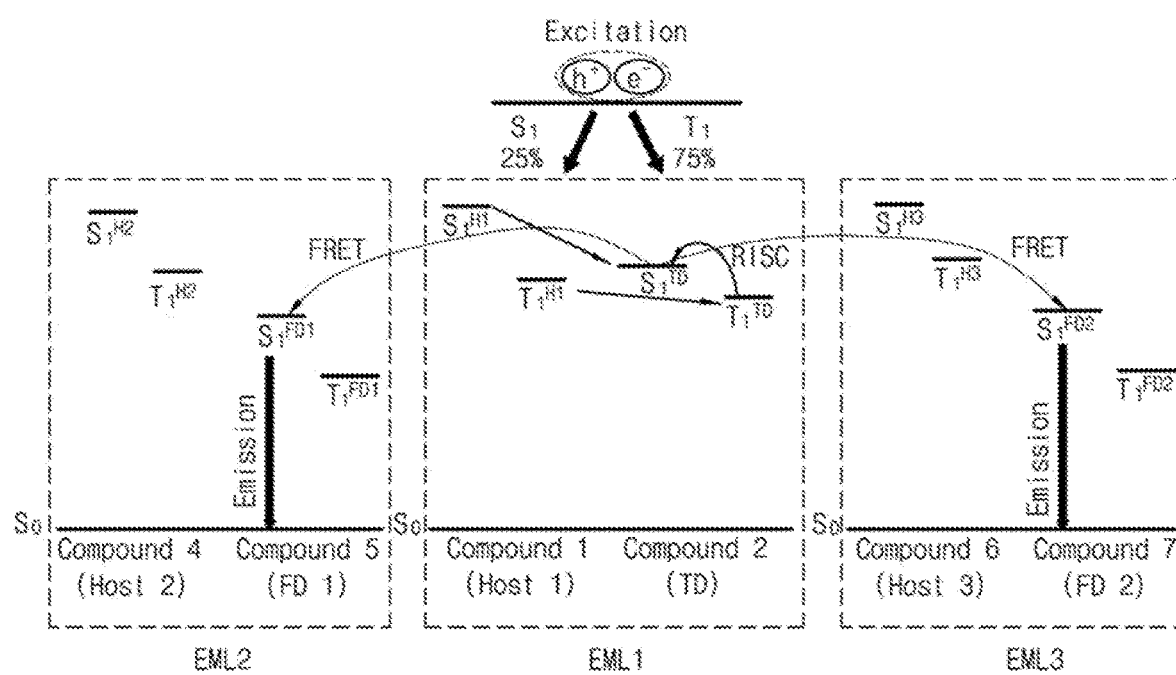
FIG. 12 is a schematic diagram illustrating luminous mechanism by energy level bandgap among luminous materials in accordance with another exemplary aspect of the present disclosure.

An OLED having a triple-layered EML will be explained. FIG. 1I is a schematic cross-sectional view illustrating an OLED having a triple-layered EML in accordance with another exemplary aspect of the present disclosure. FIG. 12 is a schematic diagram illustrating luminous mechanism by energy level bandgap among luminous materials in accordance with another exemplary aspect of the present disclosure.

Figure 11:
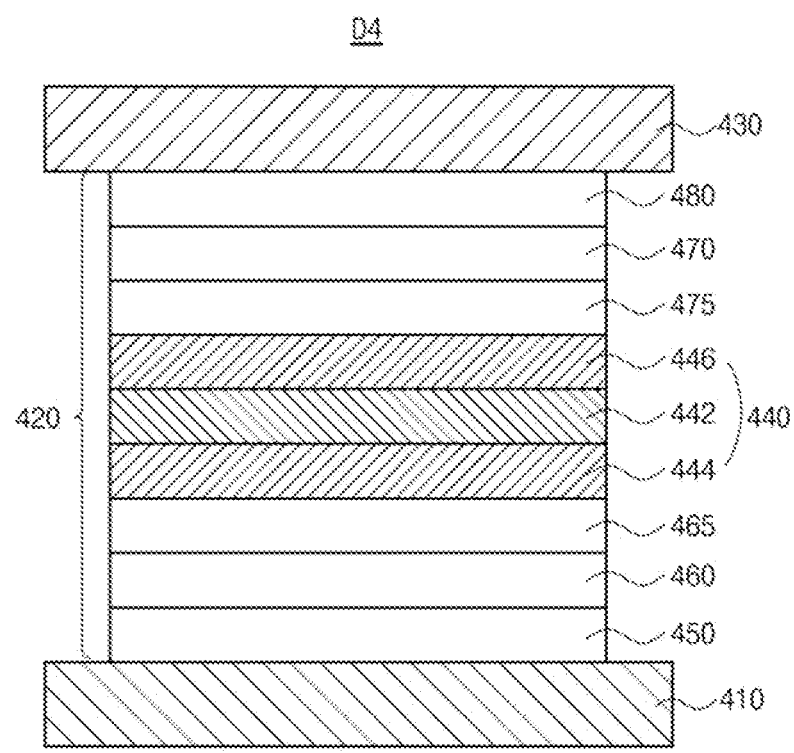
FIG. 11 is a schematic cross-sectional view illustrating an OLED in accordance with another exemplary aspect of the present disclosure.

As illustrated in FIG. 11, the OLED D4 in accordance with the fourth aspect of the present disclosure comprises first and second electrodes 410 and 430 facing each other and an emissive layer 420 with single emitting unit disposed between the first and second electrodes 410 and 430.

In one exemplary aspect, the emissive layer 420 comprises a three-layered EML 440. The emissive layer 420 comprises an HIL 450 and an HTL 460 each of which is disposed sequentially between the first electrode 410 and the EML 440, and an ETL 470 and an EIL 480 each of which is disposed sequentially between the EML 440 and the second electrode 430.

Alternatively, the emissive layer 420 can further comprise an EBL 465 disposed between the HTL 460 and the EML 440 and/or a HBL 475 disposed between the EML 440 and the ETL 470. The configurations of the first and second electrodes 410 and 430 as well as other layers except the EML 440 in the emissive layer 420 is substantially identical to the corresponding electrodes and layers in the OLEDs D1, D2 and D3.

The EML 440 comprises a first EML (EML1) 442, a second EML (EML2) 444 and a third EML (EML3) 446. The EML1 442 is disposed between the EBL 465 and the HBL 475, the EML2 444 is disposed between the EBL 465 and the EML1 442 and the EML3 446 is disposed between the EML1 442 and the HBL 475.

J The EML1 442 comprises the second compound (Compound 2, first dopant) that can be the delayed fluorescent material. Each of the EML2 444 and the EML3 446 comprises the fifth compound (Compound 5, second dopant) and a seventh compound (Compound 7, third dopant) each of which can be the fluorescent or phosphorescent material, respectively. In addition, each of the EML1 442, EML2 444 and EML3 446 further includes the first compound (Compound 1, Host 1), the fourth compound (Compound 4, Host 2) and the sixth compound (Compound 6, Host 3) each of which can be the first to third hosts, respectively.

In accordance with this aspect, the singlet energy as well as the triplet energy of the second compound, i.e. the delayed fluorescent material in the EML1 442 can be transferred to the fifth and seventh compounds, i.e. the fluorescent or phosphorescent materials each of which is included in the EML2 444 and EML3 446 disposed adjacently to the EML1 442 by FRET mechanism. Accordingly, the ultimate emission occurs in the fifth and seventh compounds in the EML2 444 and the EML3 446.

For example, the triplet exciton energy of the second compound TD having the delayed fluorescent property in the EML1 442 is converted upwardly to its own singlet exciton energy by RISC mechanism, then the singlet exciton energy of the second compound is transferred to the singlet exciton energy of the fifth and seventh compounds FD1 and FD2 in the EML2 444 and the EML3 446 because the second compound TD has the excited singlet energy level $S_1^{TD}$ higher than each of the excited singlet energy levels $S_1^{FD1}$ and $S_1^{FD2}$ of the fifth and seventh compounds FD1 and FD2 (see, FIG. 12). The singlet exciton energy of the second compound TD in the EML1 442 is transferred to the fifth and seventh compounds FD1 and FD2 in the EML2 444 and the EML3 446 which are disposed adjacently to the EML1 442 by FRET mechanism.

The fifth and seventh compounds FD1 and FD2 in the EML2 444 and EML3 446 can emit light using the singlet exciton energy and the triplet exciton energy derived from the second compound TD. Each of the fifth and seventh compounds FD1 and FD2 can have narrower FWHM compared to the second compound TD. As the exciton energy, which is generated at the second compound TD having the delayed fluorescent property in the EML1 442, is transferred to the fifth and seventh compounds FD1 and FD2 in the EML2 444 and the EML3 446, hyper-fluorescence can be realized. Particularly, each of the fifth and seventh compounds FD1 and FD2 can have a luminescent spectrum having a large overlapping area with an absorption spectrum of the second compound TD, so that exciton energy of the second compound TD can be transferred efficiently to each of the fifth and seventh compounds FD1 and FD2. In this case, substantial light emission is occurred in the EML2 444 and in the EML3 446.

To implement efficient luminescence in the EML 440, it is necessary to adjust properly energy levels among luminous materials in the EML1 442, the EML2 444 and the EML3 446. As illustrated in FIG. 12, each of excited singlet energy levels $S_1^{H1}$, $S_1^{H2}$ and $S_1^{H3}$ and excited triplet energy levels $T_1^{H1}$, $T_1^{H2}$ and $T_1^{H3}$ of the first, fourth and sixth compounds, each of which can be the first to third hosts, respectively, should be higher than each of the excited singlet energy level $S_1^{TD}$ and the excited triplet energy level $T_1^{TD}$ of the second compound TD that can be the delayed fluorescent material, respectively.

For example, when each of the excited triplet energy levels $T_1^{H1}$, $T_1^{H2}$ and $T_1^{H3}$ of the first, fourth and sixth compounds is not high enough than the excited triplet energy level $T_1^{TD}$ of the second compound TD, the triplet exciton of the second compound TD can be reversely transferred to the excited triplet energy levels $T_1^{H1}$, $T_1^{H2}$ and $T_1^{H3}$ of the first, fourth and sixth compounds, each of which cannot utilize triplet exciton energy. Accordingly, the excitons of the triplet energy level $T_1^{TD}$ of the second compound TD can be quenched as a non-radiative recombination and the triplet state excitons of the second compound TD cannot be involved in the luminescence.

In addition, it is necessary for the EML 440 to implement high luminous efficiency and color purity as well as to transfer exciton energy efficiently from the second compound TD, which is converted to ICT complex state by RISC mechanism in the EML1 442, to the fifth and seventh compounds FD1 and FD2 each of which is the fluorescent or phosphorescent material in the EML2 444 and the EML3 446. In order to realize such an OLED D4, the excited triplet energy level $T_1^{TD}$ of the second compound TD in the EML1 442 is higher than each of excited triplet energy levels $T_1^{FD1}$ and $T_1^{FD2}$ of the fifth and seventh compounds FD1 and FD2. Alternatively, the excited singlet energy level $S_1^{TD}$ of the second compound TD can be higher than each of excited singlet energy levels $S_1^{FD1}$ and $S_1^{FD2}$ of the fifth and seventh compounds FD1 and FD2 as fluorescent or phosphorescent material.

Moreover, the exciton energy, which is transferred from the second compound TD to each of the fifth and seventh compounds FD1 and FD2, should not be transferred to the fourth and sixth compounds in order to realize efficient light emission. As an example, each of the excited singlet energy levels $S_1^{H2}$ and $S_1^{H3}$ of the fourth and sixth compounds can be higher than each of the excited singlet energy levels $S_1^{FD1}$ and $S_1^{FD2}$ of the fifth and seventh compounds FD1 and FD2, respectively. In one exemplary aspect, the energy level bandgap between the excited singlet energy level $S_1^{TD}$ and the excited triplet energy level $T_1^{TD}$ of the second compound TD can be equal to or less than about 0.3 eV in order to implement a delayed fluorescence (see, FIG. 5).

In addition, the energy level bandgap ($|HOMO^H - HOMO^{TD}|$) between the HOMO energy levels ($HOMO^H$) of the first, fourth and sixth compounds each of which can be the first to third hosts, respectively, and the HOMO energy level ($HOMO^{TD}$) of the second compound TD, or the energy level bandgap ($|LUMO^H - LUMO^{TD}|$) between the LUMO energy level ($LUMO^H$) of the first, fourth and sixth compounds and the LUMO energy level ($LUMO^{TD}$) of the second compound TD can be equal to or less than about 0.5 eV.

Each of the EML1 442, the EML2 444 and the EML3 446 can include the first, fourth and sixth compounds each of which can be the first to third hosts, respectively. For example, each of the first, fourth and sixth compounds can be the same or different from each other. For Example, each of the first, fourth and sixth compounds can independently include any organic compound having the structure of Chemical Formulae 1 to and 6. The second compound TD having the delayed fluorescent property can comprise anyone having the structure of Chemical Formula 7.

For example, the second compound TD as the blue-emitting delayed fluorescent material can comprise SPXZPO, DPXZPO, TPXZPO, DcZTrz, DDczTrz, DMT-DAc, DMOC-DPS, DMAC-DPS, DMAC-TRZ, ACRSA, Cz-VPN, TcZTrz, mPTC, CC2BP, BDPCC-TPTA, BCC-TPTA, DPCC-TPTA, Phen-TRZ, Cab-Ph-TRZ, SpiroAC-TRZ, 3CzFCN and 4CzFCN. The second compound TD as the green-emitting delayed fluorescent material can comprise oPTC, PIC-TRZ, TmCzTrz, 2PXZ-OXD, DMAC-BP, TXO-PhCz, 4CzAPN, 4CzPN, 4CzFCN, 33TczPN, BFCz-2CN, BTCz-2CN, Ac-VPN, Px-VPN, 35IPNDcz, 26IPNDcz, TcZTrZ and 32alCTRZ. The second compound TD as the red-emitting delayed fluorescent material can comprise mPx2BBP, 4CzTPN-Ph, PPZ-DPS, DHPZ-2BZT, DHPZ-2TRZ and TPA-DCPP.

Each of the fifth and seventh compounds FD1 and FD2 can have a narrow FWHM and have an absorption spectrum with large overlapping area with a luminescence spectrum of the second compound TD. Each of the fifth and seventh compounds FD1 and FD2 can be the fluorescent or phosphorescent material emitting blue, green or red light. For example, each of the fifth and seventh compounds FD1 and FD2 can independently comprise the blue-emitting fluorescent material that is anyone having the structure of Chemical Formula 8. Alternatively, each of the fifth and seventh compounds FD1 and FD2 can comprise the metal complex emitting blue, green or red light.

In one exemplary aspect, each of the contents of the fourth and sixth compounds in the EML2 444 and the EML3 446 can be larger than or equal to each of the contents of the fifth and seventh compounds in the same layer. Also, the contents of the second compound ID in the EML1 442 can be larger than each of the contents of the fifth and seventh compounds FD1 and FD2 in the EML2 444 and in the EML3 446. In this case, exciton energy can be transferred efficiently from the second compound to the fifth and seventh compounds via FRET mechanism. As an example, the contents of the second compound TD in the EML1 442 can be, but is not limited to, about 1 wt % to about 70 wt %, preferably about 10 wt % to about 50 wt %, and more preferably about 20 wt % to about 50 wt %. In addition, each of the contents of the fourth and sixth compounds in the EML2 444 and in the EML3 446 can be about 90 wt % to about 99 wt %, preferably 95 wt % to about 99 wt %, and each of the contents of the fifth and seventh compounds FD1 and FD2 in the EML2 444 and in the EML3 446 can be about 1 wt % to about 10 wt %, preferably about 1 wt % to about 5 wt %. The EML1 442 can have a thickness of, but is not limited to, about 2 nm to about 100 nm, preferably about 2 nm to about 30 nm, and more preferably about 2 nm to about 20 nm. Also, each of the EML2 444 and the EML3 446 can have a thickness of, but is not limited to, about 5 nm to about 100 nm, preferably about 10 nm to about 30 nm, and more preferably about 10 nm to about 20 nm.

When the EML2 444 is disposed adjacently to the EBL 465 in one exemplary aspect, the fourth compound, which is included in the EML2 444 together with the fifth compound FD1, can be the same material as the EBL 465. In this case, the EML2 444 can have an electron blocking function as well as an emission function. For example, the EML2 444 can act as a buffer layer for blocking electrons. In one aspect, the EBL 465 can be omitted where the EML2 444 can be an electron blocking layer as well as an emitting material layer.

When the EML3 446 is disposed adjacently to the HBL 475 in another exemplary aspect, the sixth compound, which is included in the EML3 446 together with the seventh compound FD2, can be the same material as the HBL 475. In this case, the EML3 446 can have a hole blocking function as well as an emission function. For example, the EML3 446 can act as a buffer layer for blocking holes. In one aspect, the HBL 475 can be omitted where the EML3 446 can be a hole blocking layer as well as an emitting material layer.

In still another exemplary aspect, the fourth compound in the EML2 444 can be the same material as the EBL 465 and the sixth compound in the EML3 446 can be the same material as the HBL 475. In this aspect, the EML2 444 can have an electron blocking function as well as an emission function, and the EML3 446 can have a hole blocking function as well as an emission function. For example, each of the EML2 444 and the EML3 446 can act as a buffer layer for blocking electrons or hole, respectively. In one aspect, the EBL 465 and the HBL 475 can be omitted where the EML2 444 can be an electron blocking layer as well as an emitting material layer and the EML3 446 can be a hole blocking layer as well as an emitting material layer.

When the bipolar organic compound having the structure of Chemical Formulae 1 to and 6 is introduced in the EML 440, holes and electrons are injected into the EML 440 in balance, the recombination zone is formed over the whole area of the EML 440. The OLED D4 can be driven at a lower voltage, thus can reduce its power consumption and improve its luminous efficiency and color purity.

Figure 13:
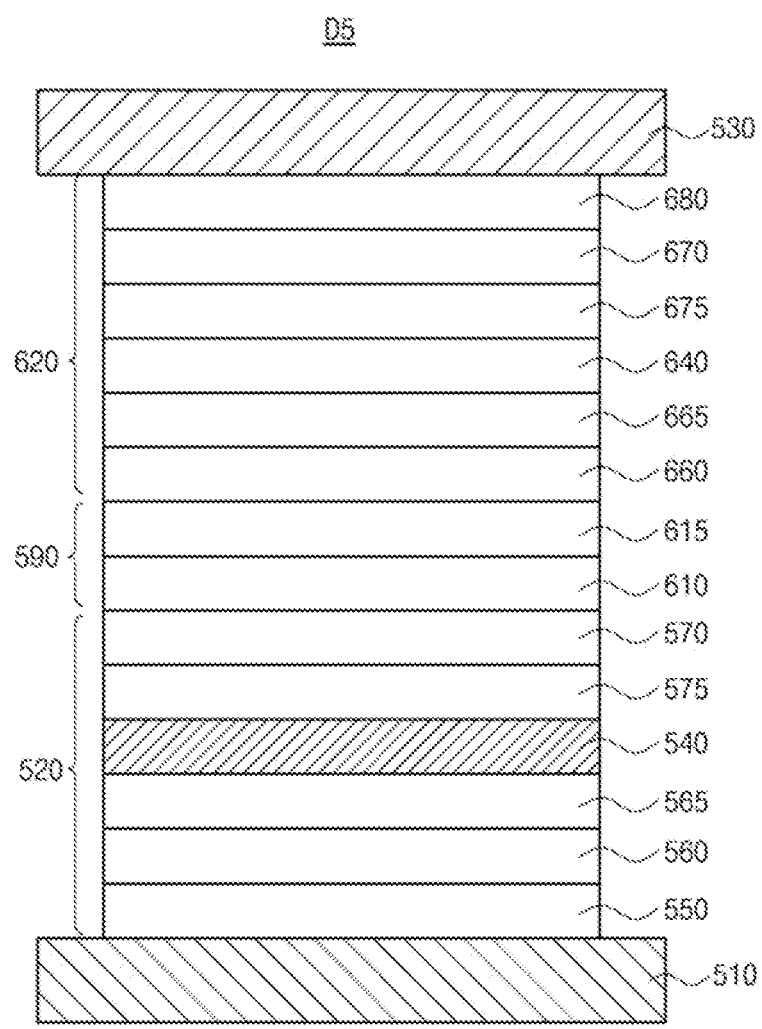
FIG. 13 is a schematic cross-sectional view illustrating an OLED in accordance with another exemplary aspect of the present disclosure.

In the above aspects, the OLEDs having single emitting unit are described. Unlike the above aspects, the OLED can have multiple emitting units so as to form a tandem structure. FIG. 13 is a cross-sectional view illustrating an OLED in accordance with still another aspect of the present disclosure.

As illustrated in FIG. 13, the OLED D5 comprises first and second electrodes 510 and 530 facing each other, a first emitting unit 520 disposed between the first and second electrodes 510 and 530, a second emitting unit 620 disposed between the first emitting unit 520 and the second electrode 530, and a charge generation layer (CGL) 590 disposed between the first and second emitting units 520 and 620.

The first electrode 510 can be an anode and include, but is not limited to, a conductive material having a relatively large work function values. As an example, the first electrode 510 can include, but is not limited to, ITO, IZO, SnO, ZnO, ICO, AZO, and the like. The second electrode 530 can be a cathode and can include, but is not limited to, a conductive material having a relatively small work function values such as Al, Mg, Ca, Ag, alloy thereof or combination thereof. Each of the first and second electrodes 510 and 530 can be laminated with a thickness of, but is not limited to, about 30 nm to about 300 nm.

The first emitting unit 520 comprises a lower EML 540. Also, the first emitting unit comprises a HIL 550 and a first HTL (HTL1) 560 each of which is disposed sequentially between the first electrode 510 and the lower EML 540, a first ETL (ETL1) 570 disposed between the lower EML 540 and the CGL 590. Alternatively, the first emitting unit 520 can further comprise a first EBL (EBL1) 565 disposed between the HTL1 560 and the lower EML 540 and/or a first HBL (HBL1) 575 disposed between the lower EML 540 and the ETL1 570.

The second emitting unit 620 comprises an upper EML 640. The second emitting unit 620 comprises a second HTL (HTL2) 660 disposed between the CGL 590 and the upper EML 640, and a second ETL (ETL2) 670 and an EIL 680 each of which is disposed sequentially between the upper EML 640 and the second electrode 530. Alternatively, the second emitting unit 620 can further comprise a second EBL (EBL2) 665 disposed between the HTL2 660 and the upper EML 640 and/or a second HBL (HBL2) 675 disposed between the upper EML 640 and the ETL2 670.

At least one of the lower EML 540 and the upper EML 640 can comprise any organic compound having the structure of Chemical Formulae 1 to 3 and 6 and emit anyone of blue (B), green (G) and red (R), and the other of the lower EML 540 and the upper EML 640 emit other colors. For example, one of the lower EML 540 and the upper EML 640 can emit blue (B) light and the other of the lower EML 540 and the upper EML 640 can emit red (R) and/or green (G) light. Hereinafter, the OLED D5, where the lower EML 540 emits blue light and the upper EML 640 emits green and/or red light, will be explained.

The HIL 550 is disposed between the first electrode 510 and the HTL1 560 and improves an interface property between the inorganic first electrode 510 and the organic HTL 560. In one exemplary aspect, the HIL 550 can comprise, but is not limited to, MTDATA. NATA, 1T-NATA, 2T-NATA, CuPc, TCTA, NPB(NPD), HAT-CN. TDAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 550 can be omitted in compliance with a structure of the OLED D5.

Each of the HTL1 560 and the HTL2 660 can independently include, but is not limited to, TPD, NPD(NPB), CBP, poly-TPD, TFB, TAPC, N-(biphenyl-4-yl)-9,9-dimethyl-N-(4-(9-phenyl-9H-carbazol-3-yl)phenyl)-9l-fluoren-2-amine and/or N-(biphenyl-4-yl)-N-(4-(9-phenyl-9H-carbazol-3-yl)phenyl)biphenyl-4-amine.

Each of the ETL1 570 and the ETL2 670 facilitates electron transportations in the first emitting unit 520 and the second emitting unit 620, respectively. Each of the ETL1 570 and the ETL2 670 can independently include, but is not limited to, oxadiazole-based compounds, triazole-based compounds, phenanthroline-based compounds, benzoxazole-based compounds, benzothiazole-based compounds, benzimidazole-based compounds, triazine-based compounds, and the like, respectively. As an example, each of the ETL1 570 and the ETL2 670 can independently include, but is not limited to, $Alq_3$, PBD, spiro-PBD, Liq, TPBi, BAIq, Bphen, NBphen, BCP, TAZ, NTAZ, TpPyPB, TmPP-PyTz, PFNBr and/or TPQ, respectively.

Alternatively, at least one of the ETL1 570 and the ETL2 670 can comprise anyone having the structure of Chemical Formulae 1 to 3 and 6. In this case, the at least one of the ETL1 570 and the ETL2 670 can comprise only the organic compound having the structure of Chemical Formulae 1 to 3 and 6, or comprise the above-described electron transporting materials mixed or doped with the organic compound.

The EIL 680 is disposed between the second electrode 530 and the second ETL 670, and can improve physical properties of the second electrode 530 and therefore, can enhance the lifetime of the OLED D5. In one exemplary aspect, the EIL 580 can include, but is not limited to, an alkali halide such as LiF, CsF, NaF, $BaF_2$ and the like, and/or an organic metal compound such as lithium benzoate, sodium stearate, and the like.

Each of the EBL1 565 and the EBL2 665 can independently include, but is not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, mCP, mCBP, CuPc, N,N'-bis[4-(bis(3-methylphenyl)amino)phenyl]-N,N'-diphenyl-[1,1'-biphenyl]-4,4'-diamine (DNTPD), TDAPB and/or 3,6-bis(N-carbazolyl)-N-phenyl-carbazole, respectively.

Each of the HBL1 575 and the HBL2 675 can independently include, but is not limited to, oxadiazole-based compounds, triazole-based compounds, phenanthroline-based compounds, benzoxazole-based compounds, benzothiazole-based compounds, benzimidazole-based compounds, and triazine-based compounds. As an example, each of the HBL1 575 and the HBL2 675 can independently include, but is not limited to, BCP, BAlq, $Alq_3$, PBD, spiro-PBD, Liq, B3PYMPM, DPEPO, 9-(6-(9H-carbazol-9-yl)pyridine-3-yl)-9H-3,9'-bicarbazole and combination thereof, respectively.

Alternatively, at least one of the HBL1 575 and the HBL2 675 can comprise anyone having the structure of Chemical Formulae 1 to 3 and 6. In this case, the at least one of the HBL1 575 and the HBL2 675 can comprise only the organic compound having the structure of Chemical Formulae 1 to 3 and 6, or comprise the above-described electron transporting materials mixed or doped with the organic compound.

In one exemplary aspect, when the upper EML 640 emits green light, the upper EML 640 can emit green (G) or yellow-green (YG) light. In this case, the upper EML 640 can comprise a green host and a green dopant. For example, the green host can comprise, but is not limited to, 9,9'-Diphenyl-9H,9'H-3,3'-bicarbazole (BCzPh), CBP, 1,3,5-Tris(carbazole-9-yl)benzene (TCP), TCTA, 4,4'-Bis(carbazole-9-yl)-2,2'-dimethylbipheyl (CDBP), 2,7-Bis(carbazole-9-yl)-9,9-dimethylfluorene (DMFL-CBP), 2,2',7,7'-Tetrakis(carbazole-9-yl)-9,9-spiorofluorene (Spior-CBP), DPEPO, 4'-(9H-carbazol-9-yl)biphenyl-3,5-dicarbonitrile (PCzB-2CN), 3'-(9H-carbazol-9-yl)biphenyl-3,5-dicarbonitrile (mCzB-2CN), 3,6-Bis(carbazole-9-yl)-9-(2-ethyl-hexyl)-9H-carbazole (TCzl), and the like.

The green dopant can comprise, but is not limited to, [Bis(2-phenylpyridine)](pyridyl-2-benzofuro[2,3-b]pyridine)iridium), fac-Tris(2-phenylpyridine)iridium(III) (fac-Ir$(ppy)_3$), Bis(2-phenylpyridine)(acetylacetonate)iridium(III) (Ir$(ppy)_2$(acac), Tris[2-(p-tolyl)pyridine]iridium(III) (Ir(m-ppy)$_3$, Bis(2-(naphthalene-2-yl)pyridine)(acetylacetonate) iridium(III) (Ir(npy)$_2$acac), Tris(2-phenyl-3-methyl-pyridine)iridium (Ir(3mppy)$_3$), fac-Tris(2-(3-p-xylyl)phenyl) pyridine iridium(III) (TEG), and the like. In this case, the upper EML 640 can emit green light with wavelength of about 510 nm to about 590 nm.

In an alternative aspect, when the upper EML 640 is the red EML, the upper EML 640 can a red host and a red dopant. The red host can comprise, but is not limited to, the green host above as well as Bis(2-hydroxylphenyl)-pyridine)beryllium (Bepp$_2$), Bis(10-hydroxybenzo[h]quinolinato)beryllium (Bebq$_2$), 1,3,5-Tris(1-pyrenyl)benzene (TPB3), and the like.

The red dopant can comprise, but is not limited to, [Bis(2-(4,6-dimethyl)phenylquinoline)](2,2,6,6-tetramethylheptane-3,5-dionate)iridium(III), Bis[2-(4-n-hexylphenyl)quinoline](acetylacetonate)iridium(III) (Hex-Ir(phq)$_2$(acac)), Tris[2-(4-n-hexylphenyl)quinoline]iridium(III) (Hex-4r(phq)$_3$), Tris[2-phenyl-4-methylquinoline]iridium (III) (Ir(Mphq)$_3$), Bis(2-phenylquinoline)(2,2,6,6-tetramethylheptene-3,5-dionate)iridium(III) (Ir(dpm)PQ$_2$), Bis(phenylisoquinoline)(2,2,6,6-tetramethylheptene-3,5-dionate) iridium(III) (Ir(dpm)(piq)$_2$), Bis[(4-n-hexylphenyl) isoquinoline](acetylacetonate)iridium(III) (Hex-Ir(piq)$_2$ (acac)), Tris[2-(4-n-hexylphenyl)quinoline]iridium(III) (Hex-Ir(piq)₃), Tris(2-(3-methylphenyl)-7-methyl-quinolato)iridium (Ir(dmpq)₃), Bis[2-(2-methylphenyl)-7-methylquinoline](acetylacetonate)iridium(III) (Ir(dmpq)₂(acac)), Bis[2-(3,5-dimethylphenyl)-4-methylquinoline](acetylacetonate)iridium(III) (Ir(mphmq)₂(acac)), and the like. In this case, the upper EML 640 can emit red light with wavelength of about 600 nm to about 650 nm.

Alternatively, the second emitting unit 620 can comprise two emitting material layers, for example green and red emitting materials layers in order to enhance the red efficiency of the OLED D5. In this case, the second emitting unit 620 can emit light having wavelength of about 510 nm to about 650 nm.

The CGL 590 is disposed between the first emitting unit 520 and the second emitting unit 620. The CGL 590 includes an N-type CGL 610 disposed adjacently to the first emitting unit 520 and a P-type CGL 615 disposed adjacently to the second emitting unit 620. The N-type CGL 610 injects electrons into the first emitting unit 520 and the P-type CGL 615 injects holes into the second emitting unit 620.

As an example, the N-type CGL 610 can be an organic layer doped with an alkali metal such as Li, Na, K and/or Cs and/or an alkaline earth metal such as Mg, Sr, Ba and/or Ra. For example, a host used in the N-type CGL 610 can include, but is not limited to, an organic compound such as Bphen or MTDATA. The alkali metal or the alkaline earth metal can be doped with about 0.01 wt % to about 30 wt %.

Alternatively, the N-type CGL 610 can comprise any organic compound having the structure of Chemical Formulae 1 to 3 and 6. As described above, any organic compound having the structure of Chemical Formulae 1 to 3 and 6 has high affinity to electrons. In this case, the N-type CTL 610 can comprise only the organic compound having the structure of Chemical Formulae 1 to 3 and 6, or further comprise the alkali metal or the alkaline earth metal doped with the organic compound.

The P-type CGL 615 can include, but is not limited to, an inorganic material selected from the group consisting of tungsten oxide ($WO_x$), molybdenum oxide ($MoO_x$), beryllium oxide ($Be_2O_3$), vanadium oxide ($V_2O_5$) and combination thereof, and/or an organic material selected from the group consisting of NPD, HAT-CN, 2,3,5,6-Tetrafluoro-7,7,8,8-tetracyanoquinodimethane (F4TCNQ), TPD, N,N,N',N'-Tetranaphthalenyl-benzidine (TNB), TCTA, N,N'-dioctyl-3, 4,9,10-perylenedicarboximide (PTCDI-C8) and combination thereof.

The lower EML 540 comprises the first compound that can be the host and the second compound that can be the dopant such as the delayed fluorescent material. The first compound can comprise any organic compound having the structure of Chemical Formulae 1 to 3 and 6. The second compound emitting blue light can comprise SPXZPO, DPXZPO, TPXZPO, DcZTrz, DDczTrz, DMTDAc, DMOC-DPS, DMAC-DPS, DMAC-TRZ, ACRSA, Cz-VPN, TcZTrz, mPTC, CC2BP, BDPCC-TPTA, BCC-TPTA, DPCC-TPTA, Phen-TRZ, Cab-Ph-TRZ, SpiroAC-TRZ, 3CzFCN and 4CzFCN.

Similar to the first aspect, the singlet exciton energy generated at the first compound that can be the host can be transferred to the singlet exciton of the second compound that can be the delayed fluorescent material in the lower EML 540. Each of the excited singlet energy level $S_1^{H1}$ and the excited triplet energy level $T_1^{H1}$ of the first compound is higher than each of the excited singlet energy level $S_1^{TD}$ and the excited triplet energy level $T_1^{TD}$ of the second compound having the delayed fluorescent property, respectively (see, FIG. 6). As an example, the excited triplet energy levels $T_1^H$ of the first compound can be higher than the excited triplet energy level $T_1^{TD}$ of the second compound by at least about 0.2 eV, for example at least about 0.3 eV, preferably at least about 0.5 eV.

The lower EML 540 implements fluorescent emission as the singlet exciton energy transferred from the first compound to the second compound is shifted to the ground state. In addition, the lower EML 540 implements delayed fluorescent emission as the triplet exciton energy of the second compound is converted to its own singlet exciton energy by RISC mechanism, and then the converted singlet exciton energy is shifted to the ground state. Since the second compound emits light utilizing both the excited singlet exciton and the excited triplet exciton, the OLED D5 can enhance its luminous efficiency.

In addition, when any organic compound having the structure of Chemical Formulae 1 to 3 and 6 and having the bipolar property is introduced into the lower EML 540, the recombination zone among the electrons and holes are distributed uniformly over the whole area in the lower EML 540, thereby improving the luminous efficiency of the OLED D5. Moreover, when the organic compound is introduced into the lower EML 540, the OLED D5 can be driven at lower voltage, and thereby reducing the power consumption.

In this case, the contents of the second compound in the lower EML 540 can be about 1 wt % to about 70 wt %, preferably about 10 wt % to about 50 wt %, and more preferably about 20 wt % to about 50 wt %. The lower EML 540 can have a thickness of, but is not limited to, about 10 nm to about 200 nm, preferably about 20 to about 100 nm, and more preferably about 30 nm to about 50 nm.

In an alternative aspect, the lower EML 540 can comprise the first compound that can be the host, the second compound that can be the delayed fluorescent material, and the third compound that can be the fluorescent or phosphorescent material (see. FIG. 7). In another exemplary aspect, the lower EML 540 can have a double-layered structure that comprises an EML1 and an EML2. In this case, the EML1 can comprise the first compound that can be the first host and the second compound that can be the delayed fluorescent material while the EML2 can comprise the fourth compound that can be the second host and the fifth compound that can be the fluorescent or phosphorescent material (see, FIG. 9). In still another aspect, the lower EML 540 can have a triple-layered structure that further comprises an EML3 disposed oppositely to the EML2 with respect to the EML1. In this case, the EML3 can comprise the sixth compound that can be the third host and the seventh compound that can be the fluorescent or phosphorescent material (see, FIG. 11).

In still another exemplary aspect, an OLED of the present disclosure can comprise three or more emitting units. For example, the OLED can further comprise a third emitting unit disposed between the second emitting unit 620 and the second electrode 530 and a second CGL disposed between the second emitting unit 620 and the third emitting unit.

Synthesis Example 1: Synthesis of Compound 1

(1) Synthesis of Intermediate 1-2

[Reaction Formula 1-1]

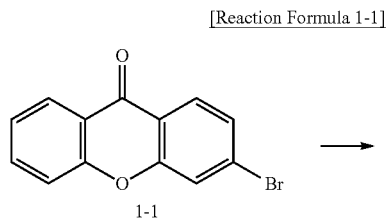

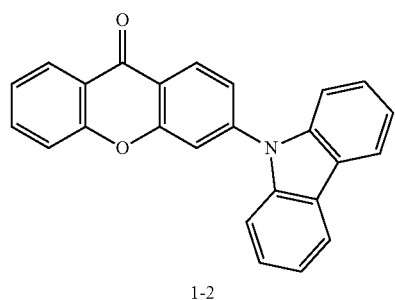

Compound 1-1 (10 g, 0.036 mmol), carbazole (7.89 g, 0.047 mmol) and K$_2$CO$_3$ dissolved in o-xylene (100 mL) was put into a reactor, and the solution was stirred for 30 minutes under nitrogen atmosphere. Palladium(II) acetate (Pd(OAc)$_2$, 160 mg, 2 mol %) and tri-tert-butyl phosphine (P(t-Bu)$_3$, 400 mg, 6 mol %) were added into the reactor, and the solution was stirred at 140° C. for 24 hours. After the reactor was cooled down to room temperature and the reaction solvent was removed, the crude product was purified with a column chromatography to give light yellow solid intermediate 1-2 (10.4 g, yield: 79.2%).

(2) Synthesis of Compound 1

[Reaction Formula 1-2]

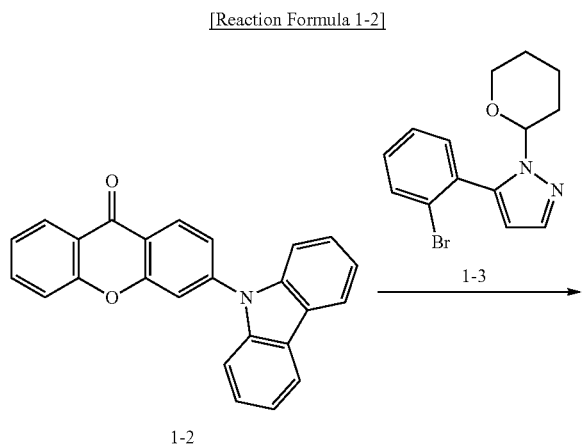

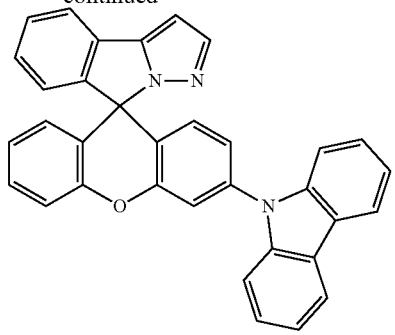

Compound 1-3 (6.76 g, 0.022 mmol) was dissolved in THF (60 mL) under nitrogen atmosphere and then the solution was cooled down to −78° C. 2.5 M n-BuLi (8 mL) was added slowly drop wise to the reaction solution. After stirring at the same temperature for 1 hour, the intermediate 1-2 (7.22 g, 0.02 mmol) was added to the solution at one time. After stirring at a room temperature for 6 hours, the solution was extracted with diethyl ether to remove the solvents. The organic layer was dissolved in acetic acid (50 mL) without purification, and then HCl (2 mL) was added slowly to the solution. After stirring at a room temperature for 1 hour, the solution was neutralized with NaHCO$_3$ aqueous solution and then extracted with methylene chloride. After removing the solvents, the crude product was purified with a column chromatography to give white solid Compound 1 (3.9 g, yield: 40%).

Synthesis Example 2: Synthesis of Compound 6

(1) Synthesis of Intermediate 2-2

[Reaction Formula 2-1]

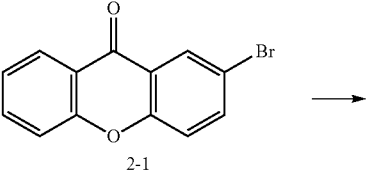

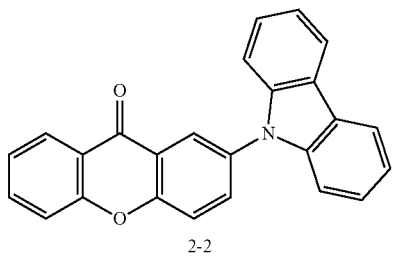

Compound 2-1 (10 g, 0.036 mmol), carbazole (7.89 g, 0.047 mmol) and K$_2$CO$_3$ dissolved in o-xylene (100 mL) was put into a reactor, and the solution was stirred for 30 minutes under nitrogen atmosphere. Pd(OAc)$_2$ (160 mg, 2 mol %) and (P(t-Bu)$_3$ (400 mg, 6 mol %) were added into the reactor, and the solution was stirred at 140° C. for 24 hours. After the reactor was cooled down to room temperature and the reaction solvent was removed, the crude product was purified with a column chromatography to give light yellow solid intermediate 2-2 (10.4 g, yield: 79.2%).

(2) Synthesis of Compound 6

[Reaction Formula 2-2]

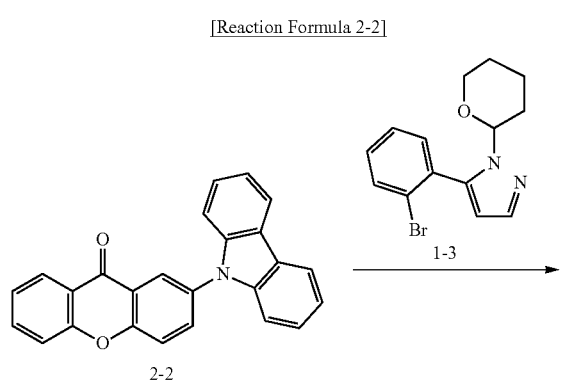

Compound 1-3 (6.76 g, 0.022 mmol) was dissolved in THF (60 mL) under nitrogen atmosphere and then the solution was cooled down to −78° C. 2.5 M n-BuLi (8 mL) was added slowly drop wise to the reaction solution. After stirring at the same temperature for 1 hour, the intermediate 2-2 (7.22 g, 0.02 mmol) was added to the solution at one time. After stirring at a room temperature for 6 hours, the solution was extracted with diethyl ether to remove the solvents. The organic layer was dissolved in acetic acid (50 mL) without purification, and then HCl (2 mL) was added slowly to the solution. After stirring at a room temperature for 1 hour, the solution was neutralized with NaHCO₃ aqueous solution and then extracted with methylene chloride. After removing the solvents, the crude product was purified with a column chromatography to give white solid Compound 6 (3.9 g, yield: 40%).

Synthesis Example 3: Synthesis of Compound 17

(1) Synthesis of Intermediate 3-2

[Reaction Formula 3-1]

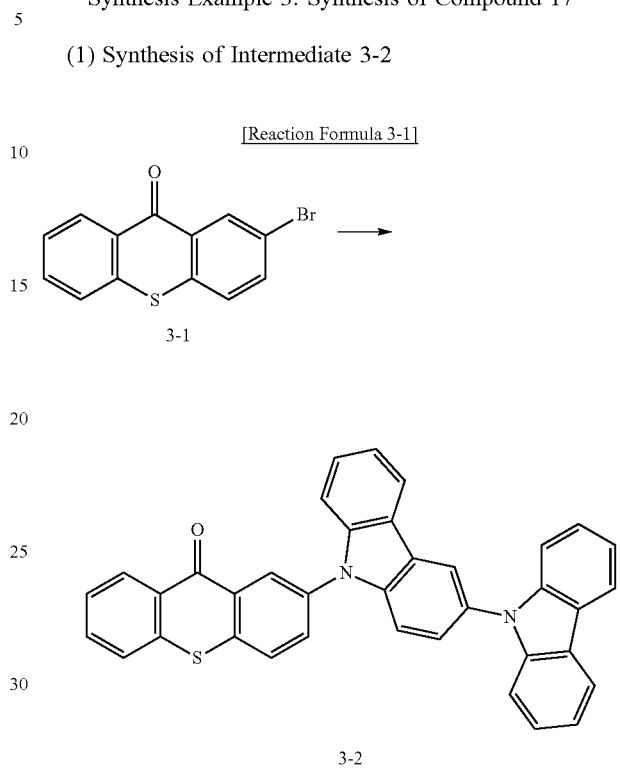

Compound 3-1 (10 g, 0.034 mmol), bicarbazole (15.86 g, 0.047 mmol) and K₂CO₃ dissolved in o-xylene (100 mL) was put into a reactor, and the solution was stirred for 30 minutes under nitrogen atmosphere. Pd(OAc)₂ (160 mg, 2 mol %) and (P(t-Bu)₃ (400 mg, 6 mol %) were added into the reactor, and the solution was stirred at 140° C. for 24 hours. After the reactor was cooled down to room temperature and the reaction solvent was removed, the crude product was purified with a column chromatography to give yellow solid intermediate 3-2 (10.4 g, yield: 45%).

(2) Synthesis of Compound 17

[Reaction Formula 3-2]

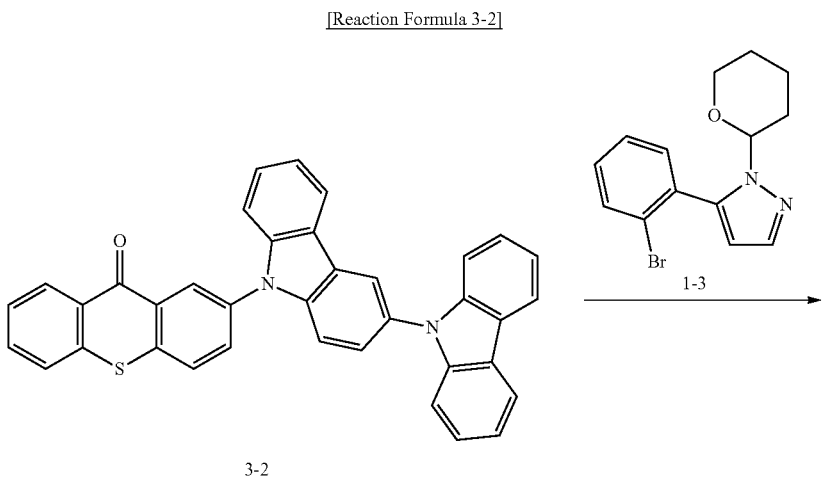

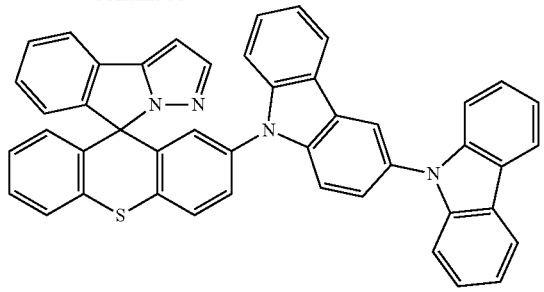

17

Compound 1-3 (5 g, 0.016 mmol) was dissolved in THF (60 mL) under nitrogen atmosphere and then the solution was cooled down to −78° C. 2.5 M n-BuLi (8 mL) was added slowly drop wise to the reaction solution. After stirring at the same temperature for 1 hour, the intermediate 3-2 (7.05 g, 0.013 mmol) was added to the solution at one time. After stirring at a room temperature for 6 hours, the solution was extracted with diethyl ether to remove the solvents. The organic layer was dissolved in acetic acid (50 mL) without purification, and then HCl (2 mL) was added slowly to the solution. After stirring at a room temperature for 1 hour, the solution was neutralized with NaHCO$_3$ aqueous solution and then extracted with methylene chloride. After removing the solvents, the crude product was purified with a column chromatography to give white solid Compound 17 (2.1 g, yield: 24%).

Experimental Example 1: Measurement of Energy Level

HOMO energy level, LUMO energy level, excited single energy level ($S_1$) and excited triple energy level ($T_1$) for the Compounds synthesized in Synthesis Examples as well as conventional host CBP, the reference compound 1 (Ref. 1), the reference compound 2 (Ref. 2), reference compound 3 (Ref. 3) and the reference compound 4 (Ref. 4) as indicated below were measured by simulation. The measurement results are shown in Table 1 below.

[Reference Compounds]

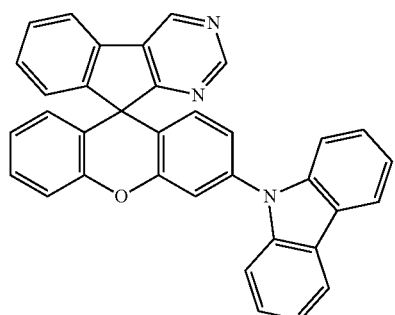

Ref. 1

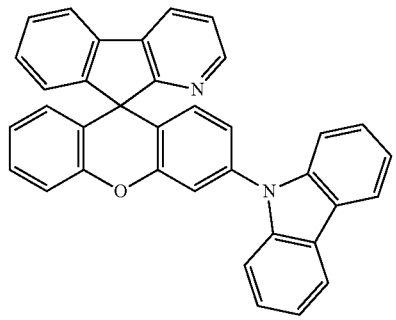

Ref. 2

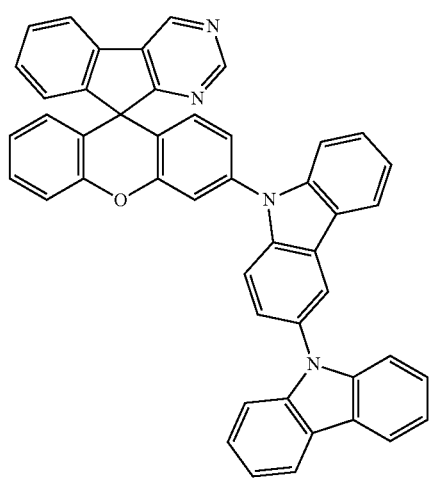

Ref. 3

-continued

Ref. 4

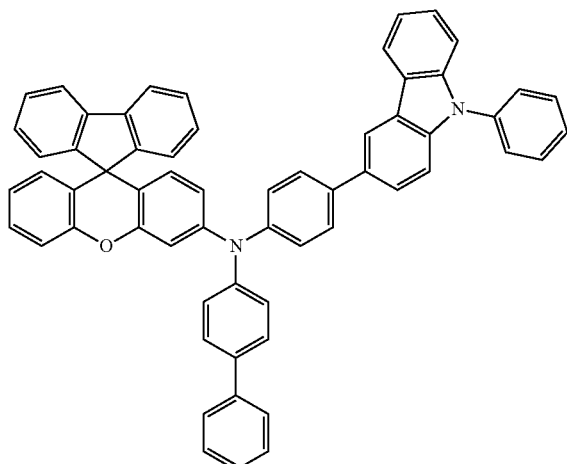

TABLE 1

Energy Levels of Organic Compound

| Compound | HOMO* (eV) | LUMO* (eV) | Eg* (eV) | $T_1$* (eV) | $S_1$ (eV) | $\Delta E_{ST}$* |
|---|---|---|---|---|---|---|
| 1 | −5.7 | −2.1 | 3.6 | 2.92 | 3.29 | 0.37 |
| 6 | −5.7 | −2.2 | 3.5 | 2.93 | 3.50 | 0.57 |
| 17 | −5.8 | −2.2 | 3.6 | 2.87 | 3.29 | 0.42 |
| CBP | −6.0 | −2.9 | 3.1 | 2.58 | — | — |
| Ref. 1 | −5.8 | −2.9 | 2.9 | 2.75 | 2.76 | 0.01 |
| Ref. 2 | −5.7 | −2.5 | 3.2 | 2.79 | 2.86 | 0.07 |
| Ref. 3 | −5.8 | −2.9 | 2.9 | 2.72 | 2.76 | 0.04 |
| Ref. 4 | −5.3 | −2.6 | 2.7 | 2.41 | 2.79 | 0.38 |

*HOMO, LUMO, Eg: LUMO − HOMO, $T_1$, $\Delta E_{ST}$: calculation @ Schrodinger simulation As indicated in Table 1, all the organic compounds synthesized in Synthesis Examples have proper HOMO energy levels, LUMO energy levels, energy bandgaps and excited singlet and triplet energies for an emissive layer. Particularly, the organic compounds have very high excited triplet energy levels and were proper for the host in EML as materials for the ETL and HBL considering the energy bandgap between the $S_1$ and $T_1$. On the contrary, Ref. compounds 1-3 have excited triplet energy levels not relatively high and do not have energy level bandgap between $S_1$ and $T_1$ proper for the host in EML. In addition, the Ref. 4 has so low excited triplet energy level, and thus is not suitable for use as the host in EML.

Example 1 (Ex. 1): Fabrication of OLED

An OLED in which the Compound 1 is used as a host of an EML was fabricated. An ITO attached glass substrate (40 mm×40 mm×0.5 mm) was washed with supersonic with isopropyl alcohol, acetone and DI water for 5 minutes and then dried in an oven at 100° C. The substrate was treated with $O_2$ plasma for 2 minutes under vacuum, was loaded into the vapor system, and then was transferred to a vacuum deposition chamber in order to deposit other layers on the substrate. An organic layer was deposited by evaporation by a heated boat under $10^{-7}$ torr at a deposition rate of 1 Å in the following order:

A HIL (HAT-CN; 50 Å); a HTL (NPB, 500 Å); an EBL (mCP; 100 Å); an EML (Compound 1(host): triazine-based compound below (dopant)=70:30 by weight; 300 Å); an ETL (TPBi; 350 Å); an EIL (LiF; 10 Å); and a cathode (Al; 1000 Å).

And then, cappling layer (CPL) was deposited over the cathode and the device was encapsualted by glass. After deposition of emissive layer and the cathode, the OLED was transferred from the deposition chamber to a dry box for film formation, followed by encapsulation using UV-curable epoxy resin and moisture getter.

[Dopant]

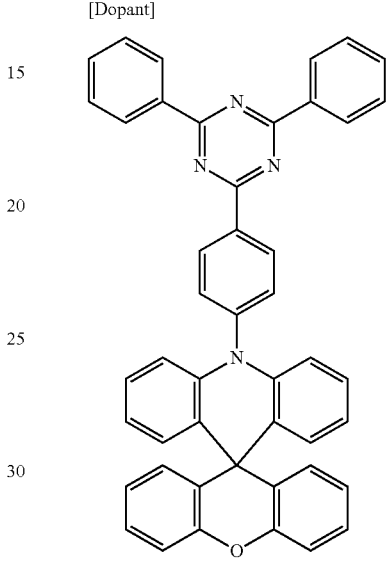

Examples 2-5 (Ex. 2-3): Fabrication of OLED

An OLED was fabricated using the same materials as Example 1, except that Compound 6 (Ex. 2) or Compound 17 (Ex. 3) was applied into the EML as the host instead of the Compound 1.

Comparative Examples 1-2 (Com. 1-2): Fabrication of OLED

OLED was fabricated using the same materials as Example 1, except that CBP (Com. 1) or Ref. 2 compound (Com. 2) was applied into the EML as the host instead of the Compound 1

Experimental Example 2: Measurement of Luminous Properties of OLED

Each of the OLED fabricated by Ex. 1-3 and Com. 1-2 having 9 mm² of luminous area was connected to an external power source and then luminous properties for all the diodes were evaluated using a constant current source (KEITHLEY) and a photometer PR650 at a room temperature. In particular, driving voltage (V), external quantum efficiency (EQE, %) and CIE color coordinates at a current density of 10 mA/cm² were measured. The results thereof are shown in the following Table 2.

TABLE 2

| Sample | Host | V | EQE (%) | CIEx, CIEy |
|---|---|---|---|---|
| Com. 1 | CBP | 4.60 | 6.7 | (0.171, 0.346) |
| Com. 2 | Ref. 2 | 4.52 | 10.0 | (0.174. 0.353) |
| Ex. 1 | Compound 1 | 3.60 | 14.2 | (0.173, 0.369) |
| Ex. 2 | Compound 6 | 3.68 | 15.4 | (0.173, 0.365) |
| Ex. 3 | Compound 17 | 3.64 | 11.2 | (0.174, 0.352) |

As indicated in Table 2, compared to the OLED in Com. 1 which uses CBP as the host, the OLEDs in Ex. 1-3 lowered their driving voltages up to 21.7% and enhanced their EQE up to 129.9%. Also, compared to the OLED in Com. 2 which uses Ref. 1 as the host, the OLEDs in Ex. 1-3 lowered their driving voltages up to 20.4% and enhanced their EQE up to 54%. It is possible to manufacture an OLED and an organic light emitting device having the OLED each of which lowers its driving voltages and power consumption and enhances its luminous efficiency.

It will be apparent to those skilled in the art that various modifications and variations can be made in the present disclosure without departing from the scope of the invention. Thus, it is intended that the present disclosure cover the modifications and variations of the present disclosure provided they come within the scope of the appended claims.

What is claimed is:

1. An organic compound comprising the following structure of Chemical Formula 1:

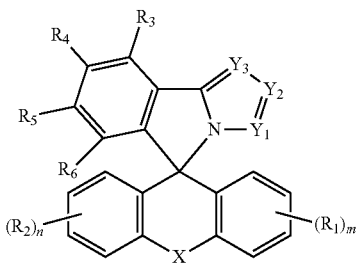

Chemical Formula 1 wherein:
each of $R_1$ and $R_2$ is independently hydrogen, an unsubstituted or substituted $C_1$-$C_{20}$ alkyl group, or an unsubstituted or substituted hetero aromatic group having one to three carbazolyl moieties, wherein at least one of $R_1$ and $R_2$ is the hetero aromatic group;
each of m and n is the number of substituent and is independently an integer between 0 (zero) to 4;
each of $R_3$ to $R_6$ is independently hydrogen, an unsubstituted or substituted $C_1$-$C_{20}$ alkyl group, an unsubstituted or substituted $C_1$-$C_{20}$ alkoxy group, an unsubstituted or substituted $C_6$-$C_{30}$ aromatic group or an unsubstituted or substituted $C_3$-$C_{30}$ hetero aromatic group;
X is O or S; and
each of $Y_1$ to $Y_3$ is independently N or $CR_7$, wherein $R_7$ is hydrogen, an unsubstituted or substituted $C_1$-$C_{20}$ alkyl group, an unsubstituted or substituted $C_1$-$C_{20}$ alkoxy group, an unsubstituted or substituted $C_6$-$C_{30}$ aromatic group or an unsubstituted or substituted $C_3$-$C_{30}$ hetero aromatic group, and further wherein at least one of $Y_1$ to $Y_3$ is N.

2. The organic compound of claim 1, wherein the organic compound comprises an organic compound having the following structure of Chemical Formula 2:

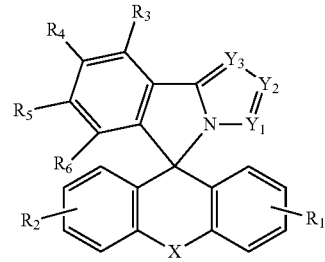

Chemical Formula 2 wherein each of $R_1$ to $R_6$, X and $Y_1$ to $Y_3$ is identical defined in Chemical Formula 1.

3. The organic compound of claim 1, wherein the organic compound comprises an organic compound having the following structure of Chemical Formula 3:

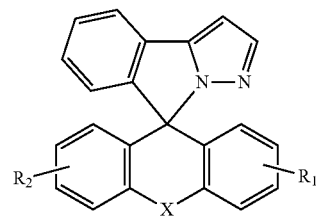

Chemical Formula 3 wherein each of $R_1$, $R_2$ and X is identical defined in Chemical Formula 1.

4. The organic compound of claim 1, wherein $R_1$ is the hetero aromatic group and a spiro moiety including X comprises one of the following structures of Chemical Formula 4:

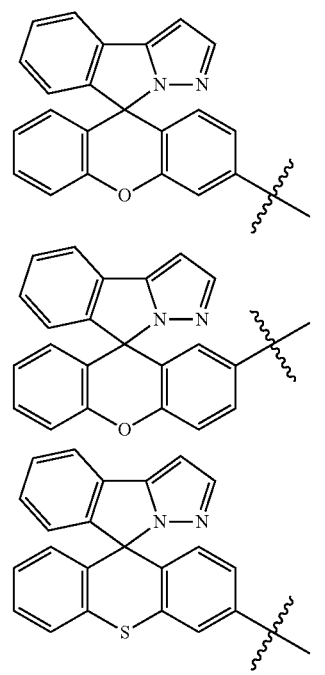

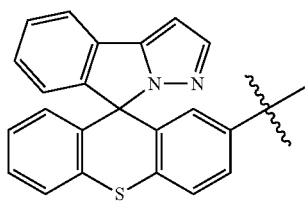

wherein the wavy portion indicates a linking site to $R_1$.

5. The organic compound of claim 1, wherein $R_1$ is selected from one of the following structures of Chemical Formula 5:

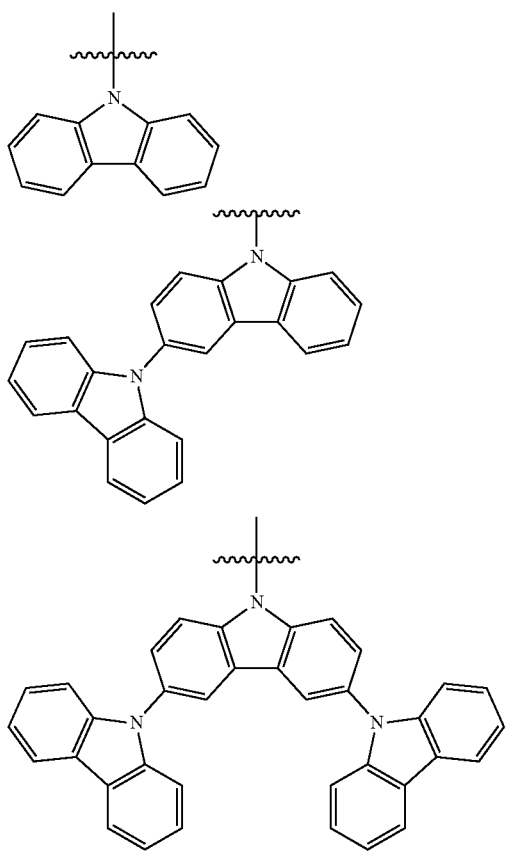

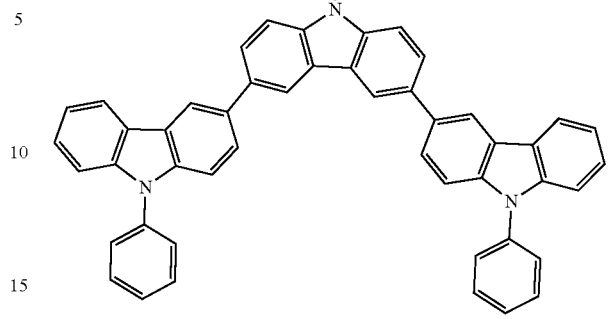

wherein the wavy portion indicates a linking site to a spiro moiety including X.

6. The organic compound of claim 1, wherein the organic compound is selected from the following compounds of Chemical Formula 6:

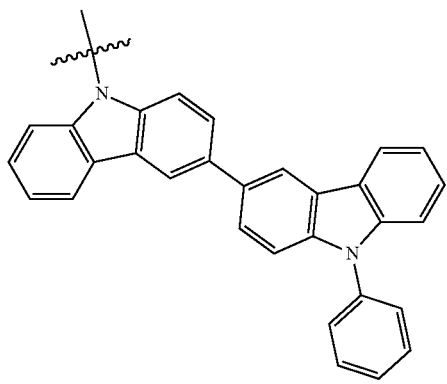

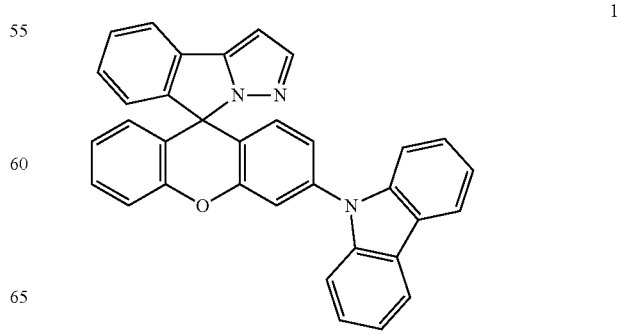

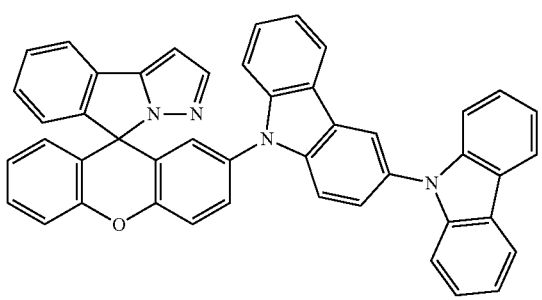
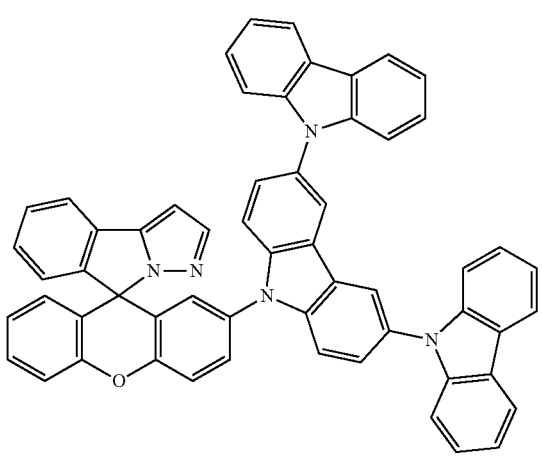
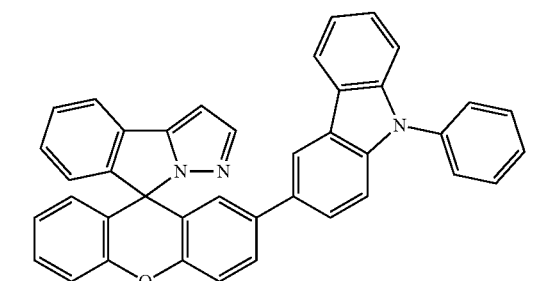
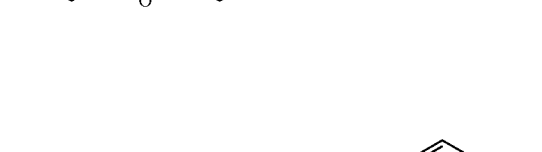
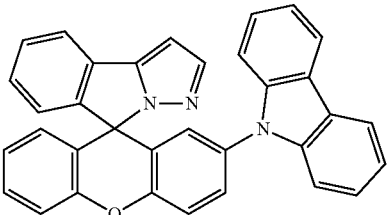
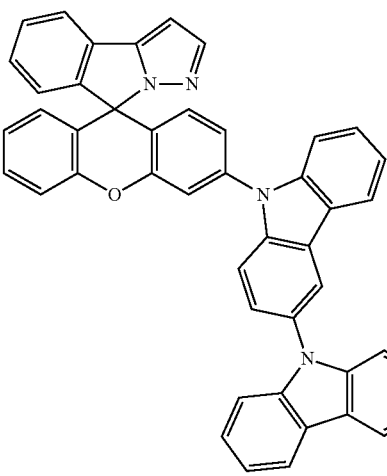
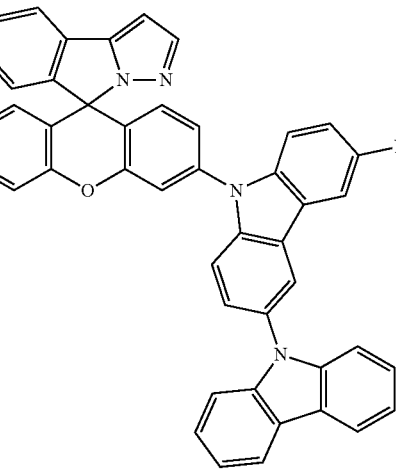
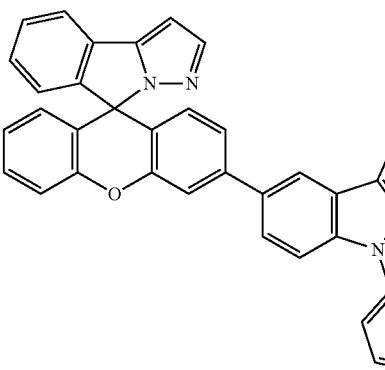

77
-continued
10
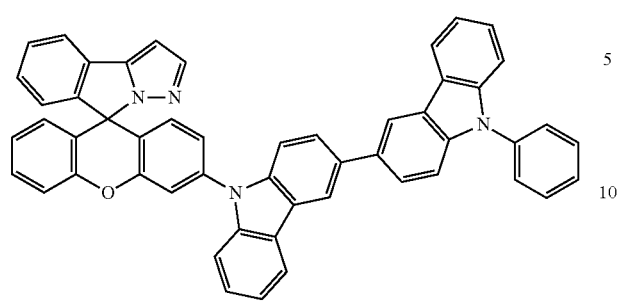
11
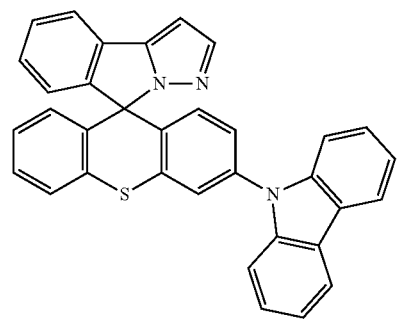
12
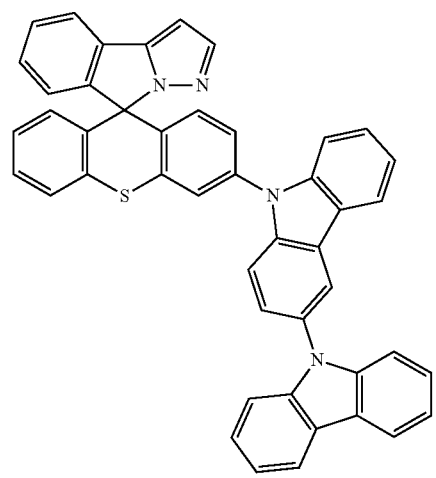
13
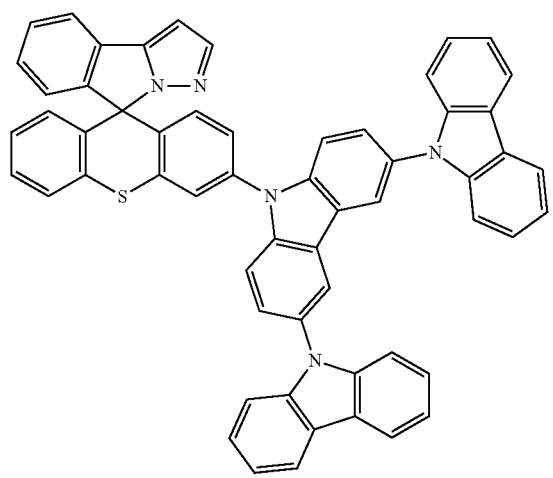
78
-continued
14
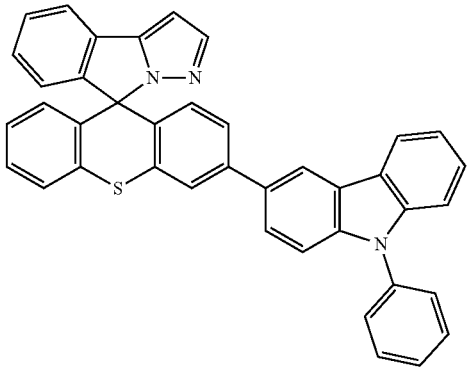
15
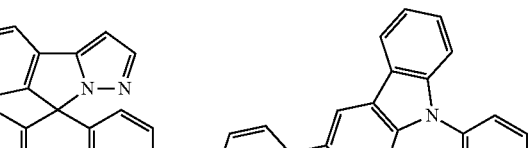
16
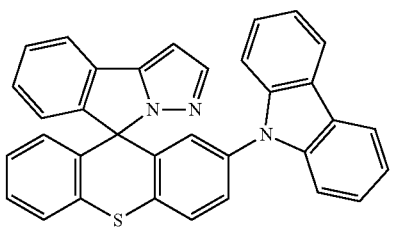
17

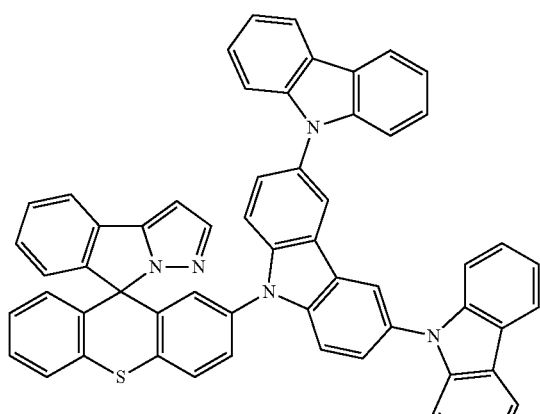
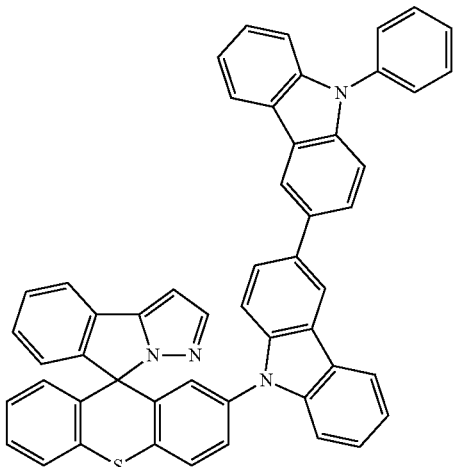
* * * * *